United States Patent
Kuhn et al.

(10) Patent No.: US 12,310,837 B1
(45) Date of Patent: May 27, 2025

(54) METHODS AND SYSTEMS FOR TRANSCAVAL TREATMENT OF ANEURYSMS

(71) Applicant: Taurus Vascular, Inc., Houston, TX (US)

(72) Inventors: Matthew Kuhn, Houston, TX (US); Ahramahzd Tatavoosian, Mission Viejo, CA (US)

(73) Assignee: Taurus Vascular, Inc., Houston, TX (US)

( * ) Notice: Subject to any disclaimer, the term of this patent is extended or adjusted under 35 U.S.C. 154(b) by 0 days.

(21) Appl. No.: 18/792,233

(22) Filed: Aug. 1, 2024

Related U.S. Application Data

(63) Continuation-in-part of application No. 18/419,262, filed on Jan. 22, 2024.

(60) Provisional application No. 63/675,198, filed on Jul. 24, 2024.

(51) Int. Cl.
  *A61F 2/07*  (2013.01)
  *A61F 2/966* (2013.01)

(52) U.S. Cl.
  CPC ............... *A61F 2/07* (2013.01); *A61F 2/966* (2013.01); *A61F 2210/0004* (2013.01); *A61F 2220/0008* (2013.01); *A61F 2230/0065* (2013.01)

(58) Field of Classification Search
  CPC ............ A61M 27/002; A61M 2205/04; A61M 2205/3331; A61M 22/127; A61B 17/11
  See application file for complete search history.

(56) References Cited

U.S. PATENT DOCUMENTS

| | | | |
|---|---|---|---|
| 6,068,638 | A  | 5/2000  | Makower |
| 6,287,317 | B1 | 9/2001  | Makower et al. |
| 6,464,665 | B1 | 10/2002 | Heuser |
| 6,485,513 | B1 | 11/2002 | Fan |
| 7,374,567 | B2 | 5/2008  | Heuser |
| 7,828,814 | B2 | 11/2010 | Brenneman et al. |

(Continued)

FOREIGN PATENT DOCUMENTS

| WO | WO-2020232384 A1 | 11/2020 |
|---|---|---|
| WO | WO-2024155994 A1 | 7/2024 |

OTHER PUBLICATIONS

International Search Report and Written Opinion in Intl. App. No. PCT/US2024/012436, mailed Jun. 13, 2024, 14 pages.

(Continued)

*Primary Examiner* — Leslie R Deak
(74) *Attorney, Agent, or Firm* — COOLEY LLP

(57) ABSTRACT

Embodiments described herein relate to a shunt including a self-adjusting mechanism for treating conditions such as an aortic aneurysm. In some embodiments, the shunt may include a central portion, a distal end, and a proximal end. In some embodiments, the distal end of the shunt may be configured to roll proximally (e.g., into a toroidal structure) when the shunt transitions from a delivery configuration to a deployed configuration. In some embodiments, the distal end of the shunt may be configured to roll and/or unroll after deployment such that a length of the shunt can be adjustable to accommodate changing anatomy. In some embodiments, the proximal end may be configured to expand into a disc-like shape when the shunt transitions from the delivery configuration to the deployed configuration.

40 Claims, 66 Drawing Sheets

(56) References Cited

U.S. PATENT DOCUMENTS

| | | |
|---|---|---|
| 7,967,769 B2 | 6/2011 | Faul et al. |
| 8,016,782 B2 | 9/2011 | Brenneman et al. |
| 8,043,360 B2 | 10/2011 | McNamara et al. |
| 8,157,860 B2 | 4/2012 | McNamara et al. |
| 8,172,896 B2 | 5/2012 | McNamara et al. |
| 8,235,933 B2 | 8/2012 | Keren et al. |
| 8,252,042 B2 | 8/2012 | McNamara et al. |
| 8,273,095 B2 | 9/2012 | Brenneman et al. |
| 8,460,372 B2 | 6/2013 | McNamara et al. |
| 8,641,724 B2 | 2/2014 | Brenneman et al. |
| 8,926,545 B2 | 1/2015 | Brenneman et al. |
| 8,932,341 B2 | 1/2015 | Brenneman |
| 9,011,362 B2 | 4/2015 | Brenneman et al. |
| 9,034,034 B2 | 5/2015 | Nitzan et al. |
| 9,067,050 B2 | 6/2015 | Gallagher et al. |
| 9,259,340 B2 | 2/2016 | Heuser et al. |
| 9,301,830 B2 | 4/2016 | Heuser et al. |
| 9,314,329 B2 | 4/2016 | Dickinson et al. |
| 9,358,371 B2 | 6/2016 | McNamara et al. |
| 9,468,441 B2 | 10/2016 | Brenneman |
| 9,550,022 B2 | 1/2017 | Brenneman et al. |
| 9,757,107 B2 | 9/2017 | McNamara et al. |
| 9,775,636 B2 | 10/2017 | Fazio et al. |
| 9,789,294 B2 | 10/2017 | Taft et al. |
| 9,820,745 B2 | 11/2017 | Brenneman et al. |
| 9,937,036 B2 | 4/2018 | Sugimoto et al. |
| 10,045,765 B2 | 8/2018 | Rafiee et al. |
| 10,111,998 B2 | 10/2018 | Brenneman et al. |
| 10,232,098 B2 | 3/2019 | Brenneman et al. |
| 10,376,680 B2 | 8/2019 | McNamara et al. |
| 10,398,421 B2 | 9/2019 | Celermajer |
| 10,463,477 B2 | 11/2019 | Forcucci et al. |
| 10,568,751 B2 | 2/2020 | McNamara |
| 10,595,999 B2 | 3/2020 | Vettukattil et al. |
| 10,624,621 B2 | 4/2020 | Celermajer |
| 10,632,292 B2 | 4/2020 | Forcucci et al. |
| 10,675,450 B2 | 6/2020 | Finch |
| 10,751,057 B2 | 8/2020 | Brenneman et al. |
| 10,926,068 B2 | 2/2021 | Narayan et al. |
| 10,932,786 B2 | 3/2021 | McNamara et al. |
| 10,993,735 B2 | 5/2021 | Vardi et al. |
| 11,090,177 B2 | 8/2021 | Reis et al. |
| 11,135,410 B2 | 10/2021 | Finch et al. |
| 11,160,961 B2 | 11/2021 | Fahey et al. |
| 11,253,685 B2 | 2/2022 | Fahey et al. |
| 11,259,789 B2 | 3/2022 | Rowe et al. |
| 11,717,429 B2 | 8/2023 | Schwartz et al. |
| 11,752,314 B2 | 9/2023 | Taft et al. |
| 2001/0044631 A1 | 11/2001 | Akin et al. |
| 2006/0247761 A1 | 11/2006 | Greenberg et al. |
| 2008/0241215 A1 | 10/2008 | Falotico et al. |
| 2010/0016833 A1 | 1/2010 | Ogle et al. |
| 2010/0057096 A1 | 3/2010 | Wolf |
| 2010/0268316 A1* | 10/2010 | Brenneman .......... A61B 17/083 604/8 |
| 2020/0085600 A1 | 3/2020 | Schwartz et al. |
| 2021/0275177 A1* | 9/2021 | Binmoeller ......... A61B 17/1114 |
| 2022/0031327 A1 | 2/2022 | Manash et al. |
| 2022/0125430 A1 | 4/2022 | Rafiee et al. |
| 2022/0257904 A1 | 8/2022 | Passman et al. |
| 2022/0273312 A1 | 9/2022 | Goldsmith |
| 2023/0329753 A1 | 10/2023 | Chang |
| 2024/0252793 A1 | 8/2024 | Kuhn et al. |

OTHER PUBLICATIONS

Non-Final Office Action in U.S. Appl. No. 18/634,734, mailed Sep. 11, 2024, 7 pages.

* cited by examiner

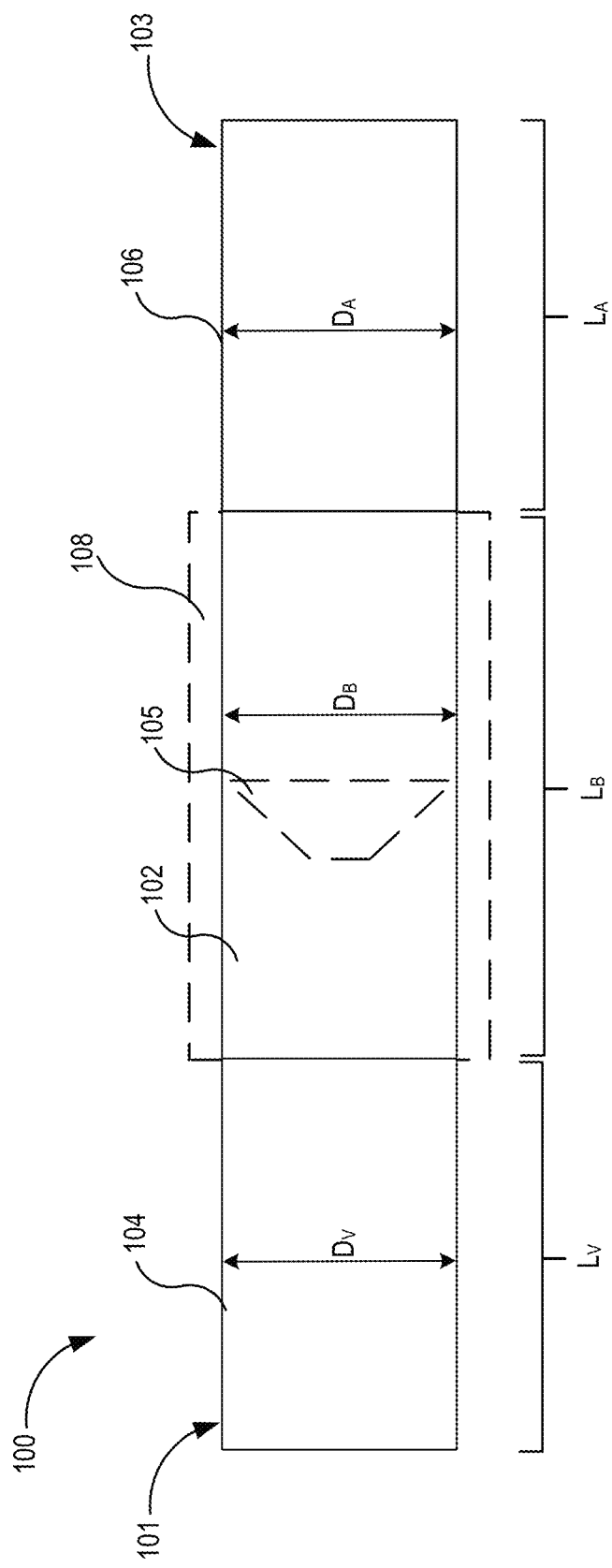

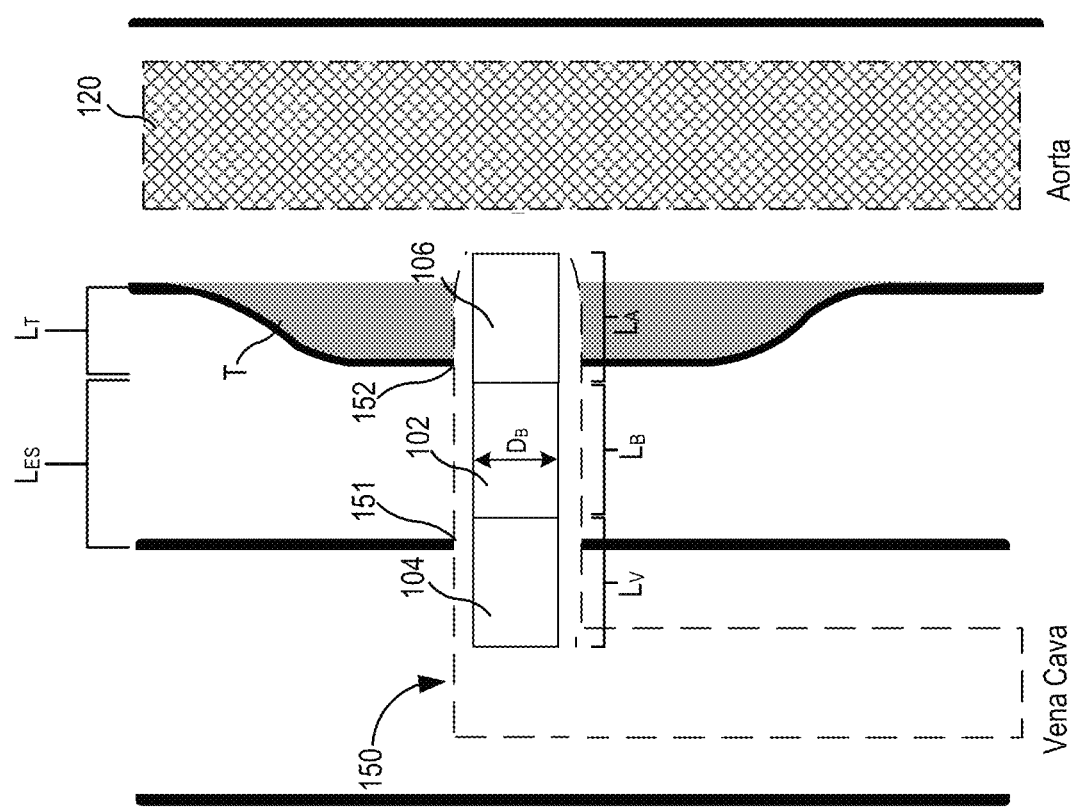

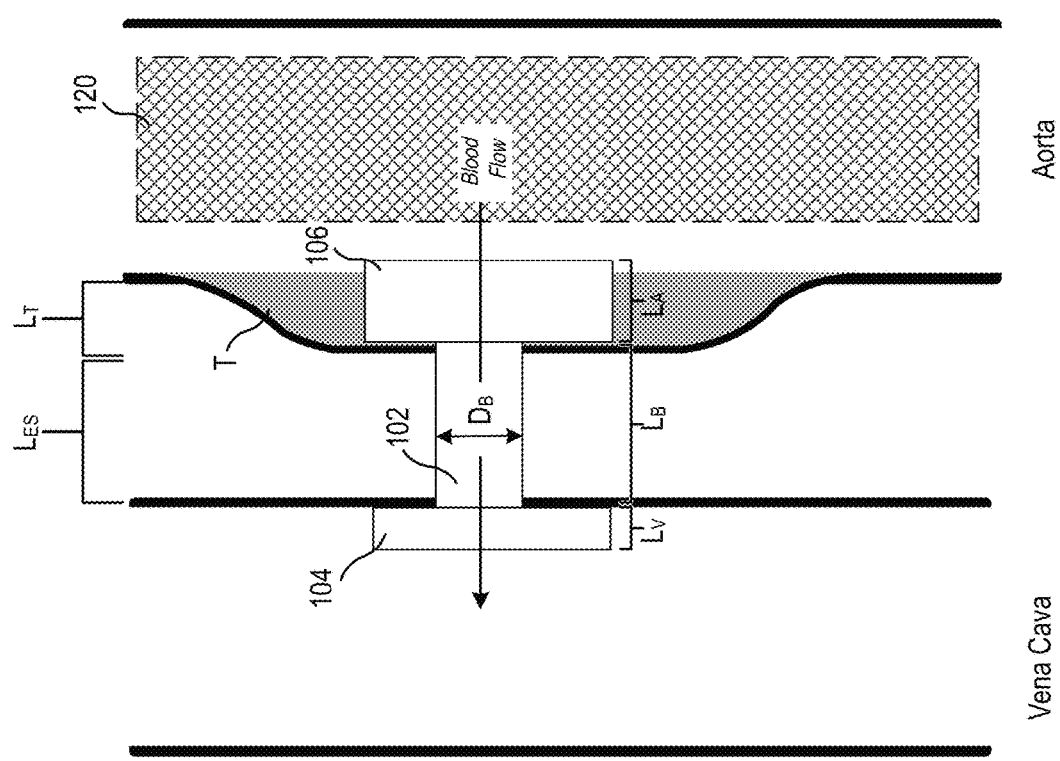

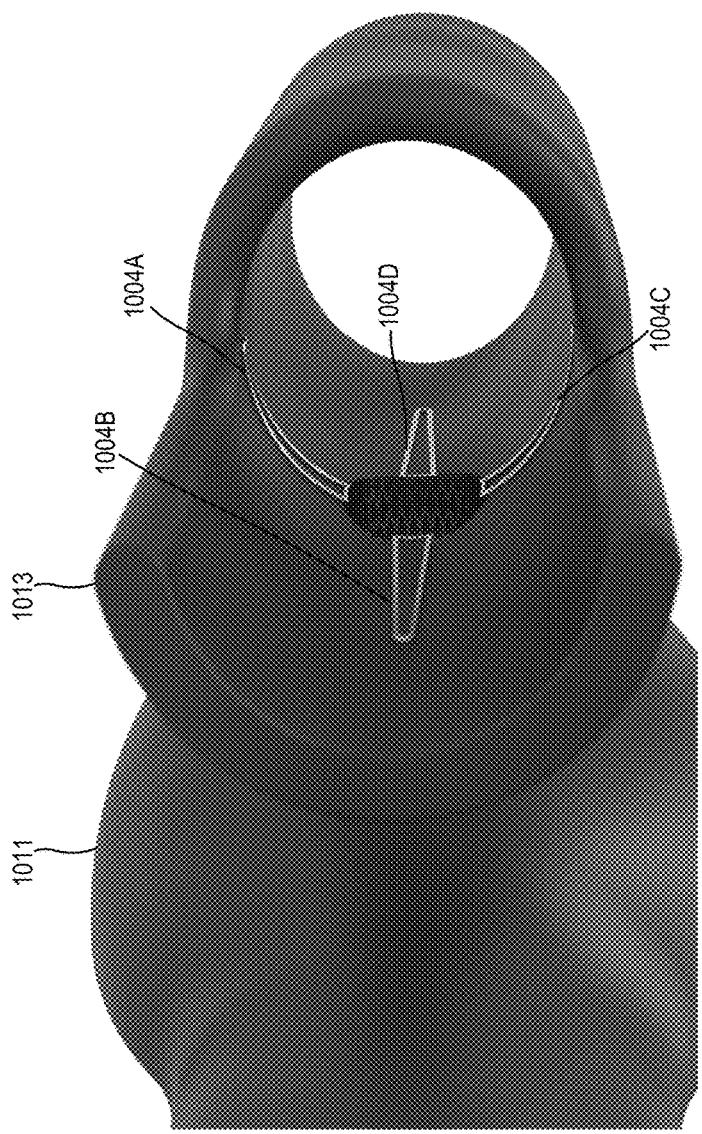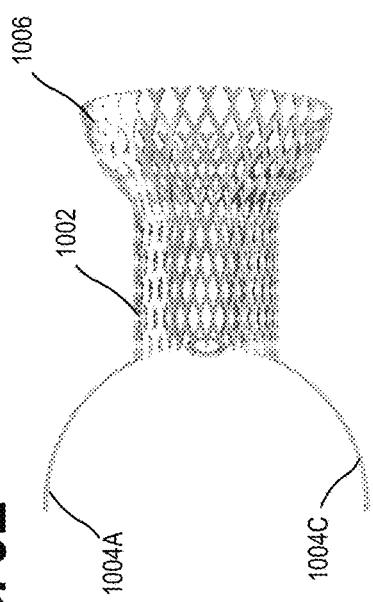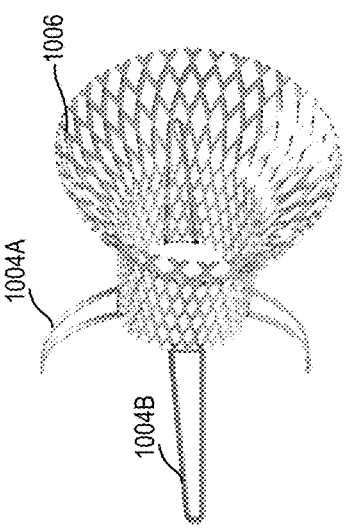
FIG. 9E
FIG. 9F
FIG. 9G

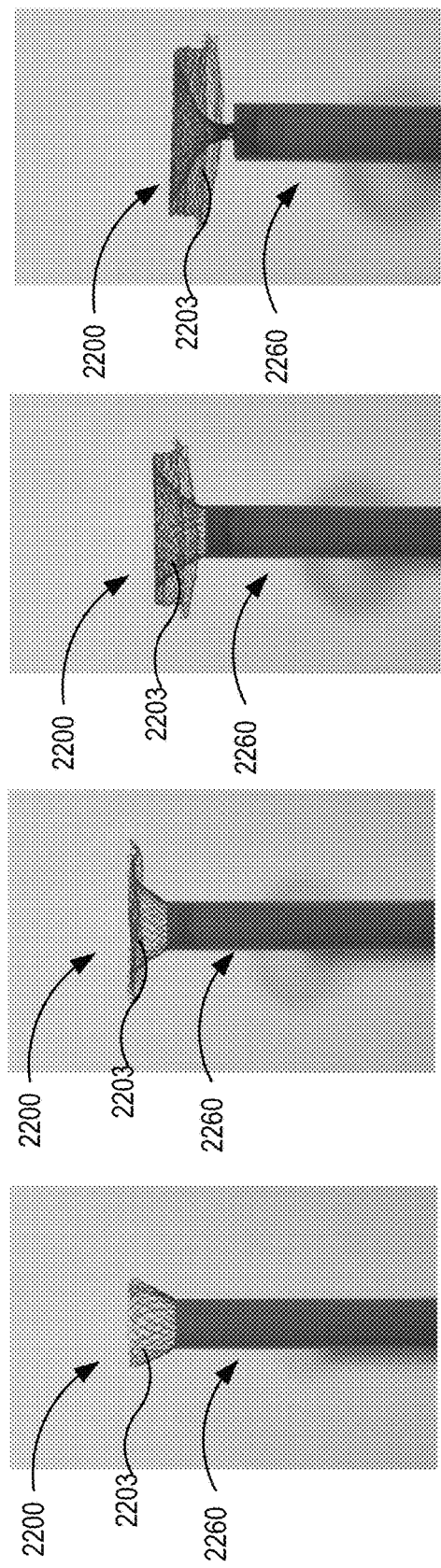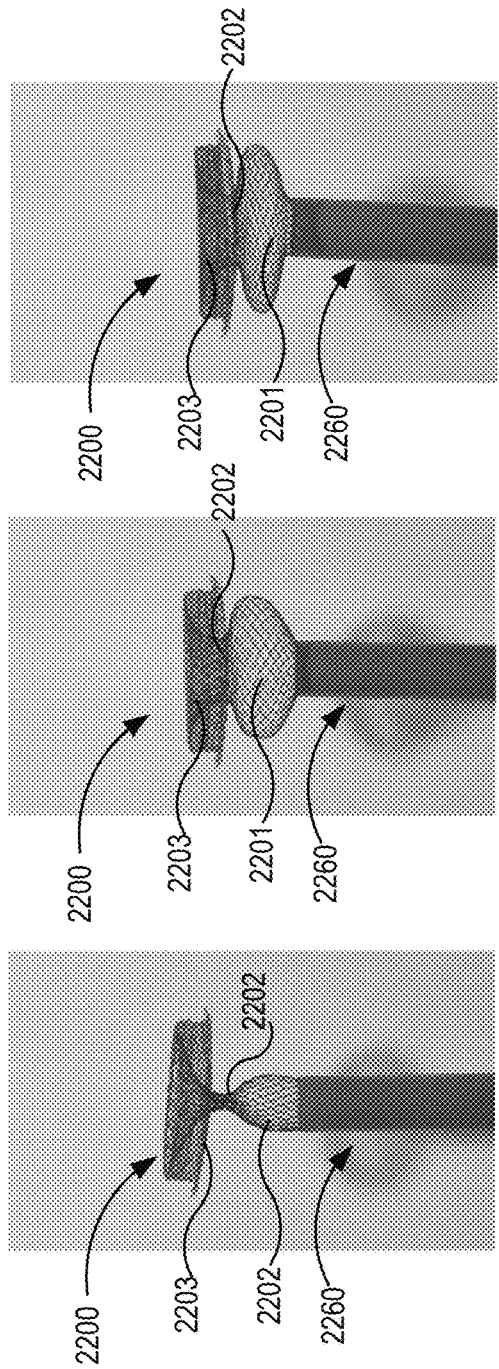

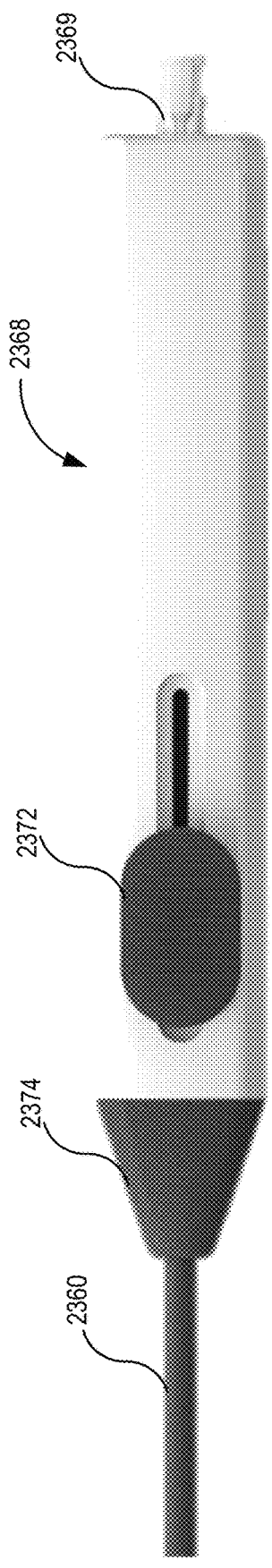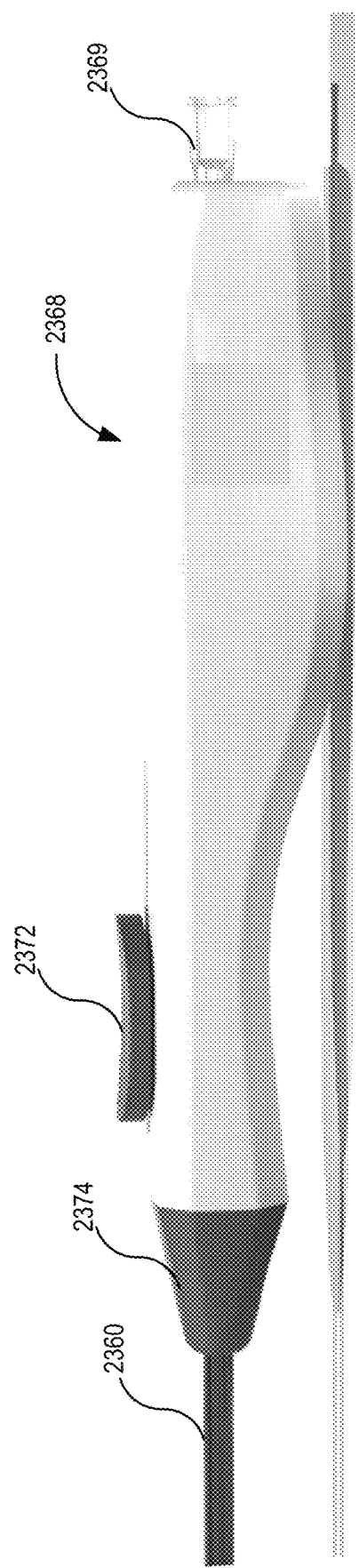
FIG. 44A
FIG. 44B

METHODS AND SYSTEMS FOR TRANSCAVAL TREATMENT OF ANEURYSMS

CROSS REFERENCE TO RELATED APPLICATIONS

This application is a continuation-in-part of U.S. application Ser. No. 18/419,262, filed Jan. 22, 2024, entitled "Methods and Systems for Transcaval Treatment of Aneurysms" and claims priority to U.S. Provisional Application No. 63/675,198, filed Jul. 24, 2024, entitled "Self-Adjusting Shunts and Methods and Systems for Using the Same", the contents of each of which is hereby incorporated by reference herein in its entirety.

TECHNICAL FIELD

Embodiments described herein relate to self-adjusting shunts and methods and systems for using and delivering the same.

BACKGROUND

Shunts can be used to treat a variety of conditions including cardiac conditions (e.g., heart failure), peripheral vascular disease (PVD), portal hypertension, traumatic injuries, and aneurysms, for example. Tissue defects within blood vessels, such as aneurysms (e.g., aortic aneurysms and brain aneurysms) can lead to pain, stroke, and/or eventual ruptures in the vessel. Existing shunts have drawbacks associated with treating different conditions such as, for example, lack of adaptability and flexibility, difficult deployment, issues with anchoring (e.g., thereby causing leaks), and invasiveness.

SUMMARY

In some embodiments, a method of preventing or relieving endotension in an aortic aneurysm in a subject includes puncturing a vein to define a venous puncture site; puncturing an artery via the venous puncture site to define an arterial puncture site; after the puncturing the artery, delivering an endograft to the aortic aneurysm; and after the puncturing the artery, creating a fluid passageway between the venous puncture site and the arterial puncture site to permit blood flow therethrough from the artery to the vein.

In some embodiments, a method of treating an aortic aneurysm of an artery in a subject having an endograft implanted within the aortic aneurysm, includes puncturing a vein to define a venous puncture site; puncturing an artery via the venous puncture site to define an arterial puncture site; and after the puncturing the artery, delivering a shunt through the venous puncture site towards and through the arterial puncture site, thereby enabling blood flow from the endoleak through a lumen defined by the shunt from the artery to the vein In some embodiments, a method of treating an endoleak associated with an endograft implanted within an aortic aneurysm of an artery in a subject, includes selecting a shunt based on a lateral thickness of a thrombus formed in an aortic aneurysm determined by imaging of the aortic aneurysm, the shunt defining a body and having an arterial sealing structure at a first end of the body and a venous sealing structure a second, opposite end of the body, a lateral length of the arterial sealing structure being greater than or equal to the lateral thickness of the thrombus; advancing the shunt in a delivery configuration through a venous puncture site of a vein to access an arterial puncture site of the artery; and transitioning the shunt from the delivery configuration to a deployed configuration to secure the shunt to the artery and the vein, thereby enabling blood flow through the body of the shunt from the artery to the vein.

In some embodiments, an apparatus for treating an endoleak includes a shunt defining a central portion and having an arterial sealing structure at a first end of the central portion and a venous sealing structure a second, opposite end of the central portion, the arterial sealing structure and the venous sealing structure both being expandable from a delivery configuration to a deployed configuration, the venous sealing structure having a lateral length in its deployed configuration, the arterial sealing structure having a lateral length in its deployed configuration that is greater than the lateral length of the venous sealing structure.

In some embodiments, a cutting apparatus includes a proximal member and a distal member movably coupled to the proximal member to allow for relative axial movement between a first configuration in which the proximal member and the distal member are spaced a distance sufficient to span across a venous wall of a vein and an arterial wall of an artery, and a second configuration in which the proximal member and the distal member are spaced less than a thickness of at least one of the venous wall or the arterial wall, one of the proximal member or the distal member having a cutting edge configured to cut through the venous wall and the arterial wall.

In some embodiments, an apparatus for treating an endoleak includes a shunt defining a body and having an arterial sealing structure at a first end of the body and a venous sealing structure a second, opposite end of the body, the arterial sealing structure and the venous sealing structure both being expandable from a delivery configuration to a deployed configuration, the body having a fluid porosity that is less than a fluid porosity of both the arterial sealing structure and the venous sealing structure.

BRIEF DESCRIPTION OF THE DRAWINGS

FIG. 1A is a schematic block diagram of a shunt for treating or alleviating an aortic aneurysm in a delivery configuration, according to an embodiment.

FIGS. 2A-2C are schematic block diagrams depicting placement of the shunt of FIGS. 1A-1B to connect a vena cava and an aorta of a patient to treat an endoleak, according to an embodiment.

FIGS. 9A-9G are illustrations of the shunt disposed between an artery and a vein to place the artery in fluid communication with the vein to treat an aortic aneurysm, according to an embodiment.

FIGS. 43A-43G are images of a self-rolling shunt transitioning from a delivery configuration to a deployed configuration, according to embodiments.

FIGS. 44A-44C show a handle for a delivery system for delivering a shunt, according to embodiments.

DETAILED DESCRIPTION

Figure 1B:
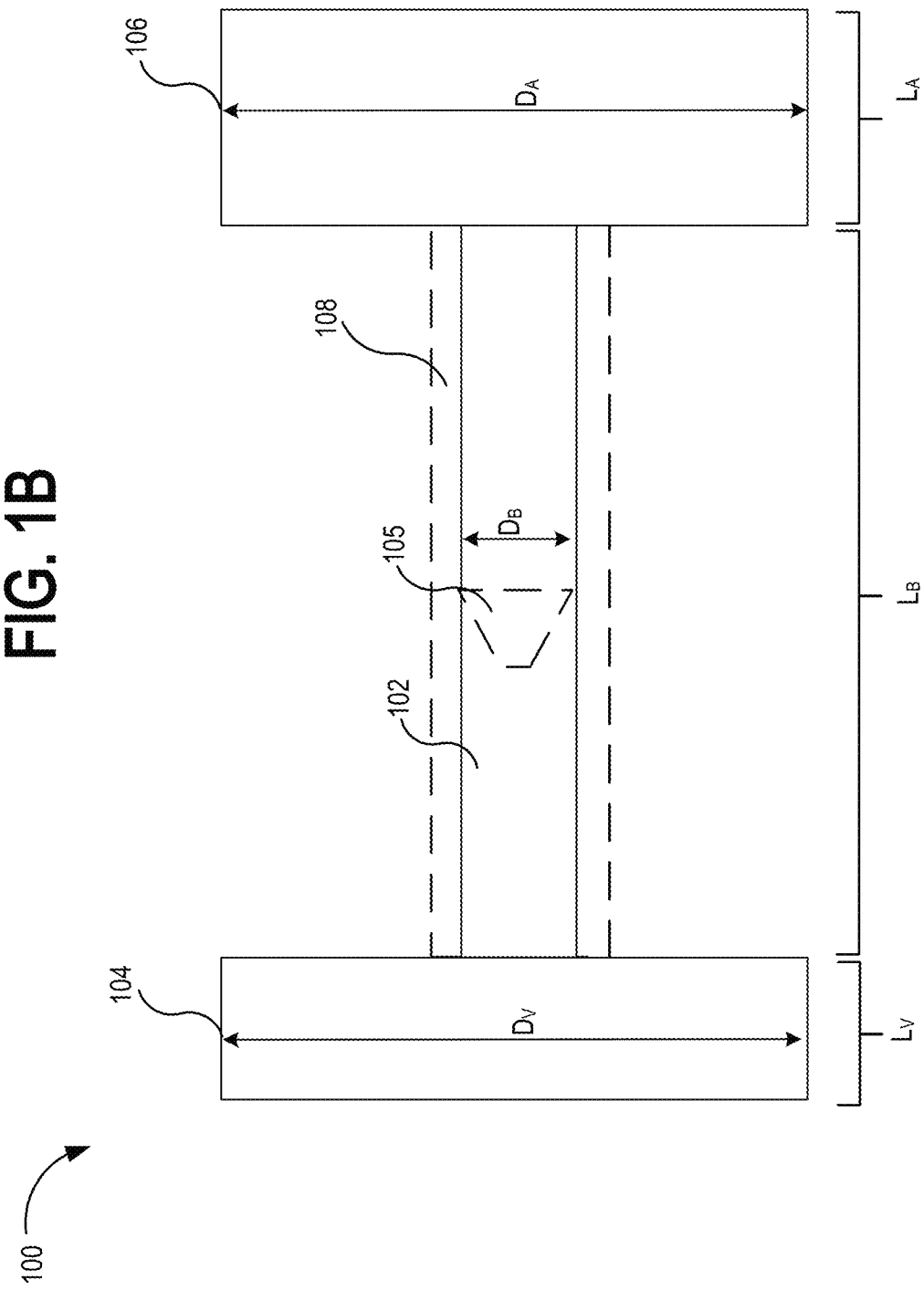
FIG. 1B is a schematic block diagram of the shunt for treating or alleviating an aortic aneurysm in a deployed configuration, according to an embodiment.

Aneurysms occur when there is a weakening in the wall of the blood vessel leading to a widening, opening or formation of a cavity within the vessel wall. The opening of such a cavity can be further exasperated by the continual pooling of blood in the cavity, thereby pressurizing the already weakened vessel wall. Such a damaged vessel, which can be age-related, drug or tobacco-induced, resulting from atherosclerosis or in some instances, caused by infection, can result in a vessel rupture, which can lead to life-threatening internal bleeding.

An abdominal aortic aneurysm is an aneurysm in the abdominal portion of the aorta usually located in or near one or both of the two iliac arteries or near the renal arteries. The aneurysm often arises in the infrarenal portion of the diseased aorta, for example, below the kidneys. The occurrence of aneurysms is not confined to the abdominal region. While abdominal aortic aneurysms are generally the most common, aneurysms in other regions of the aorta or one of its branches are possible. For example, a thoracic aortic aneurysm is an aneurysm in the thoracic portion of the aorta. When left untreated, the aneurysm may rupture, usually causing rapid fatal hemorrhaging. A ruptured abdominal aortic aneurysm is presently the thirteenth leading cause of death in the United States. Aortic aneurysms often cause an enlarged area in portion of the aorta in which they are located (e.g., aneurysm sac).

Endovascular Aortic Aneurysm Repair (EVAR) is a procedure in which a stent-graft prosthesis (hereinafter, 'endograft') is deployed endovascularly to treat an aneurysm, while leaving the aneurysm sac in place. Endografts have been developed to place exclusion devices within or across an opening or cavity associated with the subject tissue defect to preserve blood flow through the damaged blood vessel (e.g., where the aneurysm sac is located) and prevent blood from further pressurizing the damaged vascular tissue. EVAR may be favored over open surgical repair of aneurysms in order to, for example, shorten operation, intensive care, and total hospital times and lower postoperative morbidity. Although EVAR has become a viable alternative to open repair for a significant percentage of abdominal aortic aneurysm patients, the varying shapes, locations, sizes, and other features associated with an abnormal or unhealthy aorta can prevent proper alignment and/or sealing of the endograft with the vessel wall/tissue. As a result, EVAR requires long-term postoperative surveillance to detect complications such as endoleaks, endograft migration, endograft fracture, and aortic neck dilation. Endoleak remains the most severe complication of EVAR and may result in life-threatening sac enlargement and aneurysm rupture if a patient does not receive imaging on a regular basis to detect possible complications. Endoleak occurs in up to 50% of all EVAR cases. Almost 30% of patients require reintervention within 5 years after EVAR due to endoleaks causing aneurysm sac enlargement.

Endoleaks, of which there are 5 different types, involve blood flow within the aneurysm sac and outside the endograft lumen and can lead to an increased risk of aneurysmal expansion and rupture. A Type I endoleak occurs when blood flows between the endograft and the blood vessel wall; typically at the proximal (often renal) or distal (often iliac) end of the endograft. This complication may also occur as a result of movement of the endograft away from the desired location, sometimes called migration. Type II endoleaks occur when blood flows backwards (retrograde) into the aneurysm sac from arteries originating from the aneurysm sac itself (typically the lumbar, testicular or inferior mesenteric arteries). Type III endoleaks occur when blood leaks between the junction sites of "articulated" or "segmented" endografts; these multi-component endografts are inserted as separate segments which are then assembled inside the artery into their final configuration. Detecting and confirming accurate assembly and fluid-tight contact between the different segments is difficult and current verification methods of correct assembly are suboptimal. Type IV endoleaks occur when cracks or defects develop in the endograft fabric and blood is able to leak directly through the graft material. Lastly, Type V endoleaks are leakage of blood into the aneurysm sac of an unknown origin. Regardless of their cause, endoleaks are frequently a medical emergency and early detection, characterization and monitoring of them is an important unmet medical need. Incidence rates vary from 15% to 52%, and most patients require either a surgical or endovascular intervention.

The origin of the leak defines the type of endoleak, but all or most types of endoleaks are typically monitored with long term surveillance or addressed with subsequent surgical procedures. New endoleaks may develop as long as several years post-procedure, which necessitates long term patient screening. As more patients are opting for EVAR, there is a strain on healthcare systems to cover the cost. Long-term surveillance, imaging studies, and reintervention have been shown to increase the global cost of EVAR by nearly 50%. According to recent meta-analyses, EVAR has a 56% greater intermediate reintervention rate and 243% greater long-term reintervention rate when compared to open surgical repair. Despite more compliant stent-graft technology and more surgical experience, EVAR remains less durable than open repair. Long-term durability of EVAR suffers due to endoleak development, graft migration, and continued sac pressurization, all of which may result in sac rupture. Despite new technology for stent-grafts, the amount of people who develop endoleaks has not significantly decreased, partly as a result of endografts being implanted outside of their instructions for use (IFU) and the inability to effectively prevent type II endoleaks.

Embodiments described herein help prevent or mitigate endoleaks and may liberalize the IFU for stent-grafts, reduce EVAR complications related to endoleak, and reduce the amount of stringent post-EVAR imaging. The embodiments described herein may have a positive impact economically, physically, and mentally on patients due to increased EVAR durability and reduced monitoring. Accordingly, embodiments that reduce the development and severity of endoleaks will improve cost effectiveness and durability of EVAR.

Type I (T1) and type III (T3) endoleaks have been treated by coil embolization, angioplasty, additional endografts, or glue embolization. However, management for type II (T2) endoleaks remains controversial despite being the most common type of endoleak. Unlike T1 and T3 endoleaks, T2 endoleaks can spontaneously resolve and their relationship to aneurysm sac enlargement and pressurization are uncertain. There is a consensus, however, that persistent T2 endoleaks (>6 months) are associated with aneurysm sac growth, reintervention, conversion to open repair, and rupture. Furthermore, the detection and embolization of T2 endoleaks is difficult due to the size of feeding vessels. As a result of inadequate detection of endoleaks and the ability of endoleaks to resolve then reappear, patients are monitored yearly. Regardless of the type of endoleak, embodiments address a clinical need to make EVAR more durable and to exclude the aneurysm from systemic circulation. Prophylactic embodiments may reduce the need for long-term surveillance, prevent endograft migration via biological fixation, and mitigate endoleak formation.

The risk of aneurysm rupture is related to aneurysm size, with large aneurysms more likely to rupture than small aneurysms. Due to the risks of early repair, most patients with abdominal aortic aneurysms (AAAs) are only eligible for treatment when their aneurysms have progressed to the point of imminent rupture. There is no solution to prevent disease progression when AAAs are at a relatively harmless stage (smaller than ~5 cm). These patients are under "active surveillance" (annual or semi-annual imaging protocols), tracking their aneurysm's growth until it reaches a large enough threshold for treatment. In the meantime, these patients are living their lives knowing they have up to an 8% risk of rupture.

There are an estimated 13 million people worldwide currently living with an abdominal aortic aneurysm. When left untreated, all AAAs will eventually rupture if a patient lives long enough. A ruptured AAA is associated with up to a 90% mortality rate and is a contributing factor for 2% of all deaths. AAAs are estimated to cause over 200,000 deaths every year worldwide. With a rapidly growing worldwide population of elderly patients with a significantly higher risk of developing aortic aneurysms, there is a need for solutions to improve the standard of care of endovascular aortic aneurysm repair.

In some embodiments, the methods and systems disclosed and described herein are useful to treat aneurysms after a patient has undergone an EVAR procedure and requires additional treatment to alleviate the aneurysm and/or reduce endotension. In some embodiments, the methods and systems disclosed and described herein are useful to treat, repair, and/or prevent endoleaks and/or endotension after, during, and/or before a patient has undergone an EVAR procedure. In some embodiments, the methods and systems disclosed and described herein are useful to treat aneurysms by alleviating blood pressure at a target vascular site. In some embodiments, the methods and systems disclosed and described herein are useful to reduce the severity, frequency, and/or duration of adverse events related to the treatment of aortic aneurysms.

In some embodiments, treating aortic aneurysms helps prevent an aneurysm rupture, reduce an aneurysm size (e.g., aneurysm sac size), alleviates hypertension within the aneurysm, or any combination thereof.

There have been several case studies showing the presence of an aortocaval fistula providing immediate benefit to patients after EVAR by shunting blood from the aneurysm sac to the inferior vena cava, resulting in rapid shrinkage of AAAs despite persistent endoleaks. Accordingly, a device configured for creating a fluid connection between the inferior vena cava and the sac of an abdominal aortic aneurysm would provide a safe and effective alternate means of improving post-procedural outcomes following endovascular aortic aneurysm repair. Transcaval access provides an improved access route for endovascular aortic interventions in aortic interventions, particularly for patients unsuitable for traditional access routes including femoral, subclavian, transapical, and aortic. This approach involves percutaneous advancement of a guidewire into the abdominal aorta via initial access from the femoral vein through the adjoining inferior vena cava.

In some embodiments, treating aortic aneurysms comprises relieving pressure build-up and/or reducing blood flow through the impacted region experiencing the aneurysm. In some embodiments, a shunt (e.g., transcaval shunt) is implanted from an adjacent vein (e.g., vena cava) and passed through an aortic wall so as to allow blood to flow from the artery (e.g., abdominal aorta) to the vein (e.g., vena cava). In some embodiments, the shunt is used to help alleviate, reduce, eliminate, and/or prevent fluid build-up resulting from one or more endoleaks. In alternate or additional embodiments, a bypass graft may be implanted so as to bypass all or some of the blood flow around the aneurysm (e.g., aneurysm sac). In some embodiments, systems and methods described herein are used to treat an aortic aneurysm after a subject has undergone an EVAR procedure to implant a stent-graft prosthesis (e.g., endograft).

Disclosed herein, in some aspects, is a method of treating or alleviating an aortic aneurysm in a subject, the method including advancing a shunt through a venous puncture site of a vein to access an arterial puncture site of an artery, the arterial puncture site disposed within the aortic aneurysm or upstream of the aortic aneurysm; and securing the shunt to the artery and vein by deploying i) an arterial sealing structure coupled to a distal end of the shunt, and ii) deploying a venous sealing structure coupled to a proximal end of the shunt, thereby enabling fluid to flow from the artery to the vein. In some embodiments, advancing the shunt occurs contemporaneous or substantially contemporaneous with an implantation of an endograft within the aortic aneurysm. In some embodiments, advancing the shunt occurs after an implantation of an endograft within the aortic aneurysm. In some embodiments, advancing the shunt includes inserting a catheter within the vein, the catheter being steerable via a catheter handle coupled thereto; and extending a sliding sheath from the catheter, the sliding sheath detachably coupled to the shunt.

In some embodiments, securing one or both of the arterial sealing structure and the venous sealing structure comprises withdrawing the sliding sheath away from the artery. In some embodiments, one or both of the arterial sealing structure and the venous sealing structure are self-expandable. In some embodiments, the aortic aneurysm is an abdominal aortic aneurysm. In some embodiments, one or both of the arterial and venous sealing structures are pivotally attached to the shunt. In some embodiments, the shunt comprises a shunt body made of a compliant material capable of stretching and shrinking. In some embodiments, the shunt body includes a lumen therein so as to enable the fluid to flow from the artery to the vein.

Disclosed herein, in some aspects, is a method of treating an aortic aneurysm in a subject, the method including implanting a graft within a subject to at least partially bypass a fluid flow through an artery around the aortic aneurysm, the graft having a lumen therein. In some embodiments, the graft is fluidly coupled to the artery at i) a first location upstream of the aortic aneurysm to receive the fluid, and ii) a second location downstream of the aortic aneurysm to deliver the fluid back to the artery. In some embodiments, the graft passes through a portion of a vein. In some embodiments, implanting the graft includes inserting a catheter within the artery; passing the artery through the second location of the artery to exit the artery; advancing the catheter to the first location of the artery; passing the catheter through the first location; advancing the graft over the catheter; deploying a first sealing structure to secure and seal the graft at the first location; deploying a second sealing structure to secure and seal the graft at the second location; and withdrawing the catheter. In some embodiments, one or both of the first and second sealing structures are self-expandable.

Disclosed herein, is a shunt that includes a self-adjusting mechanism (e.g., a self-sizing, self-rolling, etc.). In some embodiments, a distal end and/or a proximal end of the shunt may be configured to roll and/or unroll during and/or after deployment of the shunt such that a total length of the shunt is adjustable during and/or after deployment. Therefore, the total length of the shunt may be adjusted to accommodate changes in anatomy (e.g., a space between vessels increasing and/or decreasing after deployment). In some embodiments, the distal end of the shunt may roll to form a toroidal structure, and the toroidal structure may act as an anchor to stabilize the shunt. In some embodiments, one end (e.g., proximal end) of the shunt maybe roll to form a toroidal structure and another end (e.g., distal end) of the shunt may form a different structure, e.g., a sealing structure (e.g., a bulb-like shape, a cone, a disc-like shape, a flared structure, etc.) to seal any openings around the shunt in the vessel (or other anatomy) to prevent leakage of blood into the extravascular space after deployment.

In some embodiments, a shunt may include a first end, a second end, and a central portion therebetween, and the shunt can be configured to transition between a delivery configuration in which the shunt is cylindrical and a deployed configuration in which the second end of the shunt has rolled to form a toroidal structure and to decrease a total length of the shunt. In some embodiments, the first end of the shunt may be the proximal end and the second end of the shunt may be the distal end. In some embodiments, the second end of the shunt may form a toroidal structure when the second end rolls towards the central portion, and the toroidal structure may be configured to anchor the shunt relative to a vessel. In some embodiments, the first end may expand radially to form a disc shape when the shunt transitions from the delivery configuration to the deployed configuration. In some embodiments, the shunt may be configured to dynamically adjust the total length of the shunt by further rolling or unrolling the toroidal structure based on changes in anatomic structure or pressure conditions. In some embodiments, the shunt may be coupled to a delivery catheter configured to constrain the shunt in the delivery configuration and to release the shunt to transition the shunt to the deployed configuration. In some embodiments, the shunt can include at least one radiopaque marker.

In some embodiments, a shunt may include a first end, a second end, and a central portion therebetween, and the shunt may be configured to transition between a delivery configuration in which the shunt is cylindrical and a deployed configuration in which the second end of the shunt has rolled to form a ring-like structure and to decrease a total length of the shunt. In some embodiments, a shunt may include a first end, a second end, and a central portion therebetween, and the shunt may be configured to, upon expansion, invert at least a portion of the second end outwardly so that at least a portion of the second end is directed towards the first end.

In some embodiments, a stent may include a proximal end, a distal end, and a central portion extending therebetween, and the stent may be configured to transition from a compressed delivery configuration to a deployed configuration. The distal end of the stent may be configured to invert towards the proximal end upon deployment such that the inner surface of the distal end faces outwardly to create an anchoring structure. In some embodiments, a vascular stent may include inversion capabilities. In some embodiments, a tubular stent body may include a proximal end, a distal end, and a central portion, and at least a portion of the distal end may be configured to invert outwardly towards the central portion upon deployment, resulting in an outwardly facing inner surface.

The self-adjusting shunt may be used for a variety of applications including, for example, interatrial shunts, hemodialysis access, peripheral vascular disease, congenital heart defects, portal hypertension, traumatic injuries, cerebral arteriovenous malformations, coronary artery disease, pulmonary hypertension, cancer treatment, venous insufficiency, transcaval shunting for abdominal aortic aneurysm, research and experimental therapies, etc. For these applications, the self-adjusting shunt may provide an adaptable, versatile, minimally invasive, and durable solution.

FIGS. 1A-1B are schematic block diagrams of an implantable device (e.g., a shunt) 100 for treating or aiding in the treatment of an aortic aneurysm in a delivery configuration and a deployed configuration, respectively, according to an embodiment. The shunt 100 may include a central portion 102 defining a central lumen, a proximal end 101, and a distal end 103. The proximal end 101 of the shunt 100 may include a venous sealing structure 104, and the distal end 103 of the shunt 100 may include an arterial sealing structure 106. The shunt 100 may optionally include (1) a coating or cover 108 disposed around the central portion 102 and/or (2) a flow controller 105 disposed in the central lumen. In the delivery configuration (e.g., the biased or compressed configuration), the shunt 100 may form a substantially cylindrical shape (e.g., a uniform cylindrical shape) such that the shunt 100 may move through a catheter of a delivery system (not shown) and/or a blood vessel. In some embodiments, the central lumen of the shunt 100 may have a diameter (inner diameter of the central portion 102 corresponding to a cross-sectional area of the central portion 102) $D_B$, the venous sealing structure may have a diameter (inner diameter corresponding to a cross-sectional area of the venous sealing structure) $D_V$, and the arterial sealing structure may have a diameter (inner diameter corresponding to a cross-sectional area of the arterial sealing structure) $D_A$. In some embodiments, in the delivery configuration, a diameter of the shunt 100 may be constant across a length of the shunt 100 (e.g., $D_B$, $D_V$, and $D_A$ may all be equivalent or substantially equivalent) or the diameter of the shunt 100 may have little variation (e.g., less than 5%) across the length of the shunt 100. In some embodiments, the central portion 102 of the shunt 100 is attached to the arterial sealing structure 106 and venous sealing structure 104 via an arterial sealing structure attachment and venous sealing structure attachment, respectively.

In some embodiments, the diameters of the central lumen $D_B$, the arterial sealing structure $D_A$, and the venous sealing structure $D_V$ in the delivery configuration may be in a range of about 1 mm to about 5 mm, inclusive of all ranges and subranges therebetween. In some embodiments, the length $L_B$ of the central portion 102 (and therefore the central lumen) in the delivery configuration may be in a range of about 1 mm to about 50 mm, inclusive of all ranges and subranges therebetween. In some embodiments, the length $L_A$ of the arterial sealing structure 106 in the delivery configuration may be in a range of about 1 mm to about 50 mm, inclusive of all ranges and subranges therebetween. In some embodiments, the length $L_V$ of the venous sealing structure 104 in the delivery configuration may be in a range of about 1 mm to about 50 mm, inclusive of all ranges and subranges therebetween.

In some embodiments, the shunt 100 may be implanted in a body of the patient to place the sac of an aortic aneurysm in fluid communication with a region of lower pressure. For example, the shunt 100 may be implanted to place an aorta of the patient in fluid communication with the vena cava of the patient. The lower pressure passage (e.g., the vena cava) may decrease the arterial resistance and reduce pressure within the aneurysm because blood may preferentially flow down the pressure gradient to the lower pressure passage. In this way, the shunt 100 may be implanted to alleviate pressure within an aortic aneurysm, prevent progression of an aortic aneurysm, and/or drain or remove fluid within the aneurysm sac (e.g., build-up fluid resulting from an endoleak). Treating aortic aneurysms may help prevent an aneurysm rupture, reduce an aneurysm size (e.g., aneurysm sac size), alleviate hypertension within the aneurysm, or any combination thereof.

Figure 4:
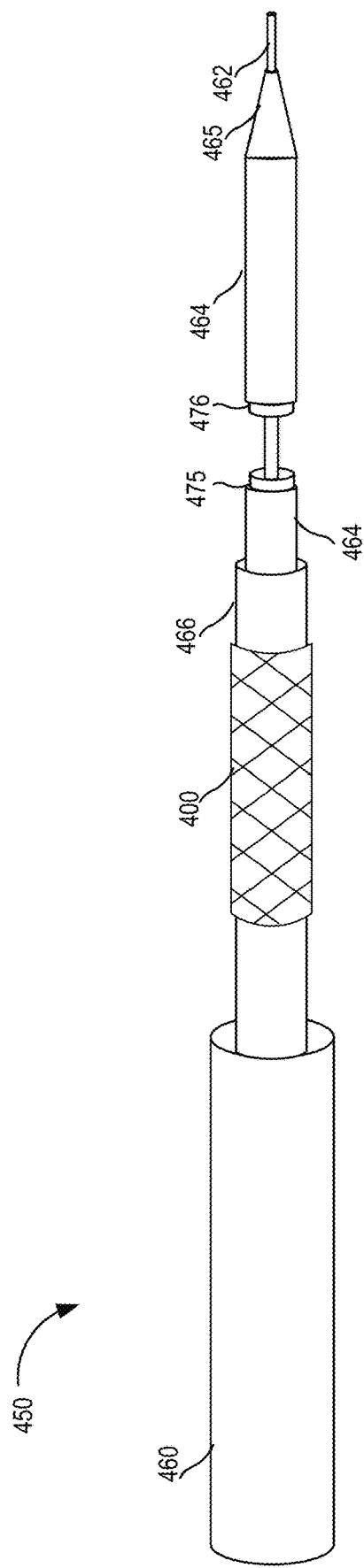
FIG. 4 is a schematic block diagram of a distal end of a delivery system of the shunt, according to an embodiment.
Figure 10A:
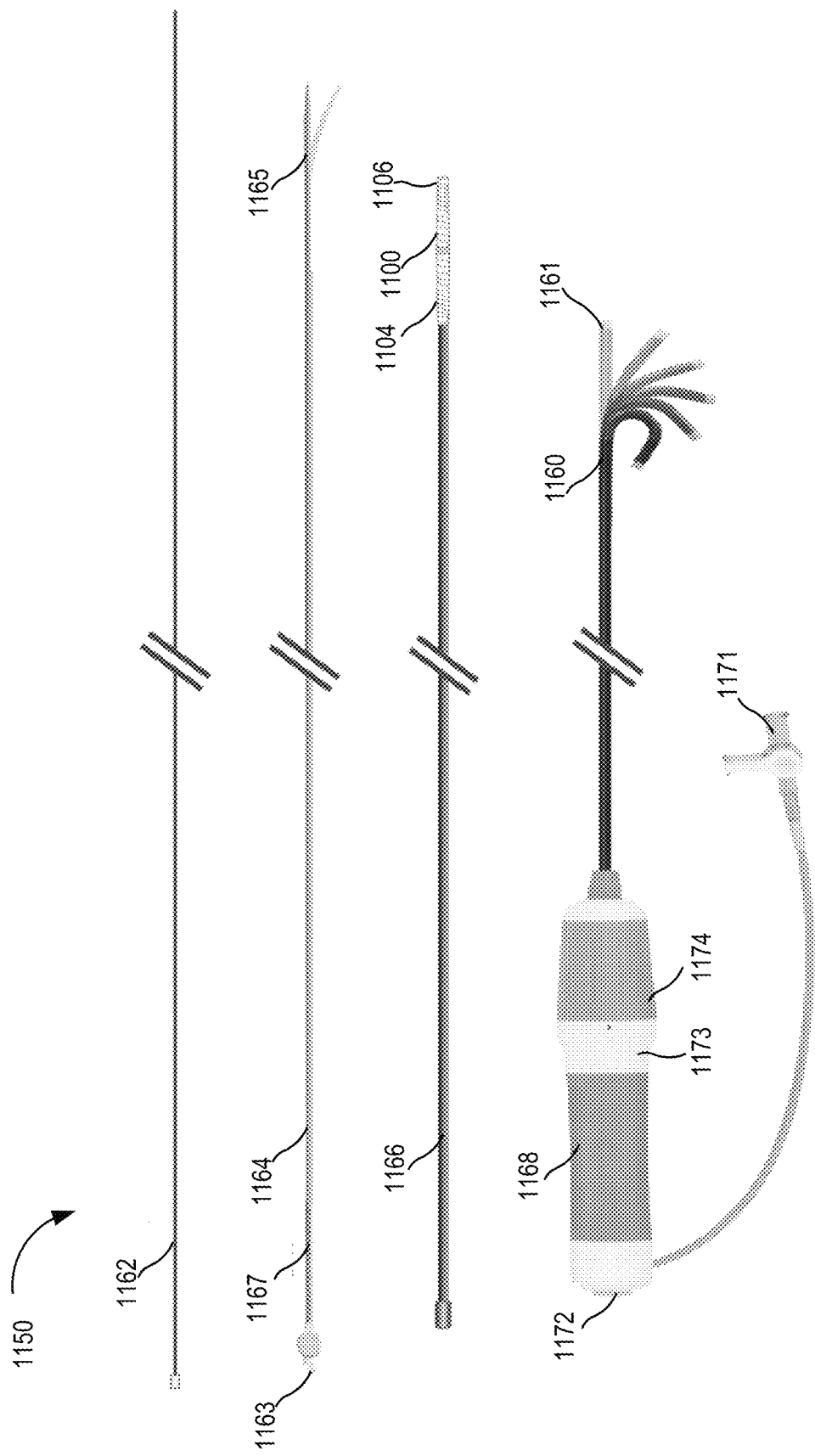
FIGS. 10A-10B show the delivery system including a guidewire, dilator, sliding sheath, catheter, and handle for delivering the shunt to treat or alleviate an aortic aneurysm, according to an embodiment.
Figure 10B:
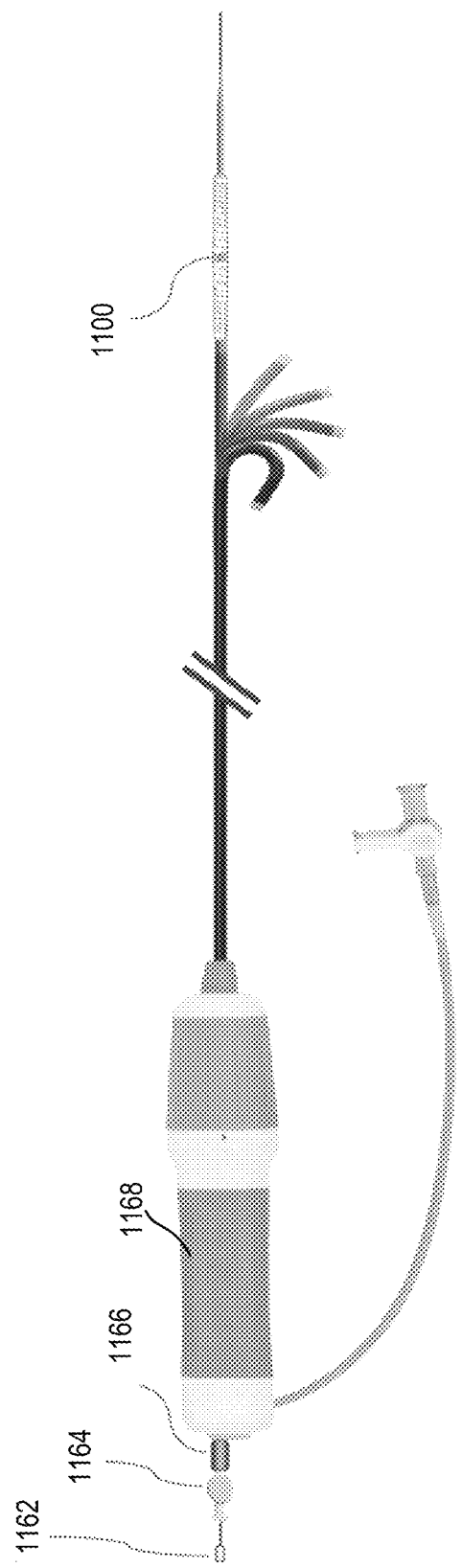

In order to implant the shunt 100, a delivery system including a guidewire and a catheter may be navigated through the vena cava until a target location corresponding to the aortic aneurysm is reached, described in further detail with respect to FIG. 4 and FIGS. 10A-10B. Then a distal end of the delivery system may be positioned perpendicular (or nearly perpendicular) to a wall of the vena cava. The distal end of the delivery system may include a needle configured to create a venous puncture site in the wall of the vena cava and to create an arterial puncture site in a wall of the aorta. Additionally or alternatively, the guidewire may be used to perform vessel puncture. In some embodiments, electrocautery may be applied while puncturing the vessels to seal the tissue near and/or at the puncture site. The delivery system may then advance the distal end 103 of the shunt 100 distally through the venous puncture site, across an extravascular space, and through the arterial puncture site while the proximal end 101 of the shunt 100 is positioned on an inner wall of the vena cava.

In cases where thrombus is located along the wall of the arterial puncture site (e.g., in some instances in response to an implanted endograft), the distal end 103 of the shunt 100 may be advanced through at least a portion of the thrombus until the distal end 103 reaches an inner lumen of the aorta. In some embodiments, the distal end of the delivery system may be moved proximally (e.g., out of the aorta, through the venous puncture site, and into the vena cava) to help deploy the shunt 100. The shunt 100 may be implanted at any suitable location relative to the aneurysm. In some cases, the puncture site for the aorta may be located upstream (e.g., superior) of the aneurysmal sac (with respect to blood flow therethrough). The shunt 100 may be implanted before, during, and/or after implantation of an endograft in the aorta of the patient to prevent and/or alleviate the occurrence of endoleaks. In some embodiments, the shunt 100 and the endograft may be implanted in one procedure. For example, the endograft may be positioned in the aorta after the venous puncture site and the arterial puncture site are formed (e.g., after transcaval access is established) to avoid the possibility of the distal end of the delivery system damaging the endograft. Transcaval puncture to establish access to the aorta is preferably performed prior to endograft delivery to reduce possibility of complications during implantation. Difficulties may arise from the following scenarios, for example, (1) The aorta may have calcification, scarring, fibrosis, or some combination thereof that stiffens the tissue, which can increase the force required to puncture the tissue and cause "jumping" or jerking of the needle or guide wire after puncture. Therefore, accidental perforation of the aorta may occur due to difficulty controlling movement of the guidewire or needle after puncture; (2) the geometry of the abdominal aortic aneurysm may bias the endograft towards/ against the endovascular surface of the aorta, leaving little to no space for transcaval puncture, as can occur with a "left-sided" aneurysm).

In some embodiments, the shunt 100 may transition from the delivery configuration to the deployed configuration as the shunt 100 is advanced out of an opening defined by the distal end of the delivery system. For example, while inside the catheter, the shunt 100 may be in the delivery configuration in which the shunt 100 is constrained (e.g., to allow advancement through the catheter), and as the shunt 100 exits the catheter, the shunt 100 may transition to the deployed configuration in which at least a portion of the shunt 100 is expanded. In some embodiments, the venous sealing structure 104 and the arterial sealing structure 106 may expand or flare out (e.g., the diameter $D_V$, $D_A$ of the sealing structures 104, 106 may increase). In some embodiments, one or both of the arterial sealing structure 104 and venous sealing structure 106 may be self-expandable. Accordingly, in some embodiments, the shunt 100, via the deployed arterial sealing structure 106 and venous sealing structure 104 may help form a circumferential fluid seal around the vascular puncture sites, creating a fluid passageway between the venous puncture site and the arterial puncture site to permit blood flow from the aorta to the vena cava.

In some embodiments, the venous sealing structure 104 and the arterial sealing structure 106 may have a starting diameter in the delivery configuration and may expand to an expanded diameter larger than the starting diameter in the deployed configuration. As shown in FIG. 1B, the diameter of the venous sealing structure $D_V$ and the diameter of the arterial sealing structure $D_A$ are larger than in the delivery configuration. Additionally or alternatively, the central portion 102 of the shunt 100 may narrow when the shunt transitions to the deployed configuration to form an hourglass or dumbbell shape, as shown in FIGS. 5A-C and FIGS. 6A-6E and described in further detail below. For example, the diameter of the central lumen $D_B$ may decrease from the delivery configuration to the deployed configuration. In some embodiments, when the shunt 100 is in the deployed configuration, the central lumen of the central portion 102 may have a diameter (inner diameter) $D_B$ in a range between about 0.5 mm to about 100 mm, about 1 mm to about 50 mm, about 2 mm to about 25 mm, about 3 mm to about 15 mm, about 4 mm to about 10 mm, or about 3 mm to about 8 mm, inclusive of all ranges and subranges therebetween. In some embodiments, as the shunt 100 transitions from the delivery configuration to the deployed configuration, the length $L_B$ of the central lumen (and therefore the central portion 102) may increase. In some embodiments, in the deployed configuration, the central portion 102 and the central lumen have a length $L_B$ in a range of about 10 mm to about 10 cm, inclusive of all ranges and subranges therebetween.

In some embodiments, the deployed arterial sealing structure 106 and/or deployed venous sealing structure 104 may have a diameter (inner diameter) $D_V$, $D_A$ in a range of about 0.5 mm to about 200 mm, about 1 mm to about 100 mm, about 5 mm to about 75 mm, about 8 mm to about 50 mm, about 10 mm to about 30 mm, or about 10 mm to about 20 mm, inclusive of all ranges and subranges therebetween. In some embodiments, the diameter $D_A$ of the deployed arterial sealing structure 106 may be equivalent to the diameter $D_V$ of the deployed venous sealing structure 104. In some embodiments, the diameter $D_A$ of the deployed arterial sealing structure 106 may not be equivalent to the diameter $D_V$ of the deployed venous sealing structure 104. In some embodiments, an inner diameter of the sealing structures 104, 106 and an outer diameter of the sealing structure 104, 106 may differ by a thickness of the material of the shunt 100. In some embodiments, one or both of the sealing structure(s) 104, 106 may include an inflatable balloon coupled thereto. Therefore, the inner diameters $D_V$, $D_A$ of the sealing structures 104, 106 (e.g., the diameter of the fluid passageway) may be substantially smaller than the outer diameters of the sealing structures 104, 106. In such embodiments, the inner diameters $D_V$, $D_A$ of the sealing structures 104, 106 may be equivalent or nearly equivalent to the diameter $D_B$ of the central lumen in the deployed configuration, while the outer diameters of the sealing structure 104, 106 expand larger than the inner diameters to seal the vessels.

In some embodiments, in the deployed configuration, the venous sealing structure 104 may have a length $L_V$ in a range of about 1 mm to about 10 mm, inclusive of all ranges and subranges therebetween. In some embodiments, in the deployed configuration, the arterial sealing structure 106 may have a length $L_A$ in a range of about 1 mm to about 50 mm, inclusive of all ranges and subranges therebetween. In some embodiments, as the shunt 100 is deployed or expanded, a total length of the shunt 100 may decrease. For example, the length $L_V$, $L_A$ of the venous sealing structure 104 and arterial sealing structure 106, respectively, may decrease such that the total length of the shunt 100 decreases.

The shunt 100 may include a material such as a shape-memory alloy that allows the shunt 100 to conform to different configurations (e.g., the compressed configuration and the expanded configuration). In some embodiments, the shunt 100 may include a flexible, compliant stretchy tube that can lengthen as the aneurysmal sac shrinks, and as the distance between the puncture sites of the aorta and vena cava increases. Additionally, the material may enable the sealing structures 104, 106 to pivot or bend. In some embodiments, the central portion 102 and/or the sealing structures 104, 106 may include braided or laser cut metal and/or alloy, a bioabsorbable material, a polymer, a compliant balloon, or any combination and/or variant thereof. In some embodiments, the shunt 100 may include a material (e.g., a metal alloy) that promotes endothelialization. In some embodiments, at least a portion of the shunt 100 may be laser cut from super-elastic metal and/or braided from super-elastic wires to have a heat set shape. The material may be any suitable material including, but not limited to, copper-aluminum-nickel, nickel-titanium (Nitinol), copper-zinc-aluminum, iron-manganese-silicon, brass, steel or a suitable combination thereof. In some embodiments, the material includes Nitinol. Nitinol is a super-elastic material with shape-memory properties, and implementation of Nitinol in the shunt 100 allows the shunt 100 to adapt to dynamic vascular environments. The compliance of the material of the shunt 100 may also ensure that the shunt 100 remains functional and effective even as the anatomy of the vessels changes over time.

In some embodiments, the central portion 102 of the shunt can stretch from about 1% to about 300% of its original length (e.g., such as when the aneurysm shrinks and thereby causes increased separation between the vena cava and the aorta), inclusive of all ranges and subranges therebetween. In some embodiments, the central portion 102 can compress from about 100% to about 25% of its original length (e.g., when transitioning into the deployed configuration from the delivery configuration), inclusive of all ranges and subranges therebetween. In some embodiments, the sealing structures 104, 106 may be configured to compress from about 100% to about 25% of their original length, inclusive of all ranges and subranges therebetween. In some embodiments, the sealing structures 104, 106 are identical in shape, size, and/or material to each other. In some embodiments, the arterial sealing structure 106 is not identical in shape, size, and/or material as the venous sealing structure 104, to account for differences in mechanical and fluid properties found between the vein and the artery.

In an endovascular procedure, the ability of the shunt 100 to expand from a substantially uniform cylindrical shape to one with a narrowed middle section is beneficial for several reasons. First, this allows for targeted pressure distribution: the narrowed central portion 102 can help focus and control the flow of blood through the shunt 100, which may reduce the risk of turbulent flow and promote a laminar flow pattern, lessening stress on the vessel walls. Second, having a shape with a narrow central portion 102 may be important in some instances for stability and/or anchoring. In particular, the wider ends of the shunt 100 can anchor the shunt 100 securely within the vessels, preventing migration, while the narrowed section reduces contact of the material of the shunt with the blood vessels, potentially minimizing the risk of thrombosis. Third, with regards to delivery and deployment, starting in a compressed, compact configuration allows the shunt 100 to be introduced through a low-profile catheter. This minimizes vessel trauma during introduction and transcaval positioning, as the reduced diameter of the catheter and shunt assembly lessens the force required to penetrate the vessel walls, thus reducing the risk of arterial or venous injury.

The sealing structures 104, 106 when the shunt 100 is in the deployed configuration may be configured to form a seal between an outer surface of the shunt 100 and the puncture sites to permit blood flow through the shunt 100 and/or prevent leakage of blood. When the shunt 100 is in the deployed configuration, the venous sealing structure 104 may be configured to conform to an inner surface (e.g., the endovascular surface) of the vena cava to seal the venous puncture site and prevent blood from flowing out of the vena cava and into the extravascular space. Similarly, the arterial sealing structure 106 in the deployed configuration may be configured to conform to an inner surface (e.g., the endovascular surface) of the aorta and/or a surface of the thrombus to prevent blood from flowing out of the aorta and into the extravascular space. In some embodiments, the sealing structure 104, 106 when expanded may help secure the shunt 100 in position and/or prevent movement of the shunt 100. In some embodiments, the sealing structures 104, 106 may further include a balloon-expandable component that, once positioned, can be inflated to press against the vessel walls, adapting to the shape of the vessel walls and securing the shunt 100 in place. This technique allows for a customized fit to unique vascular anatomy of the patient, further enhancing the efficacy of the seal.

Figure 6A:
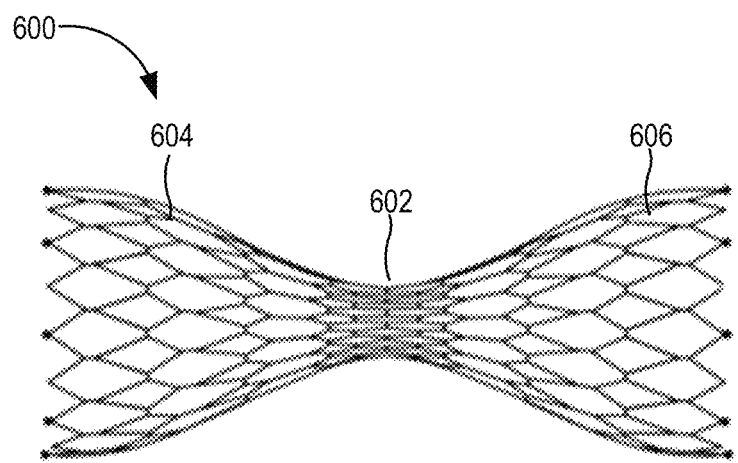
FIGS. 6A-6D are side views of a shunt in the deployed configuration forming an hourglass shape, according to an embodiment.
Figure 6B:
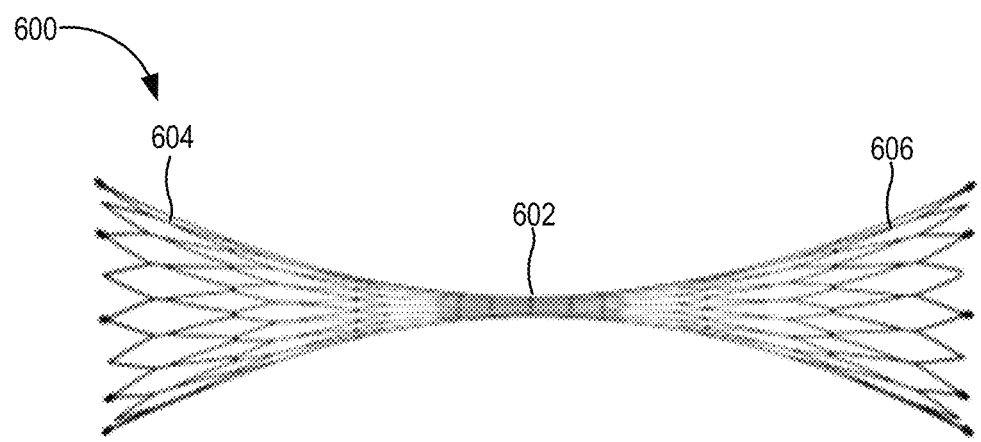
Figure 6C:
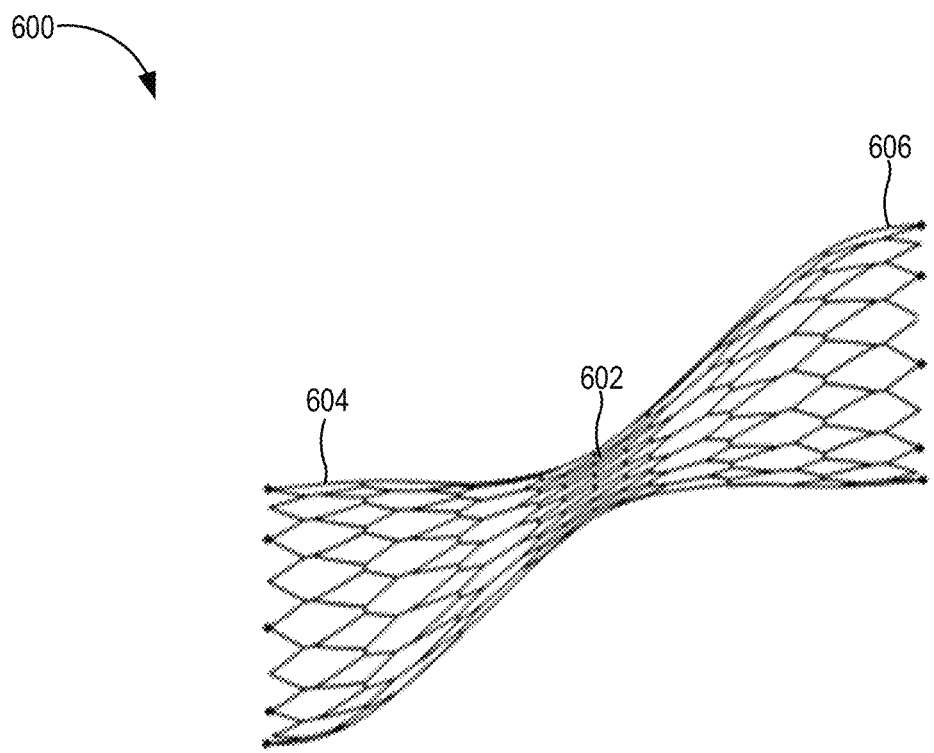
Figure 6D:
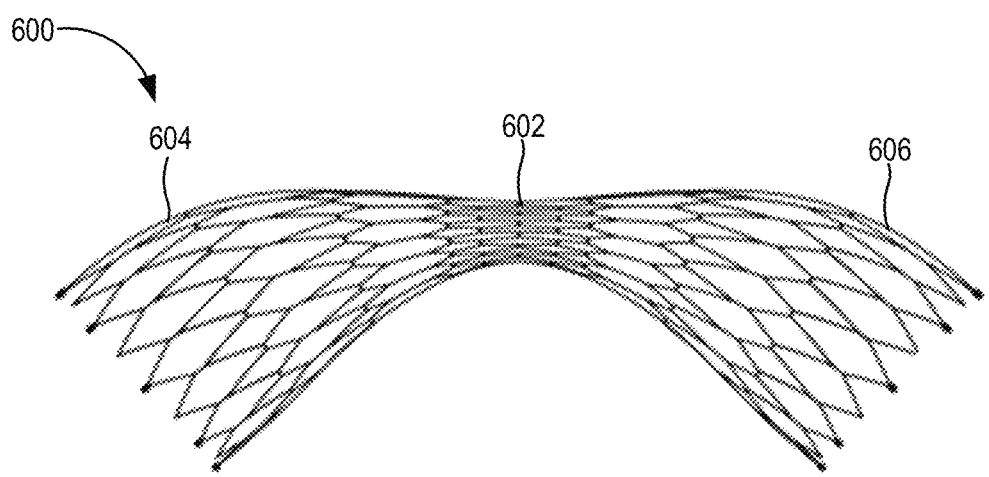
Figure 6E:
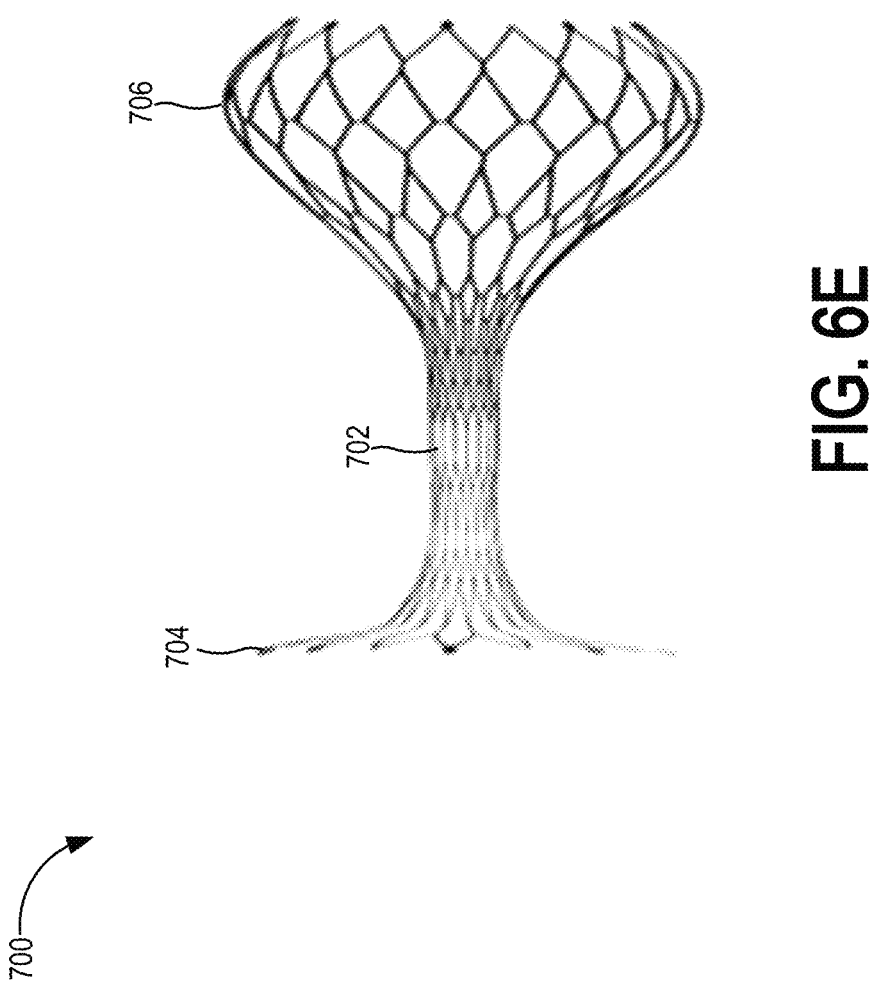
FIG. 6E is a side view of a shunt in the deployed configuration in which the arterial sealing structure forms a conical bulb shape, according to an embodiment.
Figure 7:
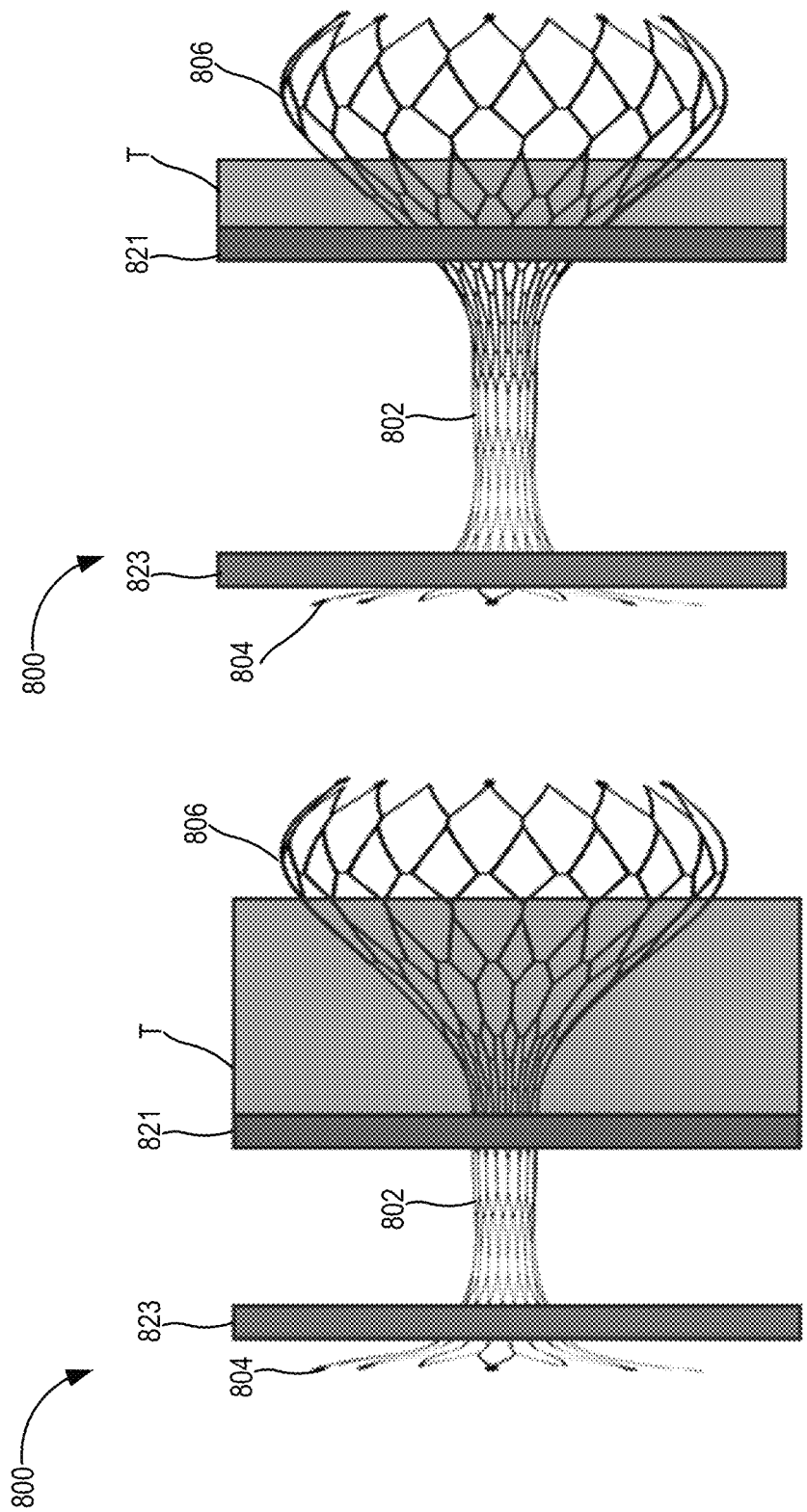
FIG. 7 is an illustration of the shunt in the deployed configuration illustrating positioning of a venous sealing structure relative to a wall of a vein and an arterial sealing structure relative to a wall of an artery including thrombus, according to an embodiment.

In some embodiments, the shunt 100 may be configured to include or assume an asymmetrical shape such as a "shuttlecock" shape when in the deployed configuration, as shown in FIG. 6E and FIG. 7. For example, the venous sealing structure 104 may form a disc shape (or saddle shape) configured to conform to the endovascular saddle shaped profile of the vena cava, and the distal sealing structure 106 may form a conical bulb shape (e.g., conical shape, elliptical cone, parabolic cone, oblate spheroid, or the like). One advantage of the shuttlecock shape is that the venous sealing structure 104 may lay flush against the endovascular surface of the vena cava to minimize disruption to venous blood flow through the vena cava. This helps prevent clot formation as well as promote tissue ingrowth over a larger surface area to provide structural stability to the arteriovenous connection. When in the deployed configuration, the venous sealing structure may be disc shaped (or saddle shape) and under tension due to the expansion of the arterial sealing structure 104, which enables the venous sealing structure 104 to lay flush against the vessel wall regardless of whether the vessel wall has concavities. The conical bulb of the arterial sealing structure 106 allows for robust functionality of the shunt (e.g., enabling drainage of blood) regardless of thrombus thickness as described herein This shape also serves to gently displace the thrombus away from the endoleak drainage pathway (e.g., the central lumen) to permit arteriovenous blood flow. Additionally, through the displacement of thrombus, this shape facilitates the creation of a tensile force between the venous sealing structure 104 and the arterial sealing structure 106 to support a fluid tight seal around the outer surface of the shunt 100. The rounded bulb protects an endograft from damage due to contact with the endoleak shunt in the case of aneurysm shrinkage. In some embodiments, the bulb of the arterial sealing structure 106 can include an open distal end, as shown in FIG. 6E and FIG. 7. In some embodiments, the bulb of the arterial sealing structure 106 can be closed at the distal end (like the head of a microphone) to prevent large clots from passing through or clogging the shunt.

In some embodiments, the shunt includes one or more (e.g., 1, 2, 3, 4, 5, 6, 7, 8, 9, or 10) radiopaque markers. In some embodiments, the radiopaque markers are disposed at the proximal end 101 of the shunt 100. In some embodiments, the radiopaque markers are disposed at the distal end 103 of the shunt 100. In some embodiments, the radiopaque markers are disposed at both the proximal and distal ends 101, 103 of the shunt 100.

In some embodiments, the venous sealing structure 104 and the arterial sealing structure 106 may pivot (hinge, bend, curve, deform, etc.) relative to the central portion 102 of the shunt 100 to accommodate movement and/or variations in alignment between attachment points (e.g., the locations on the vessel walls to which the sealing structure 104, 106 are coupled). For example, the shunt 100 may include a flexible material (e.g., Nitinol) that allows the sealing structures 104, 106 to pivot or hinge to ensure a fluid tight seal regardless of puncture angle. The pivotable design of the sealing structures 104, 106 relative to the central portion 102 of the shunt 100 further ensures a secure and adaptable connection within the vascular system. For example, if an angle between the aorta and the vena cava may change due to body movements or alterations in the vascular anatomy over time, the sealing structures can adjust accordingly, maintaining a secure, leak-proof seal around the central portion 102 of the shunt 100 that ensure proper blood flow through the shunt 100.

In some embodiments, the shunt 100 may be wholly formed of and/or include a bioabsorbable material designed to degrade over time to correspond with a change in size of the aneurysm sac (e.g., due to shrinkage of the aneurysm sac). In other words, once the aneurysm sac has remodeled itself and endoleaks are closed off, the shunt 100 may no longer be needed and can be absorbed by the body. Additionally, one or more structures of the shunt 100 may be coated or covered with or formed from a compliant material such as silicone, hydrogel, or another biocompatible polymer that can fill in the irregularities of the vessel walls, ensuring that even in areas where the vessel surface is not smooth or uniform, the seal remains intact and effective. In some embodiments, the shunt 100 may include polylactic acid (PLA) or polyglycolic acid (PGA) to support tissue ingrowth such that the shunt 100 degrades and is replaced by natural tissue (e.g., endothelial tissue) over time. In some embodiments, the cover 108 may span along at least a portion of the length of the shunt 100. The cover 108 may aid in anchoring the shunt 100 to the vascular puncture sites and/or prevent the leakage of fluids around the shunt 100. In some embodiments, the cover 108 may span at least a portion of the central portion 102 of the shunt 100 can offer localized support and maintain patency in the narrowed region, reduce turbulent flow, minimize retroperitoneal bleeding or leakage, and allow for flexibility and ease of access at the ends of the shunt. The cover 108 over the narrowed central portion 102 of the shunt 100 can provide structural support, preventing collapse or excessive narrowing which could impede blood flow. Turbulent flow, often a concern in areas of narrowing, can lead to endothelial damage and increased risk of thrombosis. The cover 108 can help smooth the transition of blood flow through the narrowed section, reducing turbulence and associated risks. By concentrating the cover 108 on the central portion 102, the flexibility of the ends 101, 103 of the shunt 100 may be maintained. This is important for accommodating movement and reducing the stress on the vascular anastomoses (junctions).

In some embodiments, the shunt 100 may be configured to adapt to changes in geometry as the aortic aneurysm begins to shrink. For example, the superelastic material of the shunt 100 may allow the shunt 100 to comply to changing vessel geometry while still maintaining a level of firmness to prevent the shunt 100 from collapsing. The sealing structures 104, 106, particularly for interfacing with the endovascular surface of the inferior vena cava and the aortic aneurysm, may be configured to adapt to the internal contours of these vessels. The shunt 100 may be configured to allow for a degree of expansion or contraction to accommodate variations in vessel diameter and surface irregularities. For instance, sealing structures 104, 106 may each include a self-expanding mechanism, which may exert a continuous outward force (e.g., radial force) against the vessel walls. This ensures contact with the endovascular surface, conforming to the shape and providing a secure seal to prevent blood leakage. As the aneurysm shrinks as facilitated be the implantation of an endograft and/or the creation of an arteriovenous connection between the abdominal aortic aneurysm and the vena cava, the distance between the vena cava and the abdominal aorta may increase or otherwise change in some manner. The shunt 100 can accommodate this change through its superelastic property, which allows the shunt 100 to maintain apposition against the vessel walls despite changes in spatial geometry. This elongation can lead to a reduction in the diameter of the shunt's central portion 102 and central lumen. As the aneurysm shrinks, the flow rate of an endoleak through the shunt 100 correspondingly diminishes because the driving pressure behind the endoleak decreases. In some embodiments, if the aneurysm heals to the point where an endoleak no longer exists, the blood flow through the shunt 100 may cease, and the shunt 100 may close off. This closure would occur due to the lack of pressure differential needed to maintain the patency of the shunt 100. The gradual nature of this transition allows the patient's vascular system to adjust slowly, enhancing overall circulatory stability and reducing the risk of complications.

The radial force of the shunt 100 is defined as the force generated in a direction outward (e.g., radially) from the surface of the shunt 100. In some embodiments, the shunt 100 can elongate or shorten without a decrease in the radial force of the outer surface of the sealing structure 104, 106 on the vessel walls, ensuring that the seal remains intact, and the stent continues to provide fluid communication between the two vessels with little to no leakage. In some embodiments, the sealing structures 104, 106 may maintain the radial force above a predetermined threshold to prevent deterioration of the seal and/or leaking of blood into the extravascular space.

In some embodiments, the shunt may optionally include a flow controller 105 disposed in the central lumen of the shunt 100. In some embodiments, the flow controller 105 may be integrated into an inner surface of the central portion 102 of the shunt 100. In some embodiments, the flow controller 105 may be coupled to a portion of the central portion 102 of the shunt 100. In some embodiments, the flow controller 105 may be a one-way valve mechanism positioned centrally along the total length of the shunt 100. The flow controller 105 may be configured to allow blood to flow in a first direction through the central lumen while preventing blood from flowing in a second direction opposite the first direction through the central lumen. For example, the flow controller 105 may allow normal antegrade blood flow through the vena cava while preventing retrograde flow into the aneurysm sac. In some embodiments, the flow controller 105 may only let blood flow when certain parameters are met (e.g., a pressure, pressure gradient, absolute flow, flow gradient, etc.). In some embodiments, the parameters that allow blood to flow in the first direction may be the same or different than the parameters to allow blood to flow in the second direction. In some embodiments, the flow controller 105 may include biocompatible and/or flexible material that responds to changes in blood pressure and flow dynamics. In the presence of an endoleak, the flow controller 105 may remain open, allowing unimpeded blood flow. However, in the presence of reversed flow pressure, the flow controller 105 closes, thus preventing blood from entering the aneurysm sac. The shunt 100 may additionally or alternatively include a filter or filter-like structure configured to capture and contain clots or embolic debris originating from the aneurysm sac, thereby preventing migration of debris into the systemic circulation. In some embodiments, the filter may include a fine, biocompatible mesh material. In some embodiments, a pore size of the mesh of the filter may be calibrated to trap clots while allowing normal blood flow. In some embodiments, the pore size of the mesh of the filter may be in a range of about 100 μm to about 10000 μm. In some embodiments, the filter may be affixed to the inner wall of the central portion 102 of the shunt 100 (e.g., the nitinol frame).

In some embodiments, the shunt 100 may be configured to allow blood flow or cease blood flow in response to predetermined local conditions. For example, pressure or flow may act to change the effective shunt lumen size (open, close, other). In some embodiments, when one or more parameters (e.g., a pressure, pressure gradient, absolute flow, flow gradient, etc.) reach an 'onset' threshold, the shunt 100 may increase in diameter, whereas when the one or more parameters reach an 'offset' threshold, the shunt 100 may decrease in diameter. A purpose of adaptive shunting is to protect organs or biologic tissues from pressure or flow damage. This protection may be conferred by limiting pressures at either the source or receiving end of the connection. For example, a "bleed off" shunt could be used to drop pressures which are approaching or exceeding a specified threshold value.

The thrombus within an abdominal aortic aneurysm presents unique challenges in the context of creating an endoleak drainage pathway, particularly due to its variable nature and the risks associated with disturbing it. Abdominal aortic aneurysm thrombi are typically composed of layers of blood components, including fibrin, red blood cells, and platelets. The structure can vary from soft, friable material to more organized, harder deposits. The location and extent of the thrombus can vary widely; it may line the aneurysm wall partially or entirely. Thrombus formation is a dynamic process, evolving over time. Initially, it may be more unstable and prone to fragmentation, whereas older thrombi tend to be more organized and stable. In placing a shunt 100 to create a drainage pathway for endoleaks, for example, pre-procedural imaging may be done to measure the thickness of the thrombus and to determine a suitable length $L_A$ of the arterial sealing structure 106. The length $L_A$ of the arterial sealing structure 106 in the deployed configuration may be at least as long as the thickness of thrombus. Additionally, a size (e.g., a cross-sectional area) of each cell (gap, opening) defined by the braided filaments of the shunt (or the openings between struts of a laser cut shunt) may be below an upper threshold such that the filaments do not cut into the thrombus (e.g., cause fragmentation of the thrombus) upon deployment of the shunt 100, but above a lower threshold to permit sufficient endoleak drainage rate without clots forming inside the shunt 100 and blocking blood flow. In some embodiments, the area (e.g., the cross-sectional area) of each cell defined by the shunt 100 may be in a range of about 1 mm² to about 10 mm², inclusive of all ranges and subranges therebetween. In some embodiments, the size or area the cells may vary across the total length of the shunt 100 and/or around a circumference of the shunt 100. The average size or area (cross-sectional area) of the cells in a portion of the shunt 100 may be directly proportional to a fluid porosity of the portion of the shunt 100. In some embodiments, the central portion 102 of the shunt 100 may have a fluid porosity that is less than a fluid porosity of both the arterial sealing structure 106 and venous sealing structure 104.

In some embodiments, the shunt 100 may be resized during and/or after delivery. For example, after initial delivery, a diameter of the central lumen $D_B$ of the shunt 100 may be increased or decreased depending on the anatomy of the patient and the state of the aneurysm. In some embodiments, the diameter of the central lumen $D_B$ may be increased (or expanded) by disposing an inflatable balloon in the central lumen and inflating the balloon until the target diameter of the central lumen is reached. To reduce the diameter of the central lumen $D_B$, a separate delivery catheter may be used to deliver a spacer (e.g., a tubular spacer) having a thickness that reduces the diameter $D_B$ of the central lumen. In some embodiments, the thickness of the spacer corresponds to an amount to reduce the shunt 100 diameter. In some embodiments, the spacer may include a shunt structure subsequently deployed inside of the original shunt 100. The ability to resize the shunt 100 after delivery allows for customization of the amount of fluid for each patient. Furthermore, the size of the shut 100 may be modified in a similar manner as described above at a later time if the hemodynamic needs of the patient change.

In some embodiments, flow and/or pressure changes intra-procedure may be measured when and/or to help inform resizing the shunt 100. In some embodiments, for example, Doppler ultrasound may be used to non-invasively measure blood flow velocity (in real-time or near real-time) by placing a Doppler ultrasound probe near the shunt site. Changes in flow velocity after resizing the shunt 100 can indicate the effectiveness of the resizing procedure. In some embodiments, the shunt 100 may be resized until the flow velocity reaches a predetermined flow velocity range. In some embodiments, thermal dilution may be used during the resizing procedure. Thermal dilution involves injecting a known amount of cold saline into the bloodstream and measuring the temperature change of the blood downstream. This technique may provide accurate flow measurements and can be used to assess the change in flow rate through the shunt 100 before and/or after resizing. Manometry is a pressure measurement technique that involves using a pressure transducer inserted via a catheter to directly measure the blood pressure within the shunt 100. This technique is helpful for assessing whether the resized shunt 100 is functioning within the desired pressure parameters. In some embodiments, a pressure-sensing guidewire may be used during the procedure. The pressure-sensing guidewire may be advanced through the shunt 100, allowing for precise measurement of pressure gradients across the shunt 100 before and/or after resizing. In some embodiments, a combination of flow and pressure assessment can be used. For example, Angiography with Quantitative Flow Ratio (QFR)

Analysis can be used in which visual imaging and computational analysis are used to assess both flow and pressure. After resizing the shunt 100, angiographic images are taken, and software is used to calculate the QFR, which gives a quantitative assessment of blood flow. In some embodiments, Intravascular Ultrasound (IVUS) or Optical Coherence Tomography (OCT) can be used during the procedure. These imaging techniques provide high-resolution images of the vessel and shunt 100 can be used to verify the position of the shunt 100, its expansion, and indirectly infer flow dynamics based on anatomical changes.

Tissue ingrowth can play a crucial role in ensuring the long-term success and stability of the shunt 100. In some embodiments, the shunt 100 may include one or more materials configured to promote endothelialization and/or tissue ingrowth. For example, the shunt may include metal alloys such as Nitinol and/or biodegradable polymers such as polylactic acid (PLA) and/or polyglycolic acid (PGA). The shunt may include PLA and/or PGA such that the shunt 100 degrades and is replaced by natural tissue over time. Additionally, the shunt may include porous or micro-structured surfaces that enable migration of endothelial cells into the shunt 100, promoting tissue encapsulation and integration. In some embodiments, the shunt 100 may include a combination of biodegradable materials and non-degradable materials: the biodegradable materials may create spaces or openings for tissue to grow while the non-degradable material may provide structural support for the shunt 100. Tissue ingrowth can provide the following benefits: (1) enhanced stability and anchoring; (2) reduced complication rates; (3) improved hemocompatibility; and (4) facilitate healing. Tissue ingrowth into the shunt 100 and/or shunt cover 108 helps secure the shunt 100 in place, reducing the likelihood of shunt 100 migration or dislodgement. This is particularly important in an aortocaval shunt, which involve the largest artery and vein in the body. Proper integration of the shunt 100 with the surrounding tissue can decrease the risk of complications such as infection or irritation at the site of the shunt 100 because a well-integrated shunt 100 is less likely to provide a pathway for bacterial ingress. Tissue ingrowth can lead to a more natural interface between the shunt 100 and the blood vessel, potentially reducing the risk of thrombosis (blood clotting) and improving the overall hemocompatibility of the shunt. This is critical in maintaining patency (openness) and functionality of the shunt 100. Lastly, in the initial post-surgical period, tissue ingrowth can aid in the healing process by promoting the integration of the shunt 100 with the body's natural tissue, leading to a reduction in inflammatory responses and better overall healing.

In some embodiments, the shunt 100 may include a self-adjusting mechanism (e.g., self-sizing, self-rolling, self-deployment, adjustable sizing mechanism, etc.) such that the shunt 100 can adjust a total length of the shunt 100 during and after deployment. The self-adjusting mechanism can include any mechanism configured to adjust a dimension of the shunt during and/or after deployment. In some embodiments, the self-adjusting mechanism can include a self-rolling mechanism, in which a portion of the shunt 100 rolls onto itself to adjust (e.g., increase and/or decrease) at least one of a diameter along a length of the shunt 100 or a length of the shunt 100. In some embodiments, the shunt may include a first end, a second end, and a central portion defined therebetween. In some embodiments, during deployment of the shunt and/or after deployment of the shunt, the shunt may be configured to perform at least one of (1) roll toward the central portion to decrease a total length of the shunt or (2) roll away from the central portion to increase a total length of the shunt. In some embodiments, when the shunt transitions from the delivery configuration to deployed configuration, the first end of the shunt may be configured to expand radially and the second end of the shunt may be configured to transition from a first configuration in which the second end of the shunt has a first diameter and a first length to a second configuration in which the second end of the shunt has a second diameter greater than the first diameter and a second length smaller than the first length. In some embodiments, the first end of the shunt may be the proximal end 101 and the second end of the shunt may be the distal end 103. In some embodiments, the first end of the shunt may be the distal end 103 and the second end of the shunt may be the proximal end 101. In some embodiments, the second end in the first configuration forms a substantially cylindrical shape, and the second end in the second configuration includes a toroidal shape. In some embodiments, the distal end of the shunt may roll proximally to transition the shunt from the first configuration to the second configuration. In some embodiments, the proximal end of the shunt may roll distally to transition the shunt from the first configuration to the second configuration.

In some embodiments, the arterial sealing structure 106 may include a self-rolling mechanism. For example, the shunt 100 in the delivery configuration may form a substantially cylindrical shape, and the second end of the shunt (e.g., the distal end 103 of the shunt 100) may be configured to roll proximally along a length of the shunt 100 as the shunt 100 transitions from the delivery configuration to the deployed configuration and/or after deployment of the shunt 100. In some embodiments, after deployment, the shunt 100 may roll proximally and/or unroll distally to accommodate changes to the anatomy (e.g., the vein and artery moving closer together or further apart). The distal end 103 of the shunt 100 may roll into a toroidal or ring-like structure to anchor the shunt 100 and/or form the arterial sealing structure 106. In some embodiments, the toroidal structure may be configured to engage the vessel wall to anchor the shunt 100 and/or to engage thrombus after deployment. In some embodiments, after deployment, the second end of the shunt (e.g., the distal end 103) may be configured to transition towards the second configuration in response to a distance between vessels decreasing and transition towards the first configuration in response to the distance between the artery and vein increasing.

In some embodiments, when the shunt 100 transitions from the delivery configuration to the deployed configuration, the proximal end 101 (e.g., the venous sealing structure 104) of the shunt 100 may be configured to expand (e.g., self-expand). The venous sealing structure 104 may include any suitable shape such as, for example, a bulb shape, a disc-shape, a flared shape, a cone shape. In some embodiments, the venous sealing structure 104 of the shunt 100 may form the disc-shape. In some embodiments, both the distal end 103 and the proximal end 101 may be configured to roll into the toroidal structure such that the length of the distal end 103 and/or the proximal end 101 may be adjustable. In some embodiments, at least one of the distal end 103 and the proximal end 101 of the shunt may be configured to roll (e.g., into the toroidal structure) and/or unroll during and/or after deployment.

In some embodiments, as the distal end 103 of the shunt 100 rolls proximally, a total length of the shunt 100 may decrease, and an outer diameter $D_V$, $D_A$ of the venous sealing structure 104 and the arterial sealing structure 106 may each increase to anchor the shunt 100 and/or form a seal with the vessel wall. For example, as the shunt 100 transitions from the delivery configuration to the deployed configuration, the distal end 103 of the shunt 100 may roll proximally such that the length $L_A$ of the distal end 103 decreases and the outer diameter $D_A$ of the arterial sealing structure 106 increases from the delivery configuration. During and after deployment, the length $L_A$ of the distal end 103 may be variable or adjustable depending on the vessel geometry. As the shunt 100 transitions from the delivery configuration to the deployed configuration, the length $L_V$ of the venous sealing structure 104 may decrease and the outer diameter $D_V$ of the venous sealing structure 104 may increase, as described previously. In some embodiments, the length $L_V$ of the venous sealing structure may remain constant after deployment, and the length $L_A$ of the distal end 103 of the shunt 100 may vary to accommodate vessel geometry.

In some embodiments, the inner and outer diameter of the central portion 102 in the delivery configuration may be equivalent (or substantially equivalent) to the inner and outer diameter, respectively in the fully deployed configuration. In some embodiments, the length $L_B$ of the central portion 102 may remain increase and/or decrease based on rolling of the distal end 103 of the shunt such that the total length of the shunt 100 is adjusted. In some embodiments, both the length $L_B$ of the central portion 102 and the length $L_A$ of the arterial sealing structure 106 may vary.

In some embodiments, when the shunt transitions from the delivery configuration to the deployed configuration, the diameter of the distal end (e.g., the toroidal structure) may increase while the length of the central portion may decrease. In some embodiments, after deployment and in response to a distance between two vessels increasing, a total length of the shunt may increase while a diameter of the distal end (e.g., an outer diameter of the toroidal structure) may decrease. Conversely, in response to a distance between two vessels decreasing, the total length of the shunt may decrease while the diameter of the distal end may increase. Dimensions and applications of the shunt 100 including the self-rolling mechanism are further described in FIGS. 41A-43G.

Figure 2C:
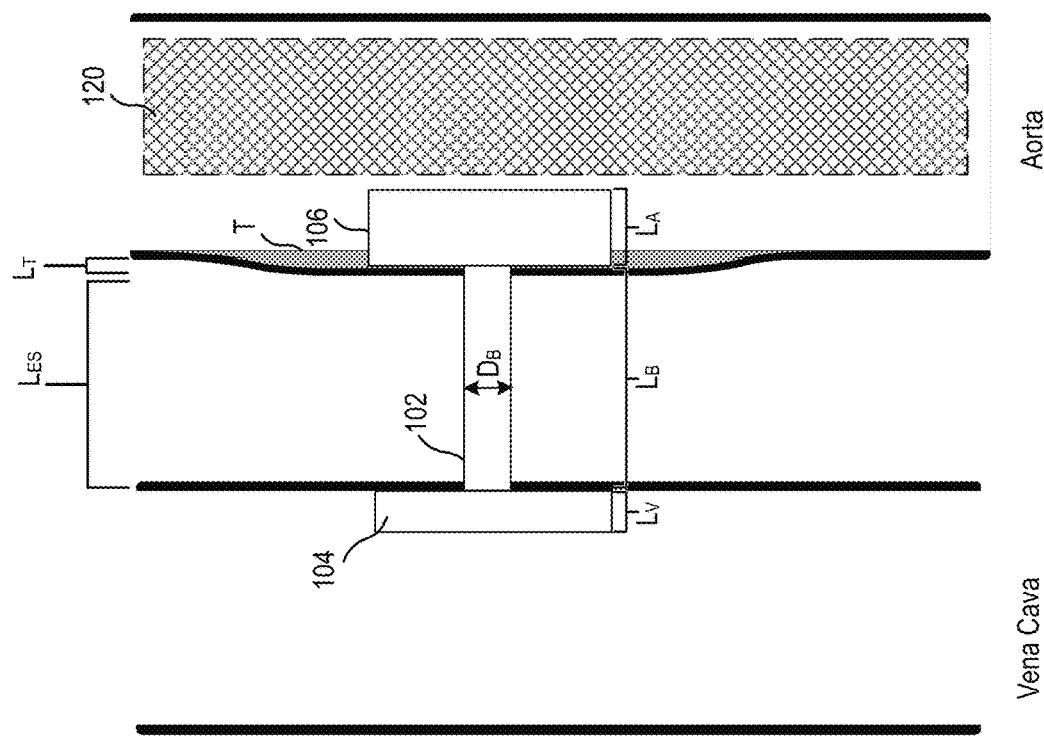

FIGS. 2A-2C are schematic block diagrams depicting placement of the shunt of FIGS. 1A-1B to connect a vena cava and an aorta of a patient to treat an aortic aneurysm (e.g., an abdominal aortic aneurysm), according to an embodiment. As shown in FIG. 2A, the shunt 100 may be moved through the venous puncture site 151 and the arterial puncture site 152 via a catheter of the delivery system 150. In some embodiments, an endograft 120 may be disposed in the aorta before or during implantation of the shunt 100, as shown. As shown, the shunt 100 has a uniform cylindrical shape. The central portion 102 of the shunt 100 (e.g., the central lumen) has a diameter $D_B$, and the venous sealing structure 104 and the arterial sealing structure 106 each have a diameter equivalent to the diameter $D_B$. The central portion 102 of the shunt has a length $L_B$, the arterial sealing structure has a length $L_A$, and the venous sealing structure has a length $L_V$. The thrombus T is shown in grey and has a length $L_T$. As shown, the thrombus T causes the arterial wall to deform. The extravascular space (e.g., the space between the vena cava and the aorta) has a length denoted as LES. As shown in FIG. 2B, the shunt 100 is transitioned to the deployed configuration such that the venous sealing structure 104 seals the venous puncture site 151 and the arterial sealing structure 106 seals the arterial puncture site 152 to allow blood flow through the shunt 100 toward the vena cava. In the deployed configuration, the diameter $D_B$ of the central lumen increases, and the diameters of the sealing structure 104, 106 increase in size in the deployed configuration. The length $L_V$ of the venous sealing structure and the length $L_A$ of the arterial sealing structure 106 decrease, while the length $L_B$ of the central portion 102 (and central lumen) increases. Therefore, the shunt 100 may form an hourglass (e.g., a dumbbell, a hyperboloid of one sheet, or the like) in the deployed configuration. In some embodiments, the shunt 100 may form an asymmetrical shape such as a "shuttlecock" shape in the deployed configuration. In some embodiments, the central portion 102 may remain cylindrical while one or both of the sealing structures 104, 106 form a conical shape, an elliptical cone, a parabolic cone, a conical bulb, an oblate spheroid, or the like. The length $L_V$ of the venous sealing structure 104 may be configured to be smaller than the length $L_A$ of the arterial sealing structure such that the venous sealing structure 104 lays substantially flat against the inner wall of the vena cava such that the venous sealing structure 104 does not obstruct or is limited in obstructing blood flow through the vena cava. In other words, the venous sealing structure 104 is configured to anchor and seal the shunt 100 relative to the vena cava while minimizing blood flow disruptions through the vena cava. As shown, the length $L_A$ of the arterial sealing structure 106 in the deployed configuration may be configured to be at least as long as the thickness $L_T$ of the thrombus T. Therefore, the arterial sealing structure 106 may be configured to span at least the thickness $L_T$ of the thrombus T to improve blood flow through the shunt 100 and to avoid clotting and/or blockage of the shunt 100. For example, with the shunt 100 in the deployed configuration, the arterial sealing structure extends laterally beyond the thrombus such that the thrombus is disposed between a distal end of the arterial sealing structure and an inner wall surface of the artery proximal to the distal end of the arterial sealing structure. In some embodiments, the increased diameter $D_A$ of the arterial sealing structure 106 may be operable to push the thrombus away from the inner lumen of the shunt to further prevent clotting and/or blockage near or in the shunt.

FIG. 2C shows the shunt 100 implanted between the aorta and the vena cava after the thrombus T has decreased in size (e.g., due to improvement of the aneurysm). As shown, the thickness $L_T$ of the thrombus T has decreased, and therefore the length LES of the extravascular space has increased. As shown, the shunt 100 is configured to accommodate this change: the length $L_B$ of the central portion 102 has increased, and the diameter $D_B$ of the central lumen has decreased.

Figure 3A:
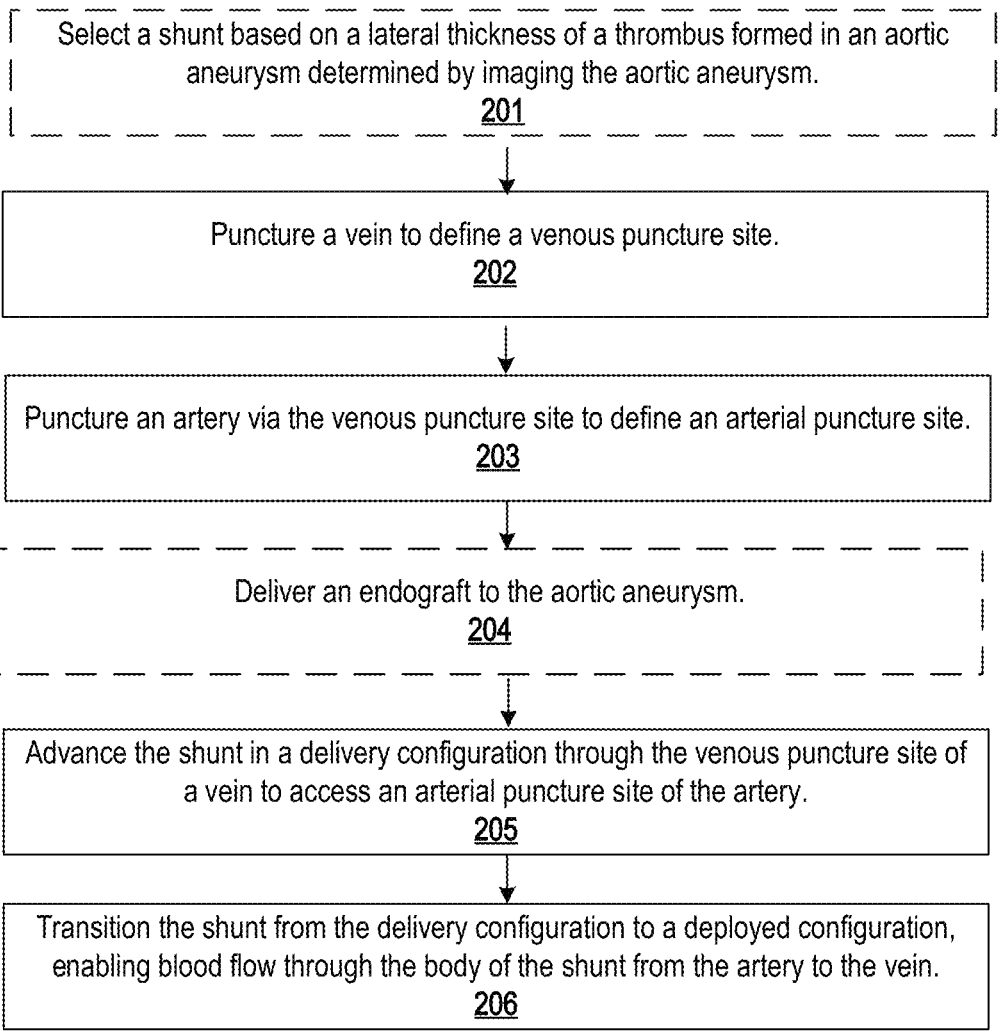
FIGS. 3A-3B are a flow diagrams of an example method of using the shunt of FIGS. 1A-1B to treat an aortic aneurysm, according to an embodiment.

FIG. 3A is a flowchart of an example method of using a shunt to treat or alleviate an aortic aneurysm, according to an embodiment. In some embodiments, the implantation site may be imaged to determine one or more characteristics of the shunt. In some embodiments, a size of the shunt may be determined based on imaging data collected during imaging. For example, CT angiography imaging may be performed to determine a lateral thickness of the thrombus. The shunt to be used may be selected based on the lateral thickness of the thrombus, at 201. In some embodiments, the arterial sealing structure of the shunt may have a thickness at least as wide as the thickness of the thrombus. In some embodiments, imaging (e.g., CT angiography) may also be used to determine one or more characteristics of the thrombus and/or to identify target punctures sites in the vena cava.

In some embodiments, the method includes puncturing a vein to define a venous puncture site, at step 202 In some embodiments, the distal end of a delivery system may be used to puncture a target puncture site on a wall of the vena cava to define the venous puncture site. In order to access the target puncture site, the distal end of the delivery system housing the shunt may be inserted into the femoral vein of the patient percutaneously or via a small incision. In some embodiments, a delivery system for an endograft may be inserted into the femoral artery percutaneously or via a small incision. In some embodiments, a sheath may be inserted into the vein and/or artery to facilitate introduction of the delivery system. In some embodiments, a guidewire at a distal end of the shunt delivery system may be moved through the vena cava toward the puncture site using a medical imaging technique (e.g., fluoroscopic guidance). In some embodiments, the distal end of the delivery system may be aligned with the venous puncture site (e.g., perpendicularly). In some embodiments, a catheter radiopaque marker disposed at the distal end of the catheter shaft may provide a signal useful to determining the location of the distal end of the catheter shaft in relation with venous puncture site and the arterial puncture site. Then, a needle may be advanced through a venous puncture site. Additionally and/or alternatively, the guidewire may be used to perform vessel puncture. In some embodiments, electrocautery may be applied when puncturing the vessels to seal an edge of the puncture site.

At step 203, an artery may be punctured via the venous puncture site to define an arterial puncture site. For example, the guidewire and/or needle may be advanced through the venous puncture site, across the extravascular space, and toward the wall of the artery. Then, the guidewire and/or needle may be used to puncture the artery to define the arterial puncture site. In some embodiments, access by the guidewire and/or needle to the aneurysm sac is then confirmed using fluoroscopy. In some embodiments, contrast may be injected to confirm entry into the aortic lumen. In some embodiments, a dilator coupled to the delivery system may be advanced over the guidewire and used to increase a size of the opening of the venous puncture site and/or the arterial puncture site. In some embodiments, the dilator may be rotated via the catheter handle to advance the dilator into the aneurysm sac. In some embodiments, the dilator may act as a support member for the shunt.

At step 204, the endograft may optionally be delivered to the aortic aneurysm such that blood flows through the endograft. A guidewire of an endograft delivery system may be advanced through a sheath of the endograft delivery system into the vascular system under fluoroscopic guidance. The guidewire may be navigated to the aneurysm site in the aorta. The endograft delivery system may be introduced over the guidewire. Precise positioning is confirmed via imaging before deployment. The endograft is deployed, creating a new path for blood flow that excludes the aneurysm.

At step 205, the shunt may be advanced in the delivery configuration through the venous puncture site of the vein to access the arterial puncture site of the artery. The shunt device may be introduced over the previously established transcaval guidewire (e.g., including the dilator) and navigated to the implantation site. In some embodiments, a sliding sheath may be disposed in the catheter and coupled to the shunt. In some embodiments, the shunt and the sliding sheath may be detachably attached, the shunt being initially held in an undeployed configuration, and the sliding sheath being disposed within the inner diameter of the shunt. The shunt may preferably be positioned so that about half of its length is positioned in the aneurysm sac and the vena cava, respectively. In some embodiments, the sliding sheath may be advanced until at least the arterial sealing structure is located within the aorta (e.g., the aneurysm sac). At step 206, the shunt may be transitioned from the delivery configuration to the deployed configuration, to allow blood to flow through the central portion of the shunt from the artery to the vein. Once in position, the sliding sheath and the dilator may be withdrawn (e.g., proximally). In some embodiments, when the sliding sheath is withdrawn from the aorta, the arterial sealing structure is deployed. Then, the sliding sheath may be withdrawn (e.g., moved proximally) to deploy the venous sealing structure, thereby positioning the shunt lumen between the aorta and the vena cava. In some embodiments, the dilator may remain in the shunt lumen and act as a support member. For example, the dilator may be kept in the shunt when at least some extravascular space exists and/or when a length of the extravascular space between the aorta and the vena cava is above a threshold. In some embodiments, the dilator may be withdrawn when the sliding sheath is withdrawn. In some embodiments, when in the deployed configuration, blood may flow through the shunt during occurrence of leaking from the implanted endograft. In this way, the shunt can prevent endoleaks from occurring, which may in turn damage the aorta. In some embodiments, the implanted shunt serves to continuously drain fluid (e.g., blood) from the aneurysmal sac into the vena cava. Accordingly, in some embodiments, the shunt, via the deployed arterial sealing structure and venous sealing structure may form a circumferential fluid seal around the vascular puncture sites permitting fluid flow from the aorta to the vena cava. In some embodiments, a snare wire may be used to position and deploy the shunt, as described in further detail with respect to FIGS. 29-39.

In some embodiments, after placement of the shunt, a final assessment may be completed to ensure the shunt and/or endograft have been placed in the correct location and are stable. Angiography may be performed to confirm the correct position of the endograft and the endoleak shunt. Further angiography checks for the adequacy of the shunt placement and function. Once satisfactory, all wires, catheters, and sheaths are removed. Establishing transcaval access prior to endograft delivery may be desired to avoid the risk of damaging a deployed endograft during transcaval puncture. In some embodiments, the method may include resizing the shunt after delivery. Specifically, the shunt can be delivered as previously described, but the shunt lumen may be expanded to an initial diameter that is smaller than the shunt lumen is capable of expanding to. This may be achieved, for example, by further expanding the shunt lumen diameter by inflatable balloon that inflates to a desired diameter. Alternately, if it is desirable to reduce the diameter of the shunt lumen, a separate delivery catheter may be used to deliver a tubular spacer having a thickness that reduces the size of the shunt lumen. In one example, the tubular spacer may be a secondary shunt structure subsequently deployed inside of the first shunt. The ability to resize the shunt after delivery allows for customization of the amount of shunted fluid for each individual subject.

In some embodiments, the method may include implanting a bypass graft so as to divert some or all of the fluid (e.g., blood) flow around an aneurysmal sac, thereby alleviating the pressure against the aneurysmal sac, as described in further detail below with respect to FIGS. 40A-40E.

Figure 3B:
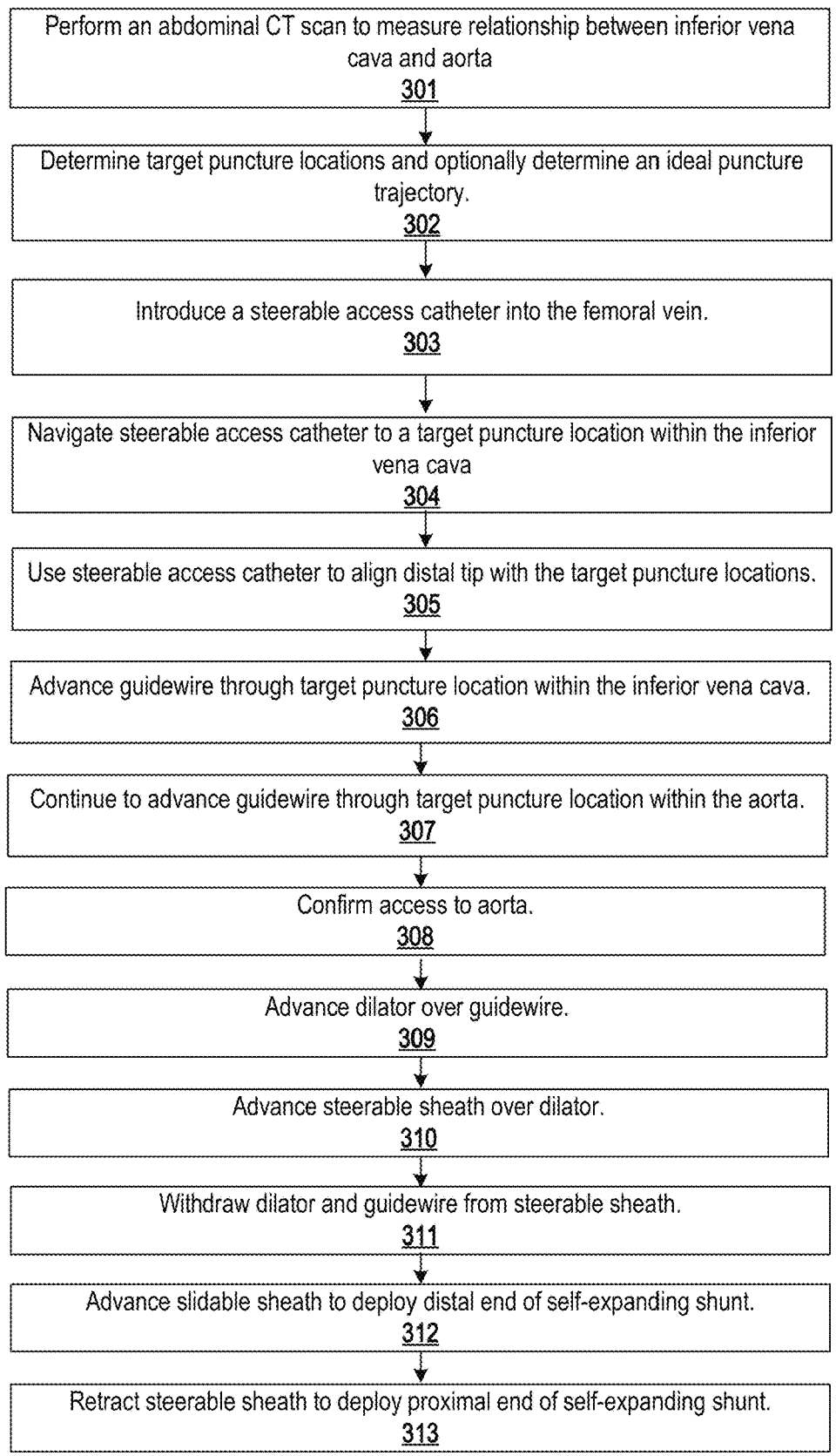

FIG. 3B is a flowchart of an example method of delivering the shunt using a delivery system, according to an embodiment. In some embodiments, the method may include performing an abdominal computed tomography (CT) scan to measure a relationship between an inferior vena cava and an aorta of a patient, at step 301. At step 302, target puncture locations in an inferior vena cava and an aorta may be determined as well as (optionally in some instances) an ideal puncture trajectory (e.g., of the distal tip of the delivery device). At step 303, a steerable access catheter may be introduced into a femoral vein of the patient. Then, the steerable access catheter may be navigated to a target puncture location within the inferior vena cava of the patient, at 304. The steerable access catheter may be used to align a distal tip (e.g., a guidewire and/or a dilator tip) of the delivery device with the target puncture location in the inferior vena cava. The guidewire may be advanced through the target puncture location in the inferior vena cava, at step 306, thereby defining a venous puncture site. At step 307, the guidewire may be further advanced through the target puncture location within the aorta. At step 308, access to the aorta may be confirmed. In some embodiments, access may be confirmed by imaging (with or without injecting contrast into the blood, and using any suitable imaging modality). At step 309, the dilator may be advanced over the guidewire to increase a size of the openings in the inferior vena cava and the aorta created by the guidewire. At step 310, the steerable sheath may be advanced over the dilator. Then, the dilator and the guidewire may be withdrawn from the steerable sheath, at 311. The steerable sheath may be advanced to deploy a distal end of the shunt, at step 312. Then, the steerable sheath may be retracted (e.g., proximally) to deploy the proximal end of the shunt. In some embodiments, the shunt may be self-expanding. The delivery system is further described with respect to FIGS. 4 and FIGS. 10A-10B.

FIG. 4 is a schematic block diagram of a distal end of a delivery system 450 configured to deliver a shunt 400, according to an embodiment. As shown, the delivery system 450 includes a catheter 460 (e.g., a steerable catheter) defining a catheter lumen. A sliding sheath 466 may extend through the catheter lumen and the shunt 400 may be detachably coupled thereto. The sliding sheath 466 may define a sheath lumen and be configured to slide over a dilator 464 including a dilator tip 465. The dilator 464 may define a dilator lumen through which a guidewire 462 may extend. During implantation of the shunt 400, once the distal end of the delivery system 450 is positioned near a target puncture site in the vein (e.g., the vena cava), the guidewire 462 may be configured to extend through an opening defined by the dilator tip 465 to puncture the vein. The guidewire 462 may be further extended through the venous puncture site toward the artery to puncture the artery. The dilator tip 465 may then be moved through the venous puncture site and/or the arterial puncture site to widen openings to accommodate a diameter of the shunt 400. For example, the dilator tip 465 may gradually increase in diameter from a distal end to a proximal end such that the distal end can be easily disposed through an opening defined by the guidewire, and as the dilator tip 465 is moved distally, the dilator tip 465 may gradually increase a size of the opening.

In some embodiments, the dilator 464 may include a cutting mechanism configured to cut through the vessels (e.g., the aorta and the vena cava) to create an anastomosis or aortocaval fistula (e.g., a fluid path between the vessels). In some embodiments, the cutting edge 476 may be disposed around a periphery of and/or and protruding from at least of a proximal end of the distal end 465 of the dilator 464 (e.g., a distal member) or a distal end of a body of the dilator 464 (e.g., a proximal member). In some embodiments, the distal member and the proximal member may be movably coupled to one another to allow for relative axial movement between a first configuration in which the proximal member and the distal member are spaced a distance sufficient to span across a venous wall of a vein and an arterial wall of an artery, and a second configuration in which the proximal member and the distal member are spaced less than a thickness of at least one of the venous wall or the arterial wall. In some embodiments, one of the proximal member or the distal member having a cutting edge configured to cut through the venous wall and the arterial wall In some embodiments, a portion of the dilator 464 proximal to the dilating tip 465 may have a reduced diameter and form a cutting edge 476. The cutting edge may include a tapered surface with a blade. The dilator 464 may include a blunt surface 475 proximal to the first cutting edge 476. In some embodiments, the cross-section of the cutting edge and/or the blunt surface may form an oval or a circle. In some embodiments, the cutting edge 476 and the blunt surface 475 may have matching profiles and be configured to oppose one another. In some embodiments, the cutting edge 476 and the blunt surface 475 may be parallel to one another. In some embodiments, once the distal end of the dilator 464 including the first cutting edge is disposed through a puncture site, the distal end of the dilator 464 may be retracted (e.g., proximally) such that the cutting edge 476 contacts the blunt surface 475, capturing the vessel therebetween, thereby cutting a portion of the vessel wall. In some embodiments, the dilator 464 may be retracted (e.g., transitioned from an extended configuration to a retracted configuration) after the dilator tip 465 and first cutting edge have been disposed through both a venous puncture site and an arterial vessel site, such that both the vein and the artery are captured between the cutting edge 476 and the blunt surface 474 and cut simultaneously. In some embodiments, a shaft may be coupled to the dilator 464 (e.g., extend at least partially through a lumen of the dilator 464) and configured to extend and/or retract to move the distal end of the dilator 464 between a first configuration (extended configuration) in which the cutting edge 476 and the blunt surface 475 are separated by a distance and second configuration (retracted configuration) in which the cutting edge 476 and the blunt surface 475 oppose one another. In some embodiments, the shaft may not extend entirely through the dilator 464. For example, the shaft may move the distal end of the dilator 464 in a proximal direction to transition the cutting apparatus from the first configuration to the second configuration. In some embodiments, the dilator 464 may be configured such that the cutting edge 476 and the blunt surface 475 in the extended configuration may define a distance therebetween corresponding to at least a distance of the extravascular space. In some embodiments, the cutting edge 476 may cut the vessel wall to have a shape of the cutting edge 476 (e.g., an oval or a circle with a desired diameter).

In some embodiments, a predetermined pressure may be applied between the cutting edge 476 and the blunt surface 475 to cut out a small circular and/or oval section of the target vessel (e.g., the aorta and/or the vena cava). In some embodiments, the pressure applied between the cutting edge 476 and the blunt surface 475 may be controlled internally in the catheter. In some embodiments, the pressure may be controlled by a handle attached to a proximal end of the catheter. In some embodiments, the cutting edge 476 and/or the blunt surface 475 may be configured to apply heat (e.g., electrocautery) during the cutting.

In some embodiments, the sliding sheath 466 of the delivery system 450 may be configured to slide over the dilator 464 to position the shunt 400 between the venous and arterial puncture sites. In some embodiments, the sliding sheath 466 may be disposed in an inner diameter of the shunt 400. The shunt 400 may be coupled to the sliding sheath 466 such that the shunt 400 is constrained to the delivery configuration until the sliding sheath 466 is withdrawn (e.g., moved proximally). For example, the proximal and distal ends of the shunt 400 may be temporarily attached to the sliding sheath 466 such that when the sliding sheath 466 is moved proximally, the ends of the shunt 400 detach, allowing the sealing structures to expand. In some embodiments, once the shunt 400 is in position with the distal end of the shunt positioned in the aorta, and the proximal end of the shunt 400 positioned in the vena cava, the sliding sheath may be retracted proximally such that the arterial sealing structure and the venous sealing structure expand.

In some embodiments, the sliding sheath 466 of the delivery system 450 may include one or more bias members (e.g., inflatable devices) disposed along the length of the shunt 400. For example, slidable sheath 466 may include two or three inflatable balloons that may be inflated to different diameters to deform the shunt 400 into an hourglass or shuttlecock shape, for example. In some embodiments, the slidable sheath 466 may include one balloon that when inflated has an hourglass or shuttlecock shape. Use of inflatable balloons allows the central portion of the shunt 400 to expand to a desired diameter while ensuring the sealing structures to expand to a diameter independent of the diameter of the central portion 102 to engage the surrounding tissue.

In some embodiments, one or more portions of the distal end of the delivery system may include one or more radiopaque markers to guide navigation of the distal end and delivery of the shunt 400. For example, the catheter 460, the sliding sheath 466, the dilator 464, the dilator tip 465, the guidewire 462, the distal end of the shunt 400, and/or the proximal end of the shunt 400 may include one or more radiopaque markers. The delivery system is described in further detail with respect to FIGS. 10A-10B.

Figure 5A:
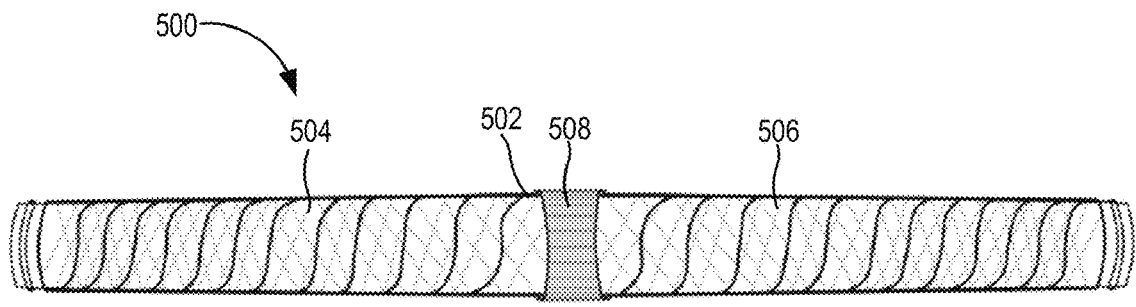
FIG. 5A shows a side view of a shunt for treating or alleviating an aortic aneurysm in a delivery configuration, according to an embodiment.

FIG. 5A shows a side view of a shunt 500 for treating aortic aneurysm in a delivery configuration, according to an embodiment. As shown, the shunt 500 includes a central portion 502, a venous sealing structure 504, and an arterial sealing structure 506. The shunt 500 further includes a cover 508 disposed around the central portion 502 at or near a center point of the shunt 500. The shunt 500 may be structurally and/or functionally similar to the shunt 100, and therefore certain details of the shunt 500 may not be described herein with respect to FIGS. 5A-5C. As shown, the shunt 500 in the delivery configuration forms a cylindrical shape such that a diameter of along the length of the shunt 500 is constant or has little (less than 5%) fluctuation. The distal and proximal ends of the shunt 500 may include radiopaque markers to provide visual aid during placement of the shunt 500.

Figure 5B:
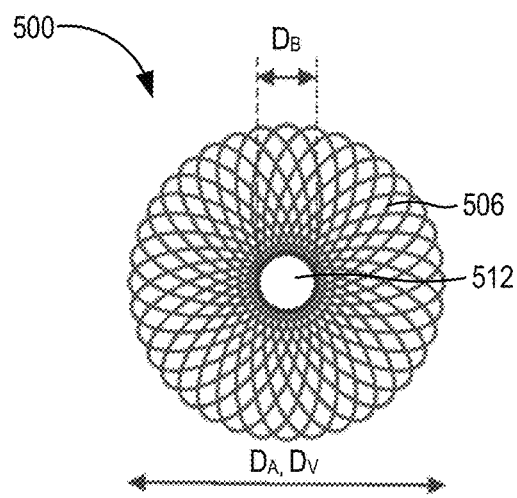
FIGS. 5B-5C show a front view and a side view, respectively, of the shunt in a deployed configuration, according to an embodiment.
Figure 5C:
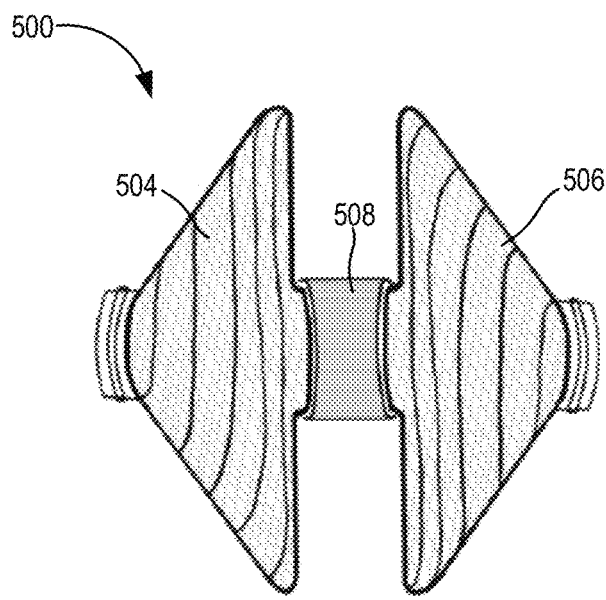

FIGS. 5B-5C show a front view and a side view, respectively, of the shunt in a deployed configuration. As shown in FIG. 5B, in the deployed configuration, the diameter $D_B$ of a center lumen 512 defined by the central portion 502 is smaller than the maximum diameters $D_A$, $D_V$ of the arterial sealing structure 506 and the venous sealing structure (not shown). The arterial sealing structure 506 and the venous sealing structure 504 in the deployed configuration each form a conical shape, as shown in FIG. 5C. In some embodiments, an apex of the conical shape may point away from the central portion 502 and a base of the conical shape may be proximate to the central portion 502. For example, an outer surface of the venous sealing structure 504 proximate to the central portion 502 and an outer surface of the arterial sealing structure 506 proximate to the central portion 502 may each include a flat surface (e.g., a bottom surface of the conical shape) configured to lay against an inner wall of the vein and artery, respectively, to seal the puncture sites.

In some embodiments, the flat surface may be configured to curve or conform if the vasculature curves or changes shape. The central portion 502 of the shunt remains cylindrical in the deployed configuration such that the shunt 500 forms a dumbbell shape (e.g., a cylindrical shape disposed between two conical shape ends). In some embodiments, a length of the central portion 502 and/or the sealing structure 504, 506 may decrease as the shunt 500 transitions to the deployed configuration. In some embodiments, the length of the central portion 502 may increase when the shunt 500 transitions to the deployed configuration. In some embodiments, the cover 508, when the shunt 500 is in the deployed configuration, may be configured to span at least a portion of the length of the central portion (e.g., the length between the flat surface of the sealing structures 504, 506). In some embodiments, the cover 508 may be configured to span an entire length of the central portion 502 (e.g., the entire length between the flat surface of the sealing structures 504, 506) to provide support to the central portion 502 and prevent collapse and/or closing of the central lumen defined by the central portion.

FIGS. 6A-6D are side views of a shunt 600 in the deployed configuration including a super-elastic material formed in an hourglass shape, according to an embodiment. As shown, the shunt 600 includes a central portion 602, a venous sealing structure 604, and an arterial sealing structure 606. The shunt 600 may be structurally and/or functionally similar to the shunt 100, 500, and therefore certain details of the shunt 600 may not be described with respect to FIGS. 6A-6D. In the deployed configuration, a diameter of the venous sealing structure 604 increases proximally and a diameter of the arterial sealing structure 606 increases distally such that the sealing structures 604, 606 each form an elliptical cone shape. In some embodiments, the shunt 600 in the deployed configuration forms an hourglass shape (e.g., a hyperboloid of one sheet). For example, a maximum diameter of the venous sealing structure 600 may be at a proximal end of the shunt 600 and a maximum diameter of the arterial sealing structure 600 may be at a distal end of the shunt 600. In some embodiments, the cells defined by the shunt may vary in size across a length of the shunt. For example, the cells corresponding to the central portion 602 may be smaller in size (e.g., have a smaller cross-sectional area) than the cells corresponding to the sealing structures 604, 606 due to a higher degree of compression at the central portion 602 of the shunt 600. In other words, the central portion 602 may have a fluid porosity that is less than a fluid porosity of the sealing structure 604, 606. The shunt 600 may be configured to stretch (e.g., stretch, bend, flex, conform, deform, etc.) to accommodate changing anatomy of the vasculature, as shown in FIGS. 6B-6D. As shown in FIG. 6B, the shunt 600 may be stretched longitudinally such that a total length of the shunt 600 increases, and the diameter of the central portion 602 may decrease. The shunt 600 may enter the longitudinally stretched configuration as an aneurysm sac begins to decrease in size and a length of the extravascular space increases, for example. The shunt 600 may be configured to accommodate changes in a horizontal alignment of the venous puncture site and the arterial puncture site. The decrease in the diameter of the central portion 602 (e.g., the central lumen of the central portion) may be operable to control blood flow (e.g., to decrease blood flow) through the shunt 600.

In some embodiments, the venous sealing structure 604 and the arterial sealing structure 606 may be configured to pivot (hinge, bend, rotate, twist) relative to the central portion 602 allowing the shunt 600 to conform to changes in vessel anatomy. For example, the shunt 600 may be configured to accommodate changes in a vertical alignment of the venous puncture site and the arterial puncture site, as shown in FIG. 6C. In some embodiments, the shunt 600 may be able to accommodate curvature of at least one of the vein or the artery (e.g., curvature of a wall of the vein or the artery closest to the extravascular space between the vein and the artery), as shown in FIG. 6D.

FIG. 6E is a side view of a shunt 700 in the deployed configuration including a super-elastic material formed in asymmetrical shape, according to an embodiment. The shunt 700 may include a central portion 702, a venous sealing structure 704, and an arterial sealing structure 706. In some embodiments, the venous sealing structure 704 and the arterial sealing structure 706 may be configured to form different shapes in the deployed configuration such that the shunt 700 is asymmetrical in the deployed configuration. The venous sealing structure 704 may be configured to form a disc shape, as shown. In some embodiments, a diameter of the venous sealing structure increases in the proximal direction such that a maximum diameter of the venous sealing structure is at a proximal end of the shunt 700. In some embodiments, the venous sealing structure 704 may include a flat or substantially flat portion configured to seal the venous puncture site and secure the shunt 100 in place. As shown, the arterial sealing structure 706 may be configured to form a bulb (e.g., a conical bulb, an oblate spheroid, etc.) in the deployed configuration. Along a distal direction, a diameter of the arterial sealing structure 706 may increase until the arterial sealing structure 706 reaches a maximum diameter, then decrease such that a maximum diameter of the arterial sealing structure 706 is between the central portion 702 and the distal end of the shunt 700. In some embodiments, the bulb shape of the arterial sealing structure may be operable to displace the thrombus away from the lumen of the shunt 700 and therefore the endoleak drainage pathway to prevent blockage and/or to promote blood flow through the shunt 700. The bulb shape of the arterial sealing structure 706 through displacement of thrombus may also generate a tensile force between the venous sealing structure 704 and the arterial sealing structure to improve the seal at the venous and arterial puncture sites. Furthermore, the rounded edges of the bulb (and the absence of sharp edges) may prevent damage to the endograft by reducing likelihood the arterial sealing structure 706 punctures the endograft. Damage to the endograft may otherwise occur when the aneurysm sac shrinks and a volume between the endograft and the shunt 700 decreases.

In some embodiments, the distal end of the arterial sealing structure 706 may be open, as shown in FIG. 6E to allow blood to flow therethrough unobstructed. In some embodiments, the distal end of the arterial sealing structure 706 may be at least partially closed to prevent large clots from passing through or clogging the shunt 700. In some embodiments, a size of the opening at the distal end of the arterial sealing structure 706 may prevent clots from passing therethrough. In some embodiments, the size of the opening at the distal end of the arterial sealing structure 706 may be in a range of about 10 mm$^2$ to about 40 mm$^2$, inclusive of all ranges and subranges therebetween. In some embodiments, a length of the arterial sealing structure 706 may be greater than a length of the venous sealing structure 704, as shown for example in FIG. 6E. In some embodiments, the length of the arterial sealing structure 706 may be at least as long as a thickness of the thrombus being treated. In some embodiments, the venous sealing structure 704 may have a length that is about 10% of the length of the arterial sealing structure 706. In some embodiments, the length of the venous sealing structure may be about 5% to about 100% of the length of the arterial sealing structure 706, inclusive of all ranges and subranges therebetween. In some embodiments, the venous sealing structure 704 may be shorter in length to reduce likelihood the venous sealing structure 704 impedes blood flow in the vein (e.g., vena cava). In some embodiments, an area of the cell defined by the shunt 700 may be larger in the arterial sealing structure 706 than the central portion 702 and/or venous sealing structure, as shown in FIG. 6E. For example, the central portion 702 may be more compressed (or less expanded) meaning the area of each of the cells is smaller (e.g., the fluid porosity is lower) than the area of each of the cells (or some of the cells) in the venous sealing structure and/or the each of the cells (or some of the cells) in the arterial sealing structure 706. The central portion 702 may be more compressed such that (1) leakage of fluid through the cells in the central portion 702 is reduced; (2) the central portion 702 has more structural support and/or rigidity to aid with tissue dilation during deployment; and/or (3) there is higher surface area of material in the central portion 702 for tissue integration. In some embodiments, at least some of the cells at a terminal end of the venous sealing structure 704 may not be closed cells. In some embodiments, the cells at a terminal end of the arterial sealing structure 706 may be closed cells (as shown). In some embodiments, the shunt 100 may have open cells with large cell sizes at a proximal end (e.g., the Nitinol braids or struts may have sharp, unclosed terminal ends). The shunt 100 at the central portion 702 may include closed cells with cell sizes smaller than those at the proximal end. The shunt 700 at a maximum diameter of the bulb may further include closed cells with cell sizes equal to or larger than those at the proximal end. The shunt 700 at a distal end may include cells that converge to a common point with cell sizes smaller than those at the maximum diameter of the bulb. Therefore, a fluid porosity of the shunt 700 may vary along the length of the shunt. For example, the fluid porosity in the central portion 702 of the shunt may be less than the fluid porosity at each of the sealing structure 704, 706.

FIG. 7 is an illustration of the shunt 800 in the deployed configuration illustrating positioning of a venous sealing structure 804 relative to a wall of a vein 823 and an arterial sealing structure 806 relative to a wall of an artery 821 including thrombus T. As shown, the bulb shape of the arterial sealing structure 806 enables thrombus engagement regardless of the thickness of the thrombus T. This allows for the shunt 800 to serve as an adequate solution across a ranges of thrombus thicknesses and geometries.

Figure 8:
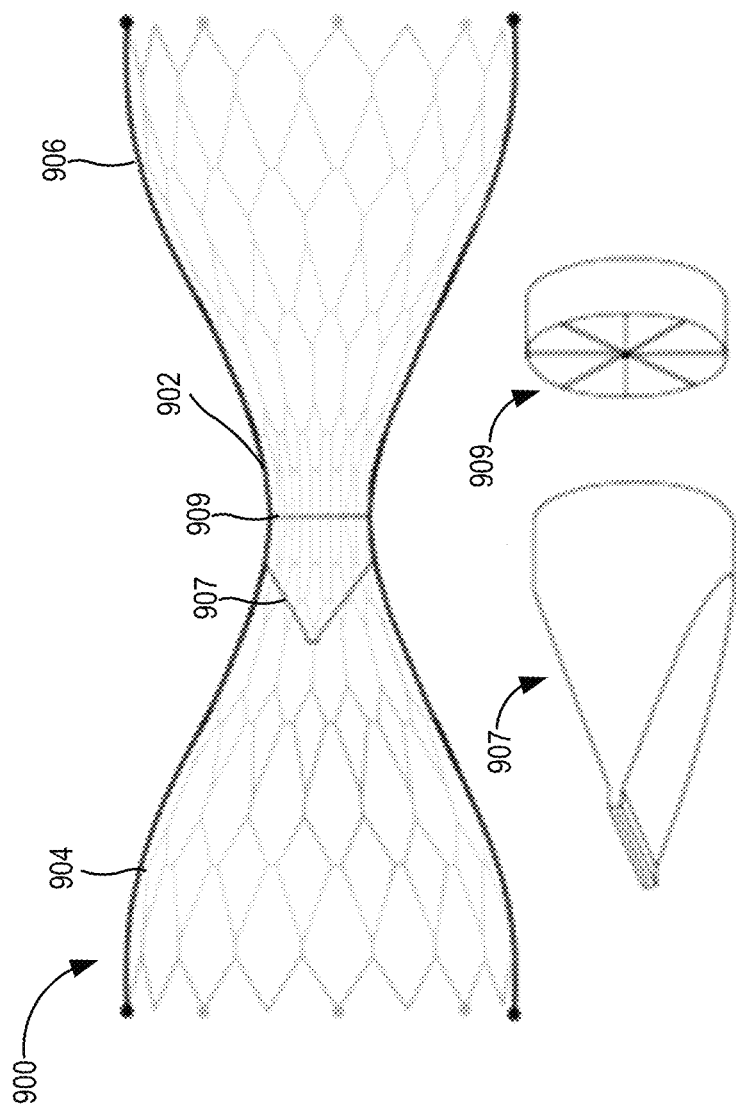
FIG. 8 is a side view of a shunt in the deployed configuration with a flow controller including a valve and a filter disposed therein, according to an embodiment.
Figure 9A:
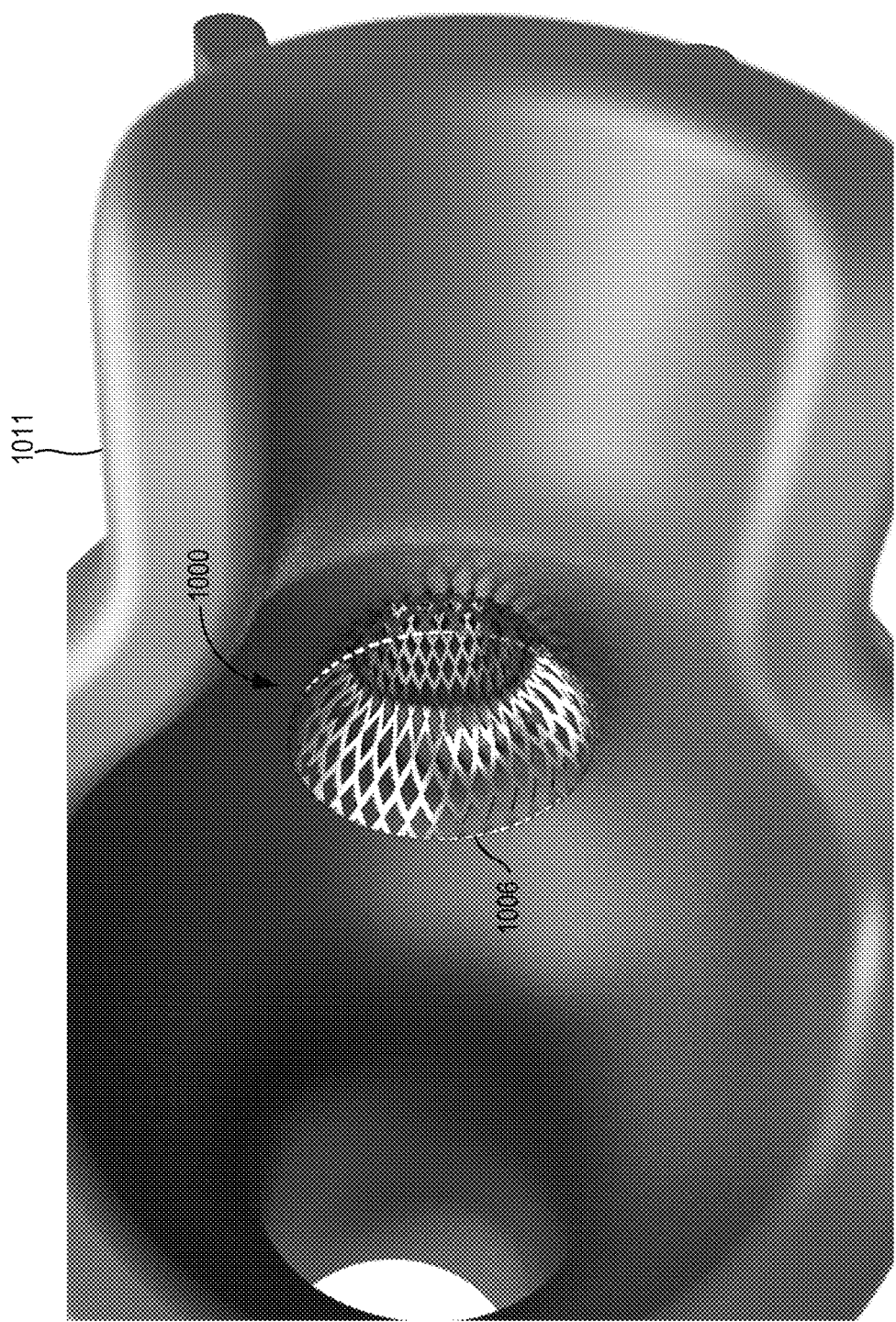
Figure 9B:
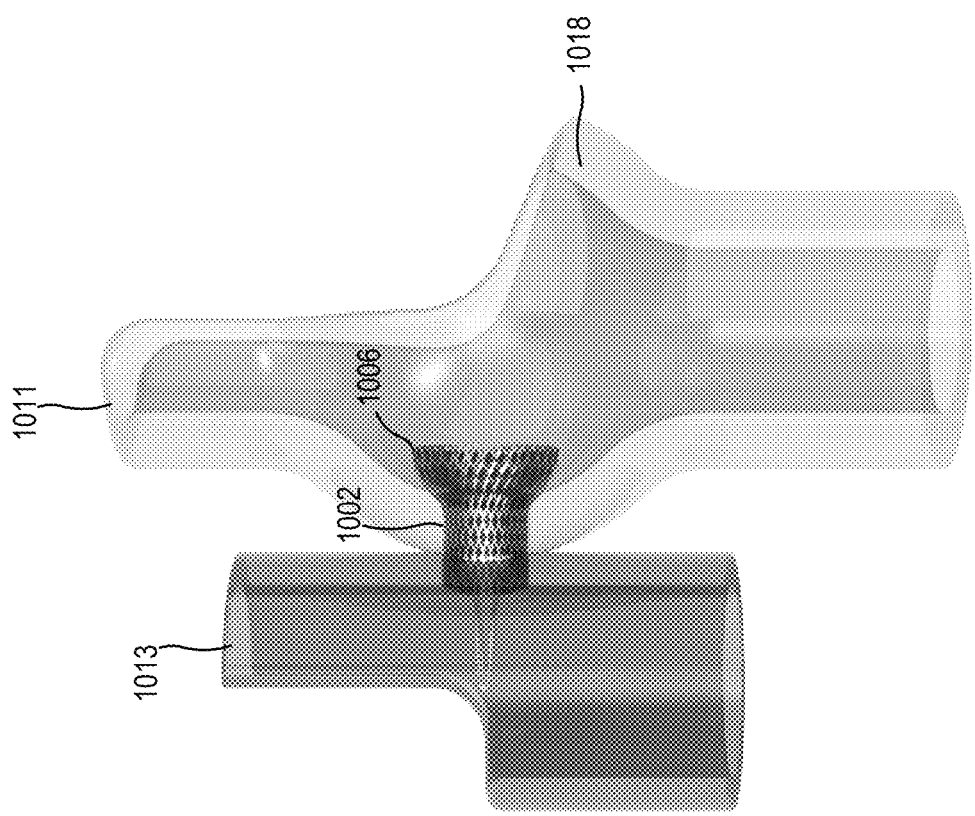
Figure 9C:
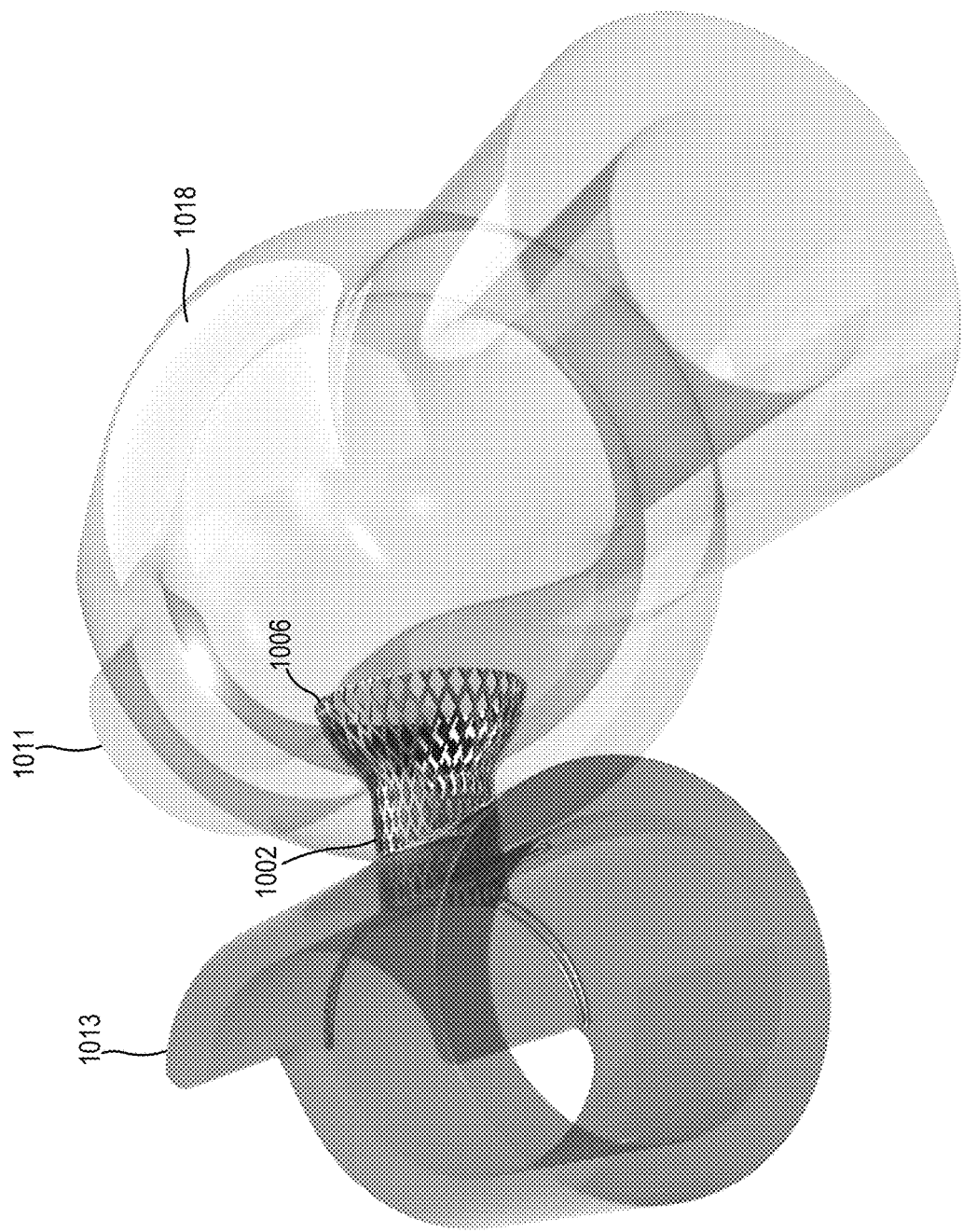
Figure 9D:
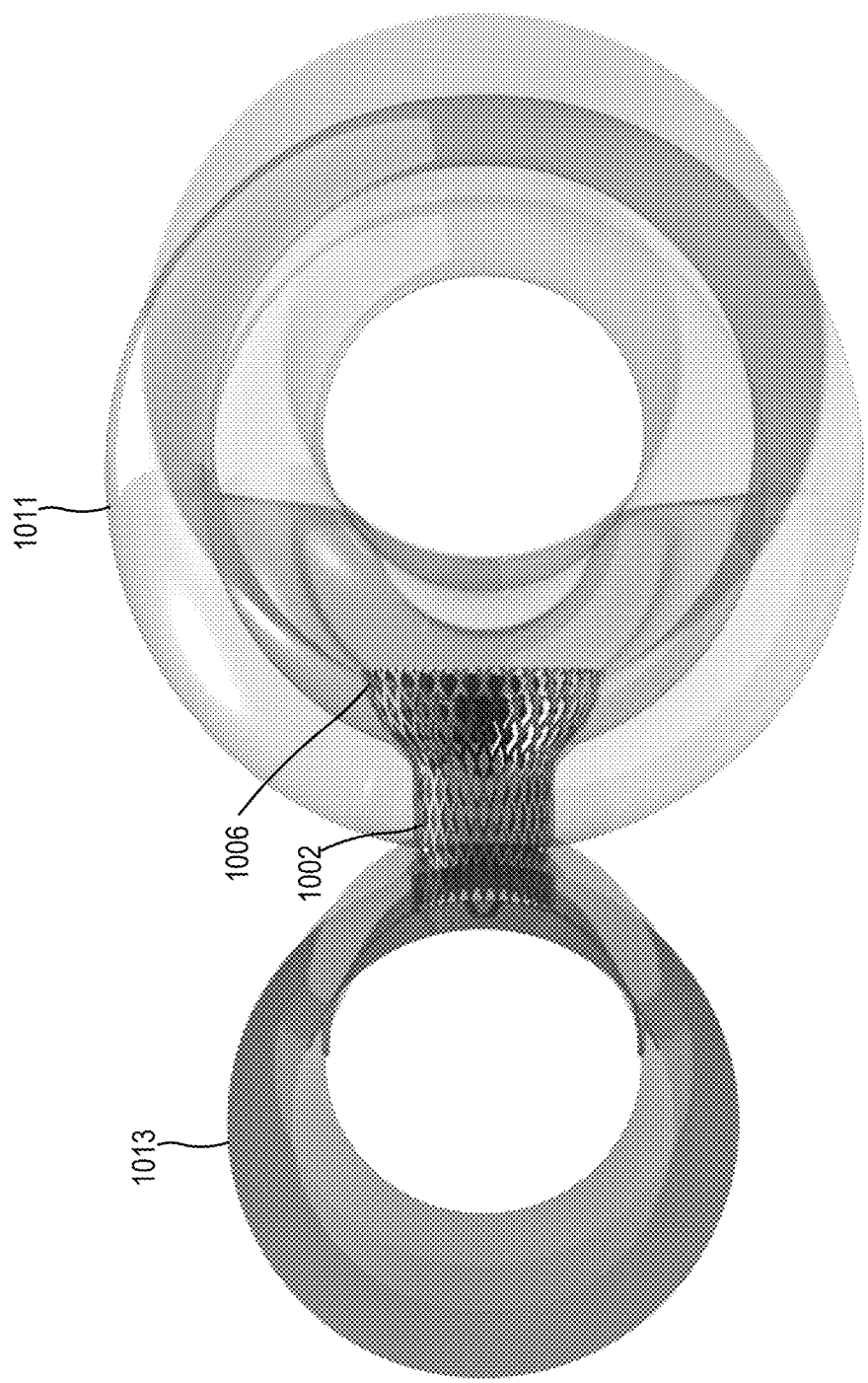

FIG. 8 shows a side view of a shunt 900 in the deployed configuration including a flow controller including a valve 907 and a filter 909, according to an embodiment. The valve 907 may be a one-way valve configured to enable blood to flow in a first direction (e.g., from the artery to the vein) but to prevent blood from flowing in a second direction (e.g., from the vein to the artery). In some embodiments, the valve may include a flexible material configured to respond to changes in blood pressure and flow dynamics. For example, the valve may open (or remain open) in response to blood pressure and/or blood flow in a first direction, whereas the valve may close (or remain closed) in response to a reverse in blood pressure and/or blood flow to prevent blood from flowing into the aneurysm sac. In some embodiments, in response to an increase in blood pressure and/or blood flow in the first direction, the valve may open to increase a flow rate and/or volume of blood therethrough. In some embodiments, in response to a decrease in blood pressure and/or blood flow as the aneurysm sac decreases in size and/or the endoleak decreases in severity, the valve may close to decrease a flow rate and/or volume of blood flow therethrough. As shown, the valve 907 may be disposed in a central portion 902 of the shunt 900 at or near a center point along a length of the shunt 900. The valve 907 may include a tubular member, and a proximal end of the tubular member may taper laterally such that a cross-sectional area defined by the tubular member decreases. In some embodiments, the tubular member may taper such that the proximal end of the tubular member defines a flat opening or slit. In some embodiments, the filter 909 of the flow controller may be cylindrical member including a plurality of walls disposed configured to catch blood clots and/or debris (e.g., from the thrombus) from flowing through the shunt 900 and toward the vein and into the systemic circulation. Alternatively or additionally, the filter 909 may include a mesh, net, a porous membrane, a semipermeable membrane, lattice, screen, etc. to prevent flow of solid matter through the filter 909.

FIGS. 9A-9G are illustrations of the shunt 1000 disposed between an artery 1011 and a vein 1013 to place the artery 1011 in fluid communication with the vein 1013 to treat an aneurysm, according to an embodiment. The shunt 1000 may be implanted in a portion of a wall of the artery 1011 that defines an aneurysm sac. As shown, the shunt 1000 is laser cut from a super-elastic material and defines a plurality of cells. The arterial sealing structure 1006 includes an elliptical cone shape (e.g., a cup, bulb, etc.) having an open distal end that extends toward a lumen of the artery 1011.

The central portion 1002 forms a cylindrical shape defining an inner lumen, which serves as the conduit for blood between vessels (e.g., between the aorta and the inferior vena cava). In the undeployed state, the central portion 1002 is compressed and constrained within a delivery catheter. Upon deployment, the central portion 1002 expands to a larger diameter, ensuring it fits securely within the apertures created in the walls of the aorta and vena cava. As shown, the venous sealing structure 1004 includes one or more stability members 1004A, 1004B, 1004C, 1004D (e.g., petaloids) coupled to the central portion 1002 and configured to conform to a curvature of an inner surface of a wall of the vein (e.g., the vena cava) 1013. In some embodiments, a first stability member 1004A may include a compliant projection configured to extend along at least a portion of a circumference of the inner surface of the vein wall 1013. A second stability member 1004B may include a compliant projection configured to extend along a length of the vein 1013 (e.g., extend straight or flat along the length of the vein 1013). In some embodiments, the compliant projection may include a biocompatible material, including but not limited to, a metal, a polymer, a plastic, an alloy, a fabric, etc. The one or more stability members 1004A, 1004B, 1004C, 1004D may help secure the shunt 1000 in place and/or prevent movement of the shunt 1000.

The arterial sealing structure 1006 (e.g., the elliptical cone shape) is configured to be positioned within the aorta, providing a stable anchor that prevents migration of the shunt 1000. In some embodiments, the arterial sealing structure 1006 may be expandable such that a distal end of the shunt 1000 remains securely positioned within the aorta under varying vein-to-artery geometries (for example, varying thrombus thicknesses), thus maintaining the integrity of the placement of the shunt 1000. As the arterial sealing structure 1006 expands within the aorta, it can push away any thrombus that may be present, thereby creating a clear drainage pathway for an endoleak. Furthermore, the arterial sealing structure 1006 includes a wide aperture or opening (e.g., at least 5 mm) to capture endoleaks from various intrasac locations such that the blood leaking into the aneurysm sac can be effectively drained into the inferior vena cava. The drainage pathway from a distal end of the shunt 1000 through the central portion 1002 can reduce the risk of aneurysm sac pressurization and potential rupture. The expansion of the arterial sealing structure 1006 may also generate an opposing force directed towards the proximal stability members 1004A, 1004B, 1004C, 1004D (e.g., the petaloids). This opposing force may compress the puncture sites (e.g., move the puncture sites toward one another) in the walls of both the vena cava and the aorta. By exerting pressure in the direction opposite to the proximal stability members 1004A, 1004B, 1004C, 1004D, the arterial sealing structure 1006 can help create an effective arteriovenous seal, which can help direct blood to flow through the shunt 1000 and can prevent leakage through the puncture sites to an extravascular space. When the aneurysm shrinks and causes the arterial sealing structure 1006 to contact the endograft, the shape of the arterial sealing structure 1006 promotes or ensures protection of the endograft. For example, the elliptical cone shape of the arterial sealing structure 1006 may distribute a force applied by the shunt 1000 to the endograft to be evenly distributed and may prevent localized stress on the endograft. This protection can promote or maintain the integrity of the endograft and limit or prevent complications related to endograft damage.

The shunt 1000 may enable secure anchoring within the vascular system. The stability members 1004A, 1004B, 1004C, 1004D of the venous sealing structure 1004 are configured to lay flush against the interior surface of the vena cava. In some embodiments, the stability members 1004A, 1004B, 1004C, 1004D and can be heat-set in a curved form to create a saddle-shaped deployed configuration. The deployed configuration may comply with an inner geometry of the vessel, providing a secure fit. For example, in the deployed configuration the petaloids to lay flush against the interior surface of the vena cava, ensuring a secure and stable anchoring mechanism, as shown in FIG. 9E. Dimensions of the saddle-shaped configuration of the petaloids can be specifically tailored to conform to the inner geometry of the vessel, providing a customized fit that enhances the stability of the shunt 1000.

The shunt 1000 and any other shunt described herein may be formed from a single tube of a material, such as nitinol, spring steel, glass or carbon composites or polymers, or pseudoelastic (at body temperature) material such as nitinol or comparable alloys and polymers, by laser cutting several closed-ended slots along the length of the tube (leaving the extreme distal and proximal edges of the tube intact) and cutting open-ended slots from the longitudinal center of the tube through the distal and proximal edges of the tube During deployment, the stability members 1004A, 1004B, 1004C, 1004D may be oriented such that at least a first pair of stability members 1004A, 1004C align with a curved surface of the vein and at least a second pair of stability members 1004B, 1004D align parallel or substantially parallel to a longitudinal axis of the vein. The pre-set curved petaloids expand and lay flush against the interior surface of the vena cava, forming a saddle-shaped configuration.

Advantages of the shunt 1000 may include providing a secure anchoring mechanism, being adaptable, improving patient outcomes, and being biocompatible and/or durable. For example, the combined use of the arterial sealing structure 1006 and proximal stability members 1004A, 1004B, 1004C, 1004D ensures a stable and secure anchoring mechanism. The saddle-shaped configuration of the stability members 1004A, 1004B, 1004C, 1004D provides a customized fit within the vena cava, enhancing the stability of the shunt 1000 and preventing migration. The ability of the central portion 1002 to expand and/or shorten upon release from the catheter allows the shunt 1000 to adapt to varying vessel diameters. This adaptability ensures a secure fit, accommodating the dynamic nature of the vascular system. By reducing pressure and providing a drainage pathway for endoleaks within the aneurysm sac, the shunt 1000 effectively prevents rupture, improving patient outcomes and reducing the need for long-term surveillance and potential reinterventions associated with traditional EVAR procedures. The use of biocompatible materials and precise laser-cutting techniques allow the shunt 1000 to be safe for long-term implantation, and the durable construction minimizes the risk of adverse reactions and complications, promoting better long-term patient outcomes.

In some embodiments, the shunt 1000 can be implanted in locations other than between vein and artery, and although referred to as the arterial sealing structure 1006 and the venous sealing structure 1004A-1004D, it should be appreciated the arterial sealing structure 1006 and venous sealing structure 1004A-1004D can be configured for other parts of the anatomy (e.g., other than the aorta).

FIGS. 10A-10B show the delivery system 1150 including a catheter 1160 for delivering a shunt 1100 to treat an aortic aneurysm, according to an embodiment. In some embodiments, the delivery system 1150 includes a catheter handle 1168 and a catheter shaft 1160, extending therefrom, and having a catheter lumen therein. A sliding sheath 1166 may be disposed in the catheter lumen, and the shunt 1100 may be detachably coupled to the sliding sheath 1166. The sliding sheath 1166 may be configured to slide over a dilator 1164 including a dilator tip 1165. A guidewire 1162 may be disposed through a lumen defined by the dilator 1164 and configured to guide navigation of a distal end of the delivery system 1150. In some embodiments, the catheter shaft 1160 is steerable (e.g., a steerable sheath). As shown in FIG. 10A, a distal portion of the steerable catheter shaft 1160 may be configured to move through multiple positions. In some embodiments, the catheter handle 1168 includes a hemostatic valve 1172 at a proximal end of the catheter handle 1168. In some embodiments, the catheter handle 1168 includes a rotation collar 1174 for steering the catheter shaft 1160. In some embodiments, the delivery system 1150 comprises a contrast port 922 coupled to the catheter handle 1186. In some embodiments, the catheter handle 1168 includes a tip rotation indicator 1173 to determine a rotation of the dilator tip 1165.

In some embodiments, the catheter 1160 includes one or more catheter radiopaque markers 1161. In some embodiments, the catheter 1160 includes between about 1 radiopaque marker and 10 radiopaque markers, inclusive of all ranges and subranges therebetween. In some embodiments, one or more radiopaque markers are disposed at the distal end of the catheter shaft 1160. In some embodiments, the one or more catheter radiopaque markers 1161 include a radiopaque band disposed around the catheter shaft 1160. In some embodiments, the catheter shaft 1160 has a length in a range of about 10 cm to about 100 cm, inclusive of all ranges and subranges therebetween. In some embodiments, the catheter shaft 1160 includes a catheter wall forming an inner diameter and an outer diameter. In some embodiments, the inner diameter of the catheter shaft 1160 is in a range of about 0.5 cm to about 2 cm, inclusive of all ranges and subranges therebetween. In some embodiments, the outer diameter of the catheter is in a range of about 0.5 cm to about 2 cm, inclusive of all ranges and subranges therebetween.

In some embodiments, the proximal end of the catheter shaft 1160 is operably connected to the catheter handle 1168. In some embodiments, the position of the catheter shaft 1160 inside the blood vessel (e.g., artery or vein) may be controlled by a user (e.g., a surgeon, a medical specialist, a doctor, or similar) or by a machine (e.g., a robotic arm). In some embodiments, the position of the catheter shaft 1160 inside the blood vessel is controlled using the catheter handle 1168. In some embodiments, the catheter handle 1168 includes a release mechanism operably linked to any one or more of the guidewire 1162, dilator 1164 the sealing structures (1104, 1106), the shunt 1100, the sliding sheath 1166, or the catheter shaft 1160. In some embodiments, the catheter handle 1168 is configured to orient the direction of any one or more of the guidewire 1162, the dilator 1164, the sliding sheath 1166, or the shunt 1100.

In some embodiments, the guidewire 1162 is configured to pass through a dilator 1164. In some embodiments, the guidewire 1162 includes a proximal end and a distal end. The guidewire 1162 may additionally include a guidewire lumen traversing the length of the guidewire 1162 from the proximal end to the distal end. In some embodiments, the guidewire 1162 (and the guidewire lumen) has a length in a range of about 10 cm to about 250 cm, inclusive of all ranges and subranges therebetween. In some embodiments, the guidewire may have a guidewire wall forming an inner diameter and an outer diameter. In some embodiments, the inner diameter of the guidewire is in a range of about 0.1 mm to about 3 mm, inclusive of all ranges and subranges therebetween. In some embodiments, the outer diameter of the guidewire outer diameter is in a range of about 0.1 mm to about 3 mm, inclusive of all ranges and subranges therebetween.

In some embodiments, the guidewire 1162 is introduced within the dilator 1164 via a guidewire introduction port 1163. In some embodiments, the dilator 1164 includes one or more depth markings 1167, configured to indicate a distance the dilator 1164 extends from a point of reference (e.g., a distal end of the catheter handle 1168). In some embodiments, the dilator 1164 body serves as a support member. In some embodiments, the dilator tip 1164 is configured to be rotated (bent, deflected, etc.) to dilate an opening at the venous and/or arterial puncture site. In some embodiments, the dilator tip 1165 is configured to be rotated via the catheter handle 1168. In some embodiments, the shunt 1110 and the dilator 1164 are detachably attached.

In some embodiments, the dilator 1164 includes one or more dilator radiopaque markers. In some embodiments, the dilator 1164 includes between about 1 radiopaque marker and 10 radiopaque markers, inclusive of all ranges and subranges therebetween. In some embodiments, the radiopaque markers on the dilator 1164 are disposed at the distal end of the dilator 1164, proximal to the dilator tip 1165. In some embodiments, the dilator 1164 has a length in a range of about 10 cm to about 100 cm, inclusive of all ranges and subranges therebetween. In some embodiments, the dilator 1164 includes a wall forming an inner diameter and an outer diameter. In some embodiments, the inner diameter of the dilator 1164 is in a range of about 0.1 mm to about 5 mm, inclusive of all ranges and subranges therebetween. In some embodiments, the outer diameter of the dilator 1164 is in a range of about 1 mm to about 5 mm, inclusive of all ranges and subranges therebetween.

In some embodiments, the sliding sheath 1166 is configured to slide over the dilator 1164. In some embodiments, the sliding sheath 1166 is configured to be detachably coupled to the shunt 1100 at a distal end portion of the sliding sheath 1166. In some embodiments, the sliding sheath 1166 may include be disposed in an inner diameter of the shunt 1100. In some embodiments, the sliding sheath 1166 includes a braided shaft (e.g., includes a plurality of filaments braided into a shaft). In some embodiments, the sliding sheath 1166 is configured to maintain the sealing structures 1104, 1106 in a non-deployed state (e.g., the delivery configuration) until the sliding sheath 1166 is withdrawn. In some embodiments, the sliding sheath 1166 is moved proximally to transition the sealing structures 1104, 1106 to the deployed configuration. In some embodiments the sliding sheath 1166 may include one or more bias members (e.g., an inflatable balloon) disposed at or near a distal end of the sliding sheath 1166. In some embodiments, the sliding sheath 1166 may include an inflation port at a proximal end of the sliding sheath 1166 configured to supply a medium (e.g., gas or liquid) to the inflatable balloon to inflate the balloon. In some embodiments, inflating the balloon may expand the shunt 1100 from the delivery configuration (e.g., compressed configuration) to the deployed configuration and/or to controllable decouple the shunt 1100 from the sliding sheath 1166.

In some embodiments, the delivery system 1150 described herein may include one or more (e.g., 1, 2, 3, 4, 5, 6, 7, 8, 9, or 10) steerable access catheters, one or more (e.g., 1, 2, 3, 4, 5, 6, 7, 8, 9, or 10) guidewires, one or more (e.g., 1, 2, 3, 4, 5, 6, 7, 8, 9, or 10) dilators, one or more sliding sheaths, and one or more (e.g., 1, 2, 3, 4, 5, 6, 7, 8, 9, or 10) shunts.

Figure 11:
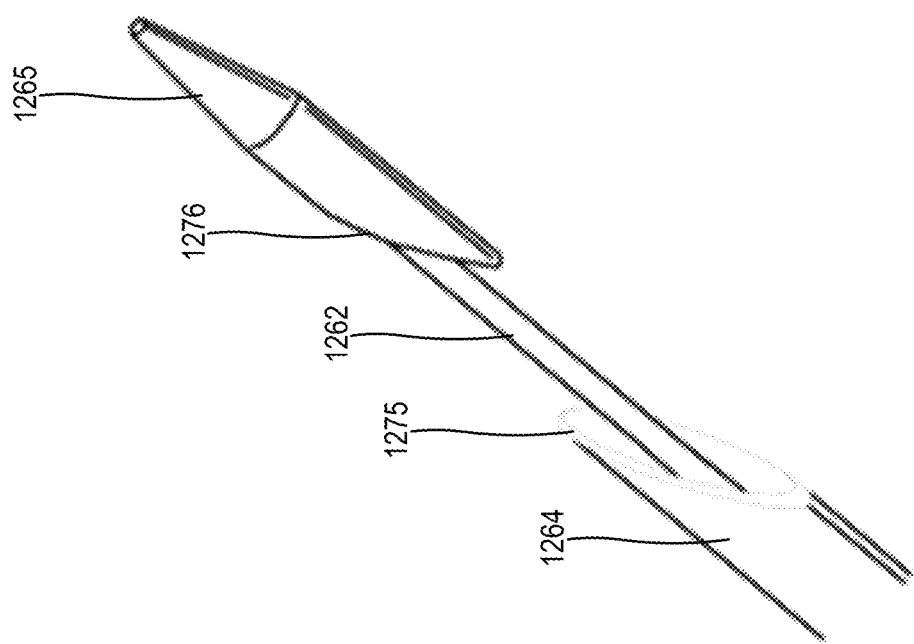
FIG. 11 is an illustration of a distal tip for cutting an opening in the vasculature such that the shunt may be disposed therethrough, according to an embodiment.

FIG. 11 is an illustration of a distal tip for cutting an opening in the vasculature (e.g., the vein and/or artery) such that the shunt (e.g., any of the shunts described herein) may be disposed therethrough, according to an embodiment. The delivery system may include a cutting mechanism configured to cut through two vessel walls to create an anastomosis (e.g., to place the two vessels in fluid communication). In some embodiments, the cutting mechanism may be structurally and/or functionally similar to the cutting mechanism described in FIG. 4, therefore, certain aspects of the cutting mechanism are not described herein with respect to FIG. 11. The catheter (e.g., the dilator 1264) may track over a guidewire (not shown) which has been positioned through a first vessel, such as the inferior vena cava (IVC), and into a second vessel, such as the aorta, or more broadly between any two vascular structures. The distal tip of the catheter 1264 has a dilating tip 1265, which allows the catheter 1264 to advance easily through the vessel walls. At a proximal end of the distal tip, the catheter 1264 reduces in diameter (e.g., tapers) to a bladed edge (e.g., the first cutting edge). As shown, the first cutting edge 1276 may form an oval shape, meaning the edge tapers at a diagonal. The catheter 1264 further may include a blunt surface (and/or a second cutting edge) corresponding to the first cutting edge positioned along the catheter 1264 proximal to the first cutting edge 1276. As the catheter 1264 is tracked over the guidewire, the tapered distal tip easily passes into an adjacent vessel. The distal tip, may be configured to retract, capturing the walls of the two vessels between the bladed surface and the blunt surface. The distal tip 1265 and the body of the dilator 1264 may each be coupled to a shaft configured to move the distal tip distally and/or proximally such that the first cutting edge 1276 moves toward the blunt surface 1275. A predetermined pressure may be applied between the two surfaces to cut out a small circular section of the aorta and the IVC.

Figure 12:
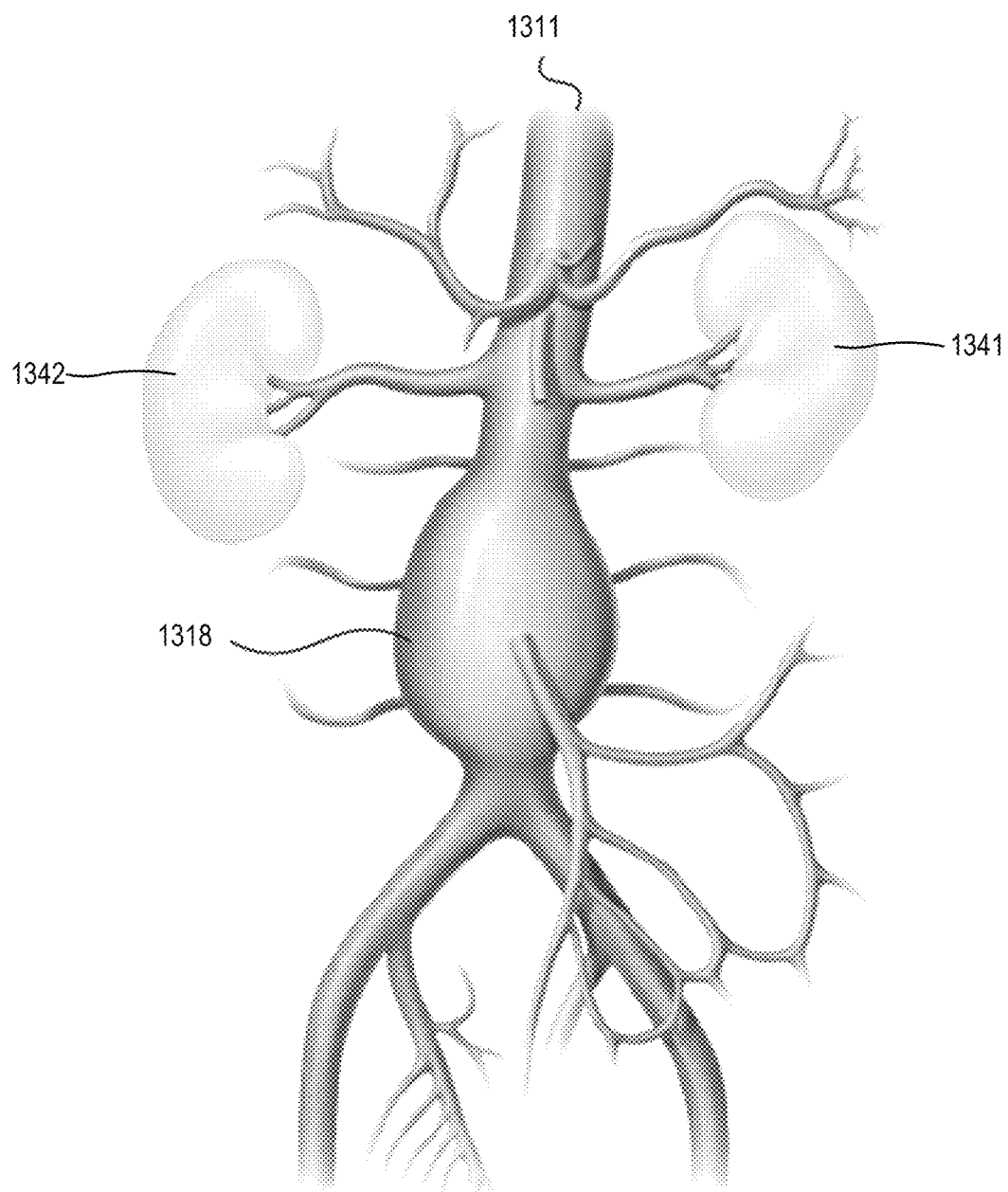
FIG. 12 is an illustration of an abdominal aortic aneurysm showing the aneurysm sac, the right kidney, the left kidney, and arterial vessels that branch out from the aorta.
Figure 13A:
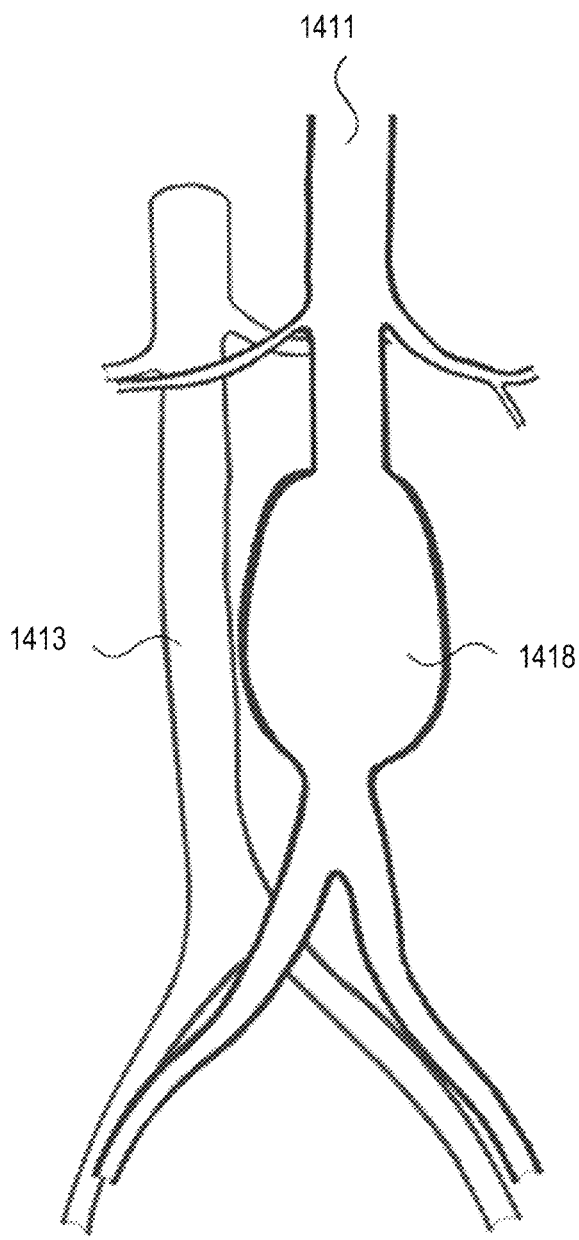
FIG. 13A is a schematic of the abdominal aortic aneurysm showing the aneurysm sac.
Figure 13B:
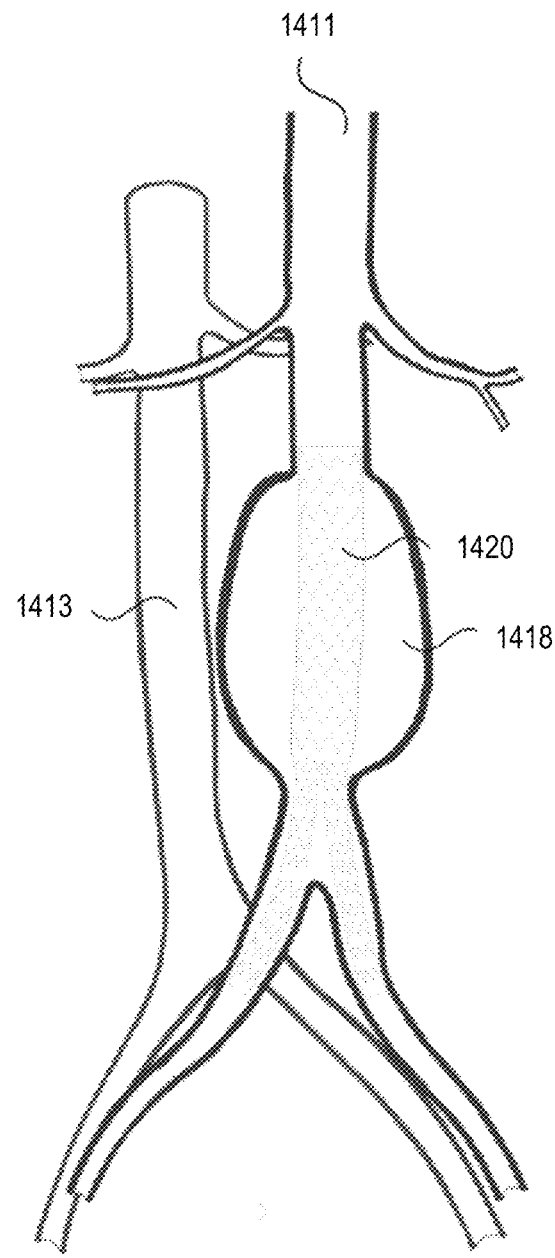
FIG. 13B is a schematic of an endograft implanted in the aneurysm sac to treat or alleviate the abdominal aortic aneurysm, according to an embodiment.
Figure 13C:
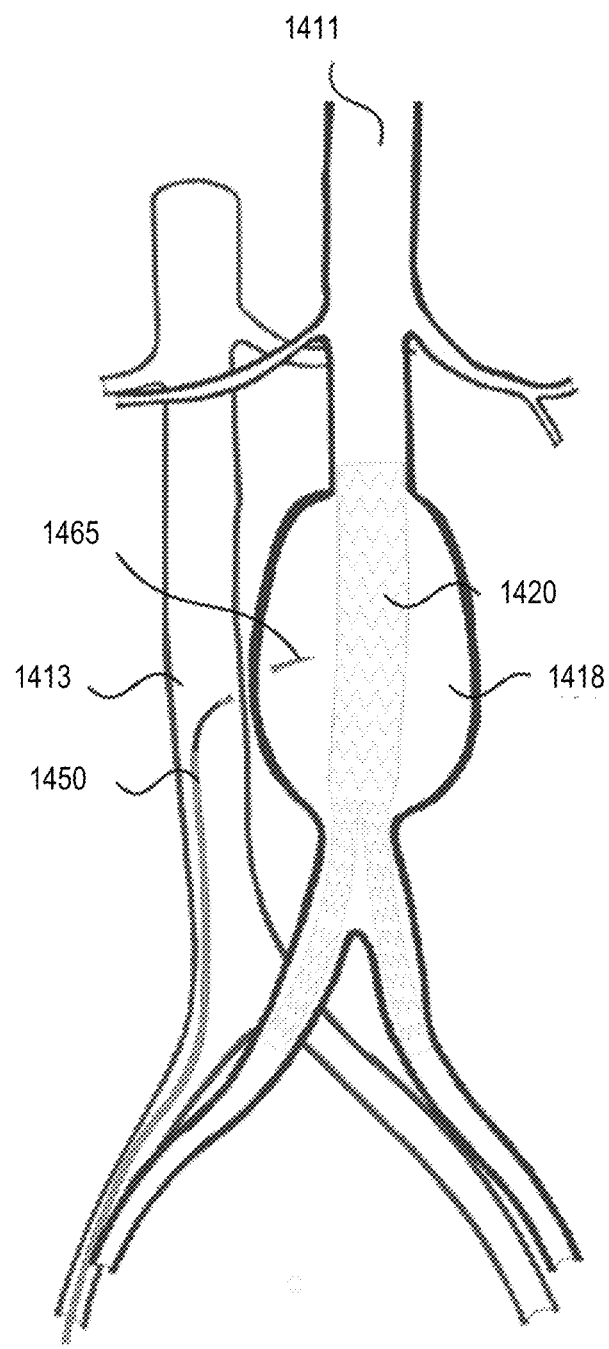
FIG. 13C is a schematic of a distal end of a delivery system puncturing the vena cava and the aorta to treat an aortic aneurysm, according to an embodiment.
Figure 13D:
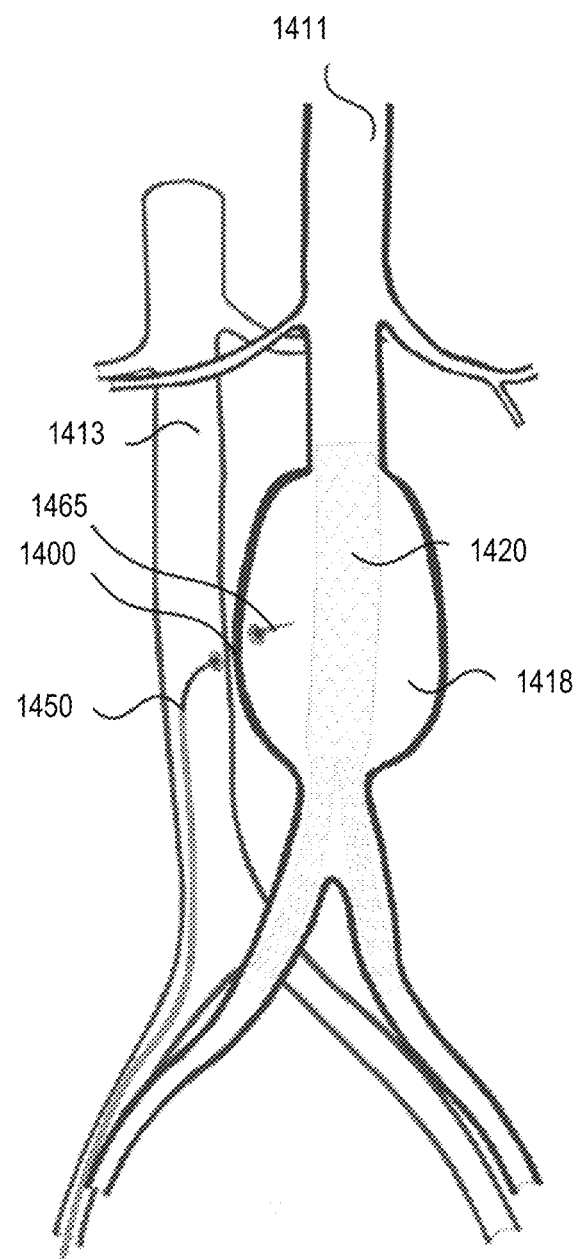
FIG. 13D is a schematic of the shunt being deployed transcavally to place the aorta in fluid communication with the vena cava, according to an embodiment.
Figure 13E:
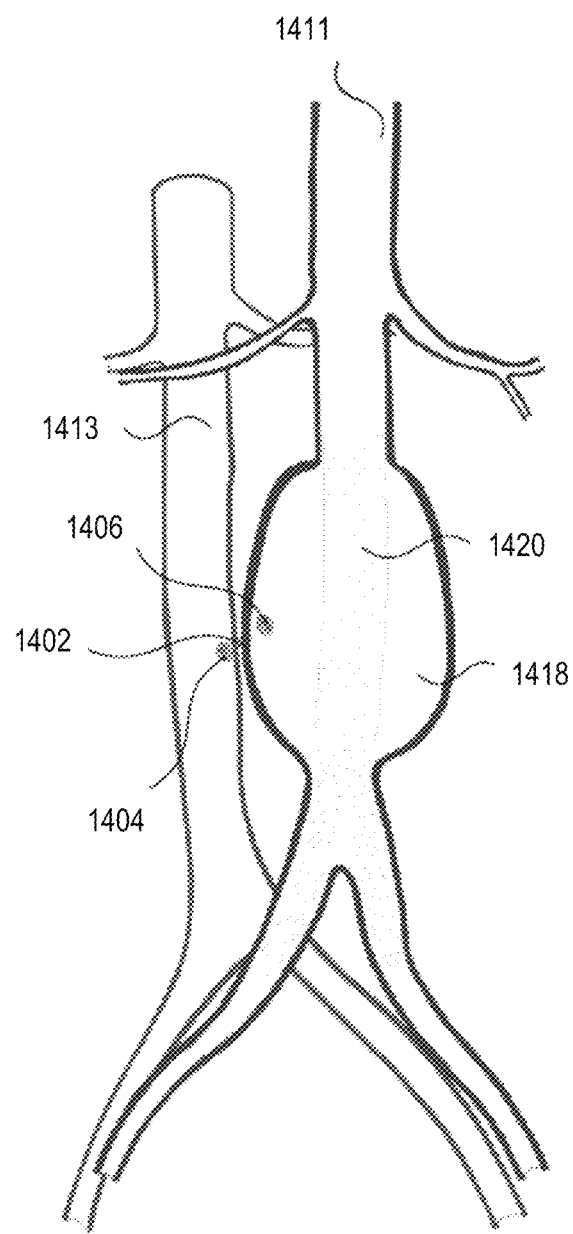
FIG. 13E is a schematic of the shunt in a deployed configuration implanted transcavally between the aorta and the vena cava, according to an embodiment.
Figure 13F:
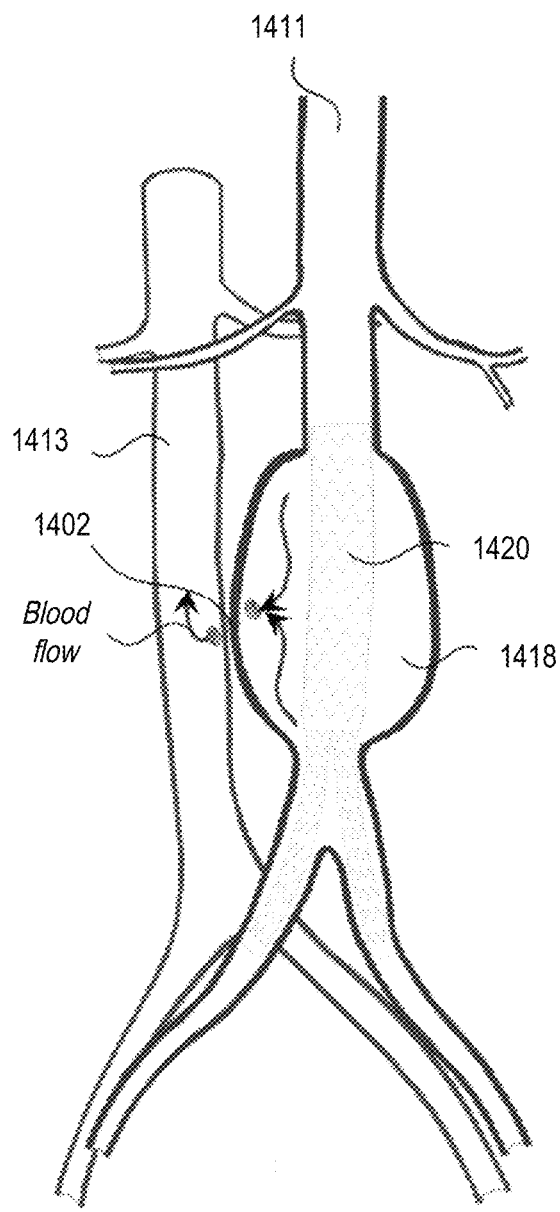
FIG. 13F is a schematic of the shunt in the deployed configuration implanted transcavally to allow blood to flow from the aorta to the vena cava, according to an embodiment.

FIG. 12 is an illustration of an abdominal aortic aneurysm showing the aneurysm sac 1318, the right kidney 1341, the left kidney 1342, and arterial vessels that branch out from the aorta 1311. FIG. 13A-13E are illustrations of an example method for implanting the shunt 1400, according to an embodiment. As shown in FIG. 13A the aneurysm sac 1418 is located along the aorta 1411, and the vena cava 1413 is adjacent to the aorta 1411. As shown in FIG. 13B, an endograft 1420 may be implanted in the aneurysm sac 1418 to treat the abdominal aortic aneurysm. The endograft mat be placed as an initial treatment for an aortic aneurysm (e.g., abdominal aortic aneurysm), wherein the fluid (e.g., blood) flows entirely through the endograft 1420, thereby alleviating pressure build-up and stress against the aortic wall at the aneurysm. In some cases, however, one or more leaks may form about the endograft 1420, such that fluid (e.g., blood) builds up at the aneurysm site (e.g., aneurysm sac 1418), and potentially resulting in further stress and/or rupture of the aortic wall. For example, type 2 endoleaks are the most common type of endoleak and are described as a refilling of the aortic sac 1418 via branches such as lumbar arteries (LAs), inferior mesenteric artery (IMA), median sacral artery, or accessory renal arteries. Accordingly, in some cases, providing a shunt between the artery (e.g., aorta 1411) and vein (e.g., vena cava 1413) will help to drain fluid (e.g., blood) being collected within the aneurysm sac 1418 to alleviate further progression of the aneurysm and potential rupture. As shown in FIG. 13C, a delivery system 1450 including a dilator with a dilator tip 1465 at a distal end of the delivery system 1450 is navigated through the vena cava 1413 toward the aneurysm sac 1418. In some embodiments, a guidewire of the delivery system 1450 may be configured to puncture the vena cava 1413 and then puncture the aorta 1411 to create a path through which the dilator may be disposed. In some embodiments, the dilator tip 1465 may be used to expand a size of a puncture site at the vena cava 1413 and a puncture site at the aorta 1411. As shown in FIG. 13D-13E, the shunt 1400 is deployed transcavally such that a venous sealing structure 1404 is positioned in the vena cava 1413, an arterial sealing structure 1406 is positioned in the aneurysm sac 1418, and a central portion 1402 of the shunt 1400 spans across the extravascular space between the vena cava 1413 and the aorta 1411. The catheter may be removed such that blood can flow out of the aorta. The shunt 1400 places the aorta (e.g., the aneurysm sac 1418) in fluid communication with the vena cava 1413 such that blood may flow from the aneurysm sac 1418, through the shunt 1400, and into the vena cava 1413, as shown in FIG. 13F.

Figure 14A:
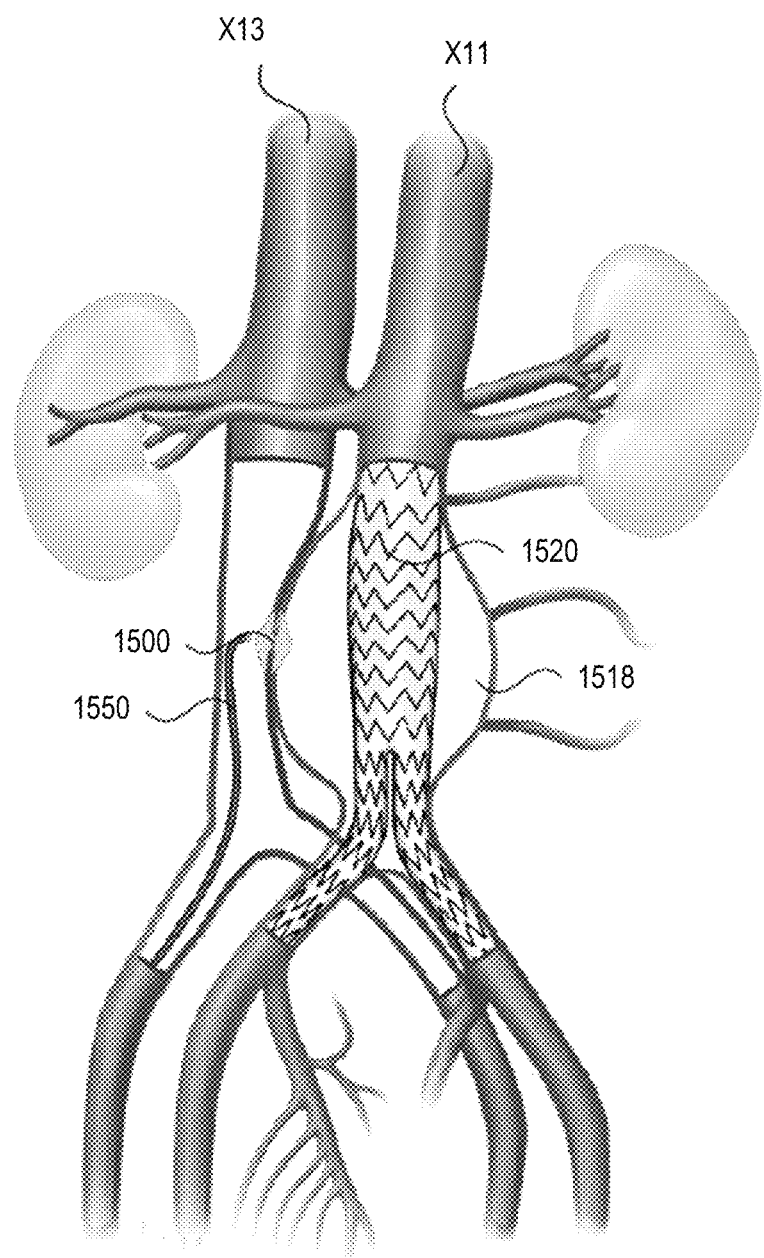
FIGS. 14A-14B are illustrations of the shunt in the deployed configuration implanted transcavally to allow blood to flow from the aorta to the vena cava, according to an embodiment
Figure 14B:
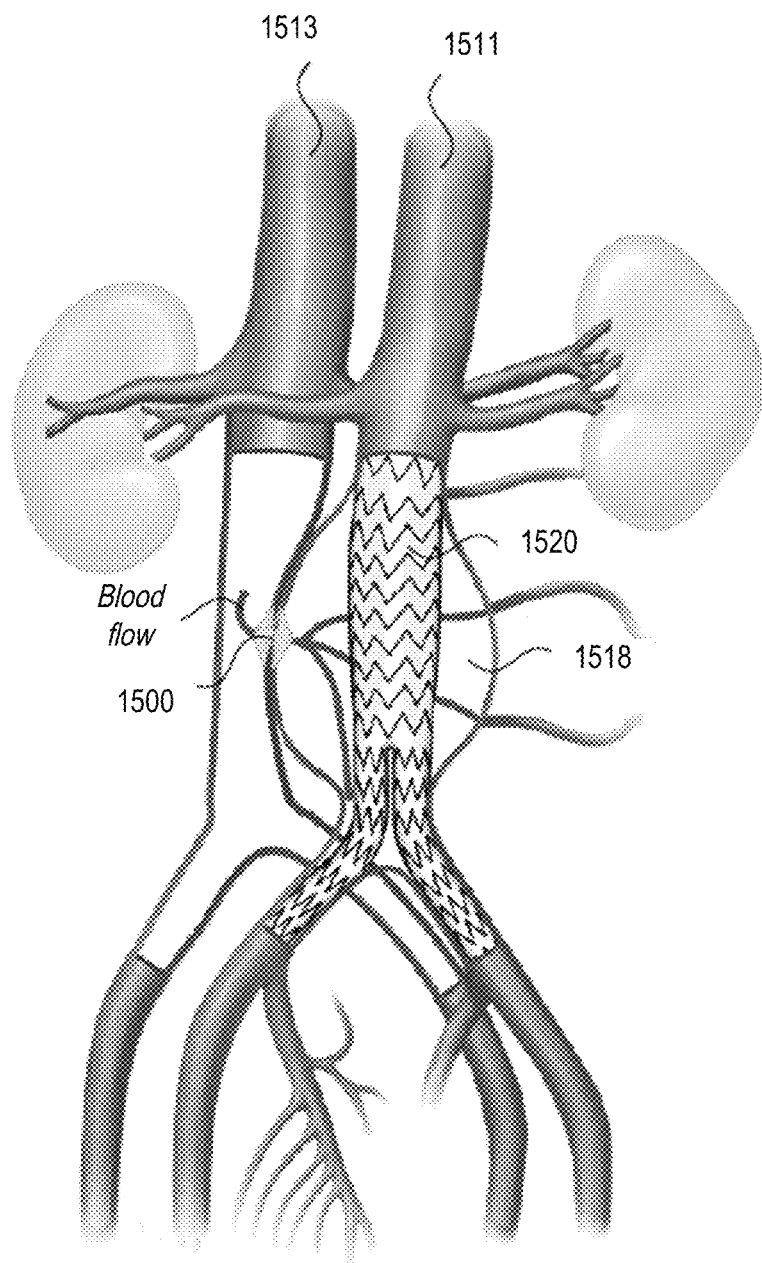

FIGS. 14A-14B are illustrations of the shunt 1500 in the deployed configuration implanted transcavally to allow blood to flow from the aorta 1511 to the vena cava 1513, according to an embodiment. As shown, the shunt 1500 is implanted transcavally such that blood may flow out of the aneurysm sac 1518, wherein the aorta wall at the aneurysm site 1418 abuts the wall of the vena cava.

Figure 15:
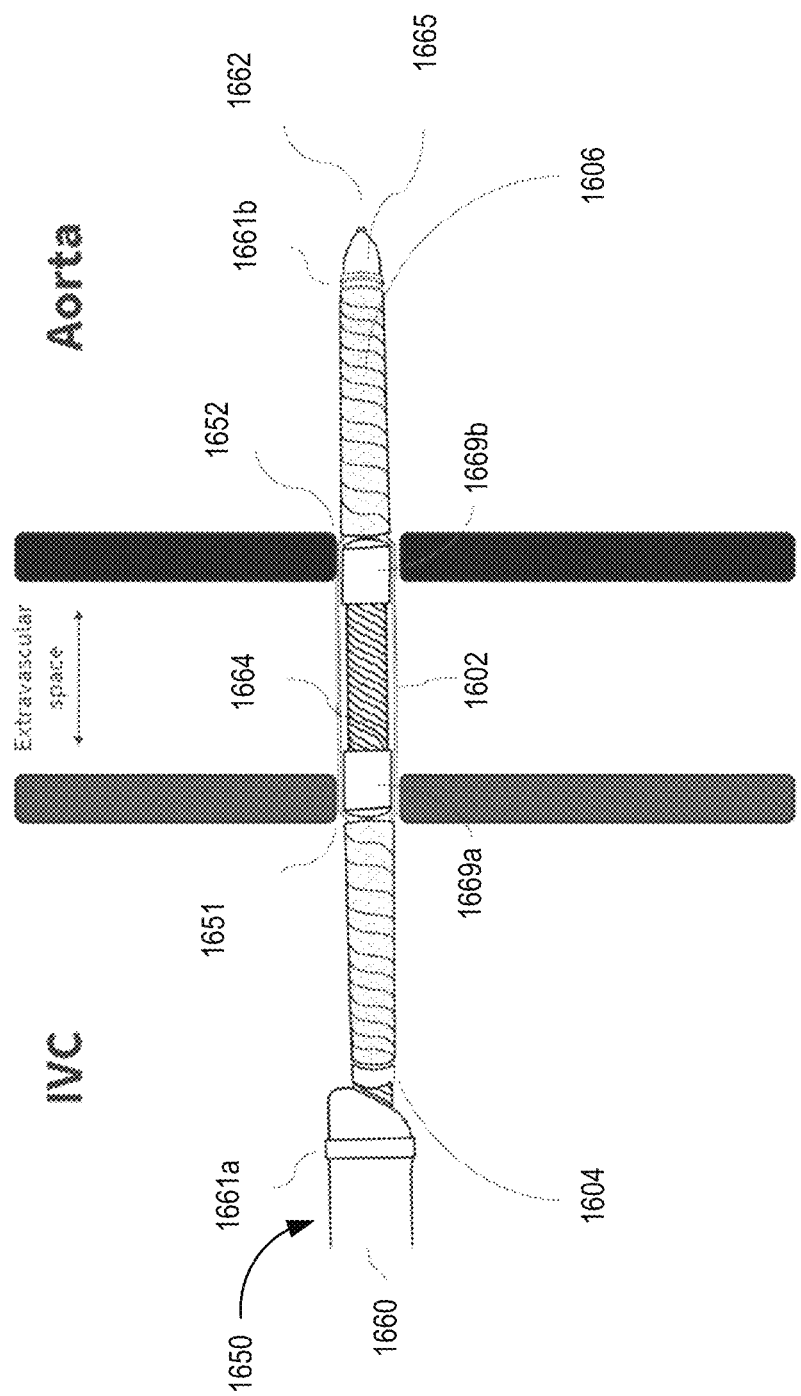
FIG. 15 is a diagram of a distal end of a delivery system disposed through a venous puncture site and an arterial puncture site with the a in a delivery configuration disposed therein, according to an embodiment.

FIG. 15 is an illustration of a distal end of a delivery system 1650 disposed transcavally during implantation of a shunt 1600, according to an embodiment. As shown, the delivery system 1650 includes a catheter 1660 (e.g., steerable catheter) including a radiopaque marker 1661a on a distal end of the catheter 1660. A dilator 1664 is disposed in a lumen of the catheter 1660 and configured to extend from the distal end of the catheter. The dilator 1664 defines a lumen in which a guidewire 1662 may be disposed and further includes a distal tip 1665 through which the guidewire 1662 may extend. The shunt may be disposed around the dilator and coupled to the dilator 1664 via a proximal attachment point 1169*a* and a distal attachment point 1669*b*. As shown, the dilator 1664 is moved through a venous puncture site 1651 and an arterial puncture site 1652 such that a venous sealing structure 1604 of the shunt is positioned in the vena cava, an arterial venous sealing structure 1606 of the shunt is positioned in the aorta, and a central portion 1602 of the shunt spans the extravascular space. In some embodiments, the arterial sealing structure 1606 (e.g., the distal end of the shunt) may include one or more radiopaque markers 1661*b*.

Figure 16:
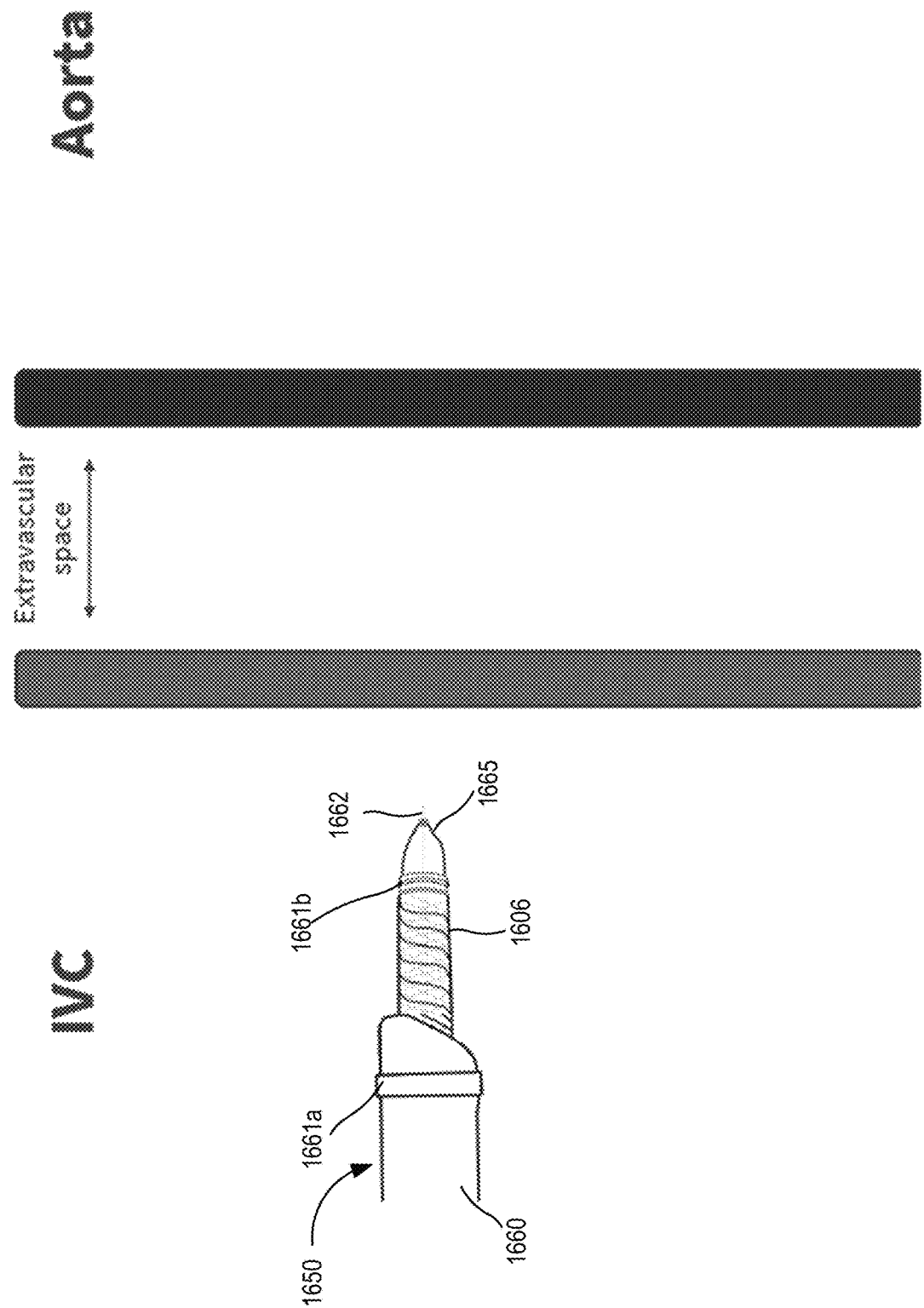
FIG. 16 is a diagram of the distal end of a delivery system of FIG. 15 extending toward a target puncture site on a wall of the vena cava, according to an embodiment.
Figure 17:
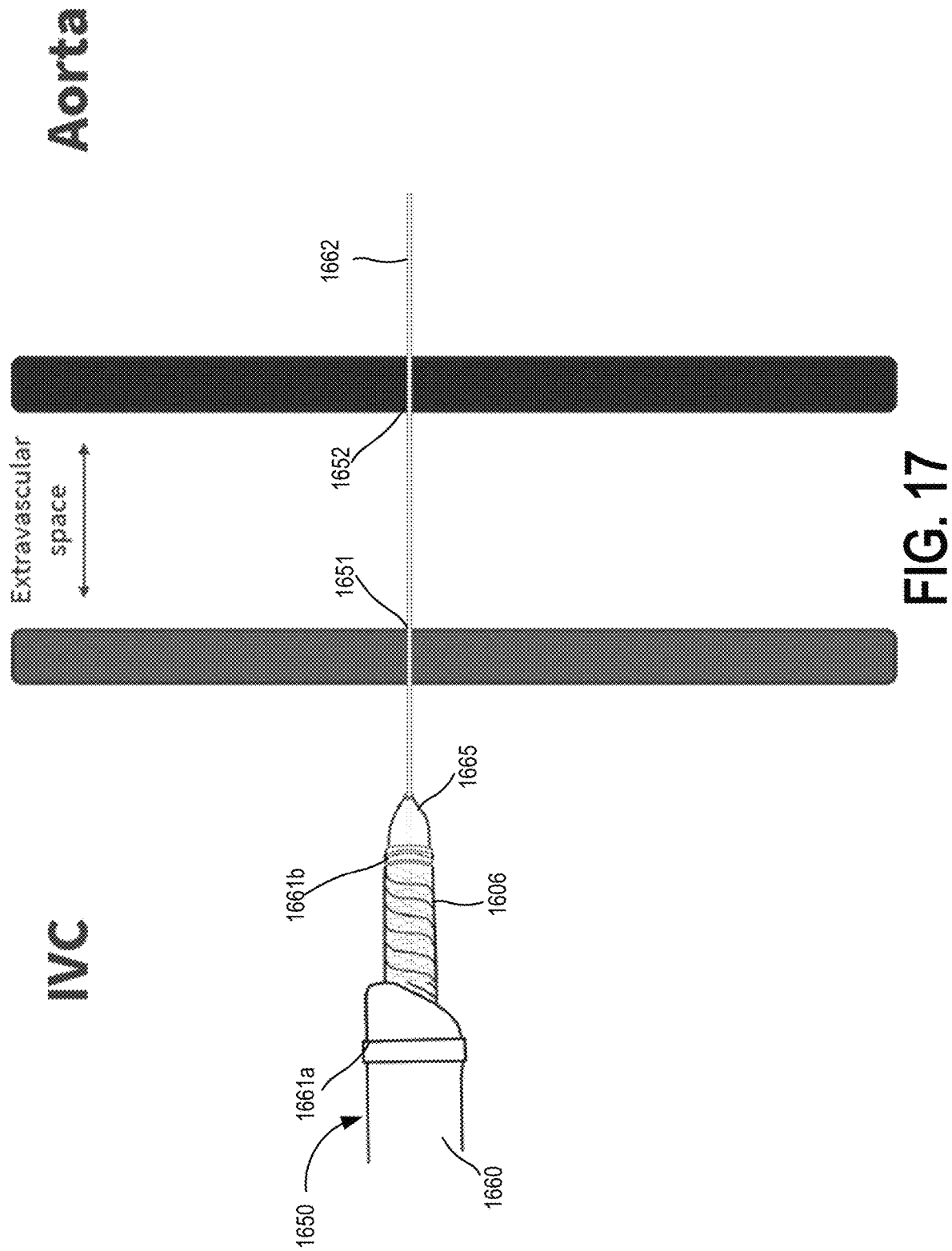
FIG. 17 is a diagram of the distal end of the delivery system of FIGS. 15-16 puncturing the vena cava and the aorta with a guidewire, according to an embodiment.
Figure 18:
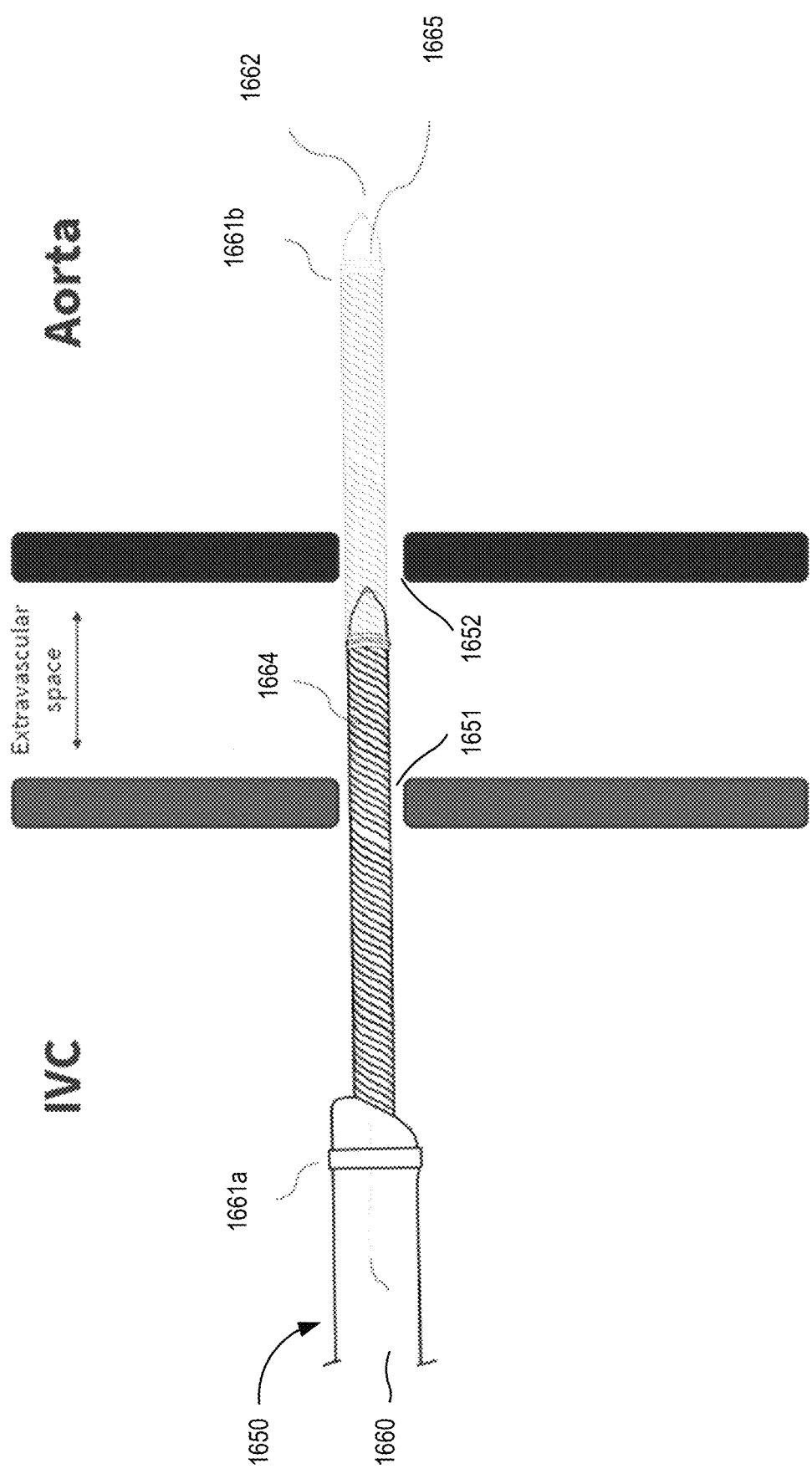
FIG. 18 is a diagram of a dilator tip of the distal end of the delivery system of FIGS. 15-17 dilating a venous puncture site and arterial puncture site created by the guidewire, according to an embodiment.
Figure 19:
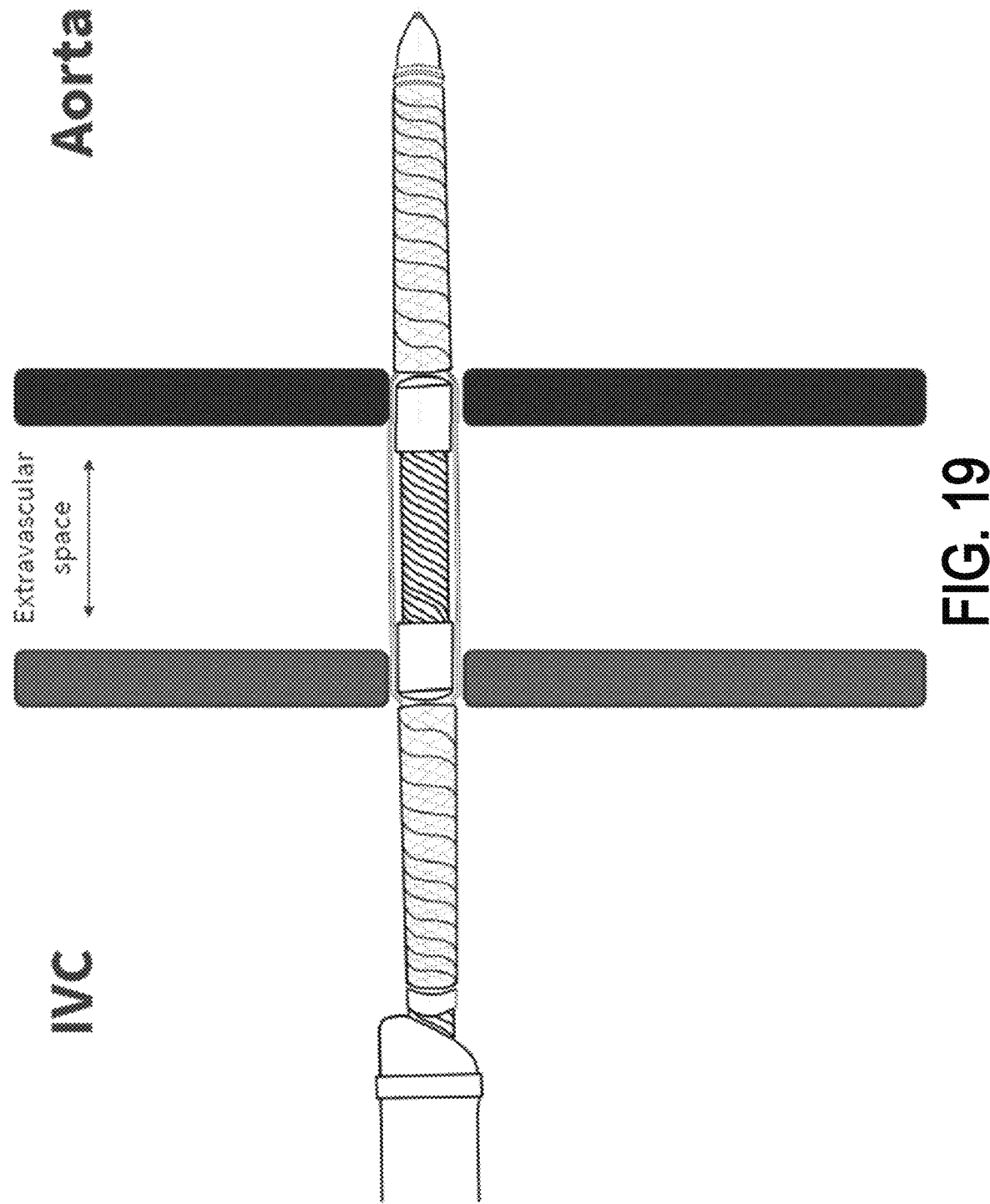
FIG. 19 is a diagram of the dilator body including the shunt being disposed through the venous puncture site and the arterial puncture site to position the shunt between the vena cava and the aorta, according to an embodiment.

FIGS. 16-28 shows an example method of deploying a shunt transcavally to place the aorta in fluid communication with the vena cava, according to an embodiment. In some embodiments, said method for implanting the shunt may occur contemporaneous or substantially contemporaneous with when an endograft is implanted to treat an aneurysm, as a preventive care means in the event a leak occurs across the endograft. In some embodiments, said method for implanting the shunt occurs after the endograft has been implanted, as a preventive care means or as a remedial response to the leakage of fluid into the sac of an aortic aneurysm. As shown in FIG. 16, the distal end of the delivery system 1650 is positioned near a target venous puncture site. Then, the guidewire 1662 moves distally to define the venous puncture site 1651 and the arterial puncture site 1652, as shown in FIG. 17. After the initial puncture sites 1651, 1652 are defined, the dilator 1664 may be moved through the venous puncture site 1651 to expand the venous puncture site 1651, as shown in FIG. 18. Subsequently, the dilator 1664 may be moved through the arterial puncture site 1652 to expand the arterial puncture site 1652, as shown in FIG. 19.

Figure 20:
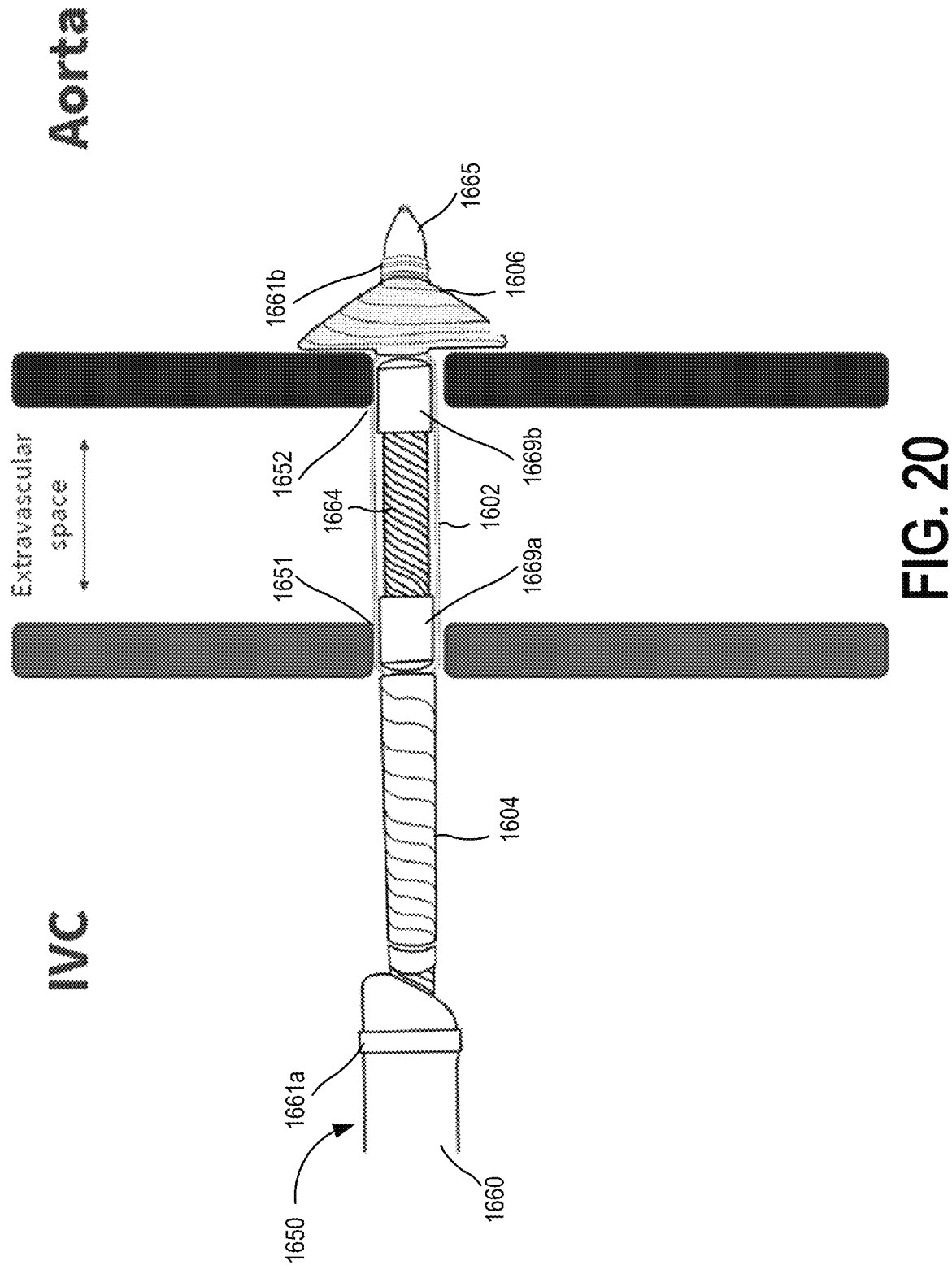
FIG. 20 is a diagram of a distal end of the shunt being deployed to seal the arterial puncture site, according to an embodiment.
Figure 21:
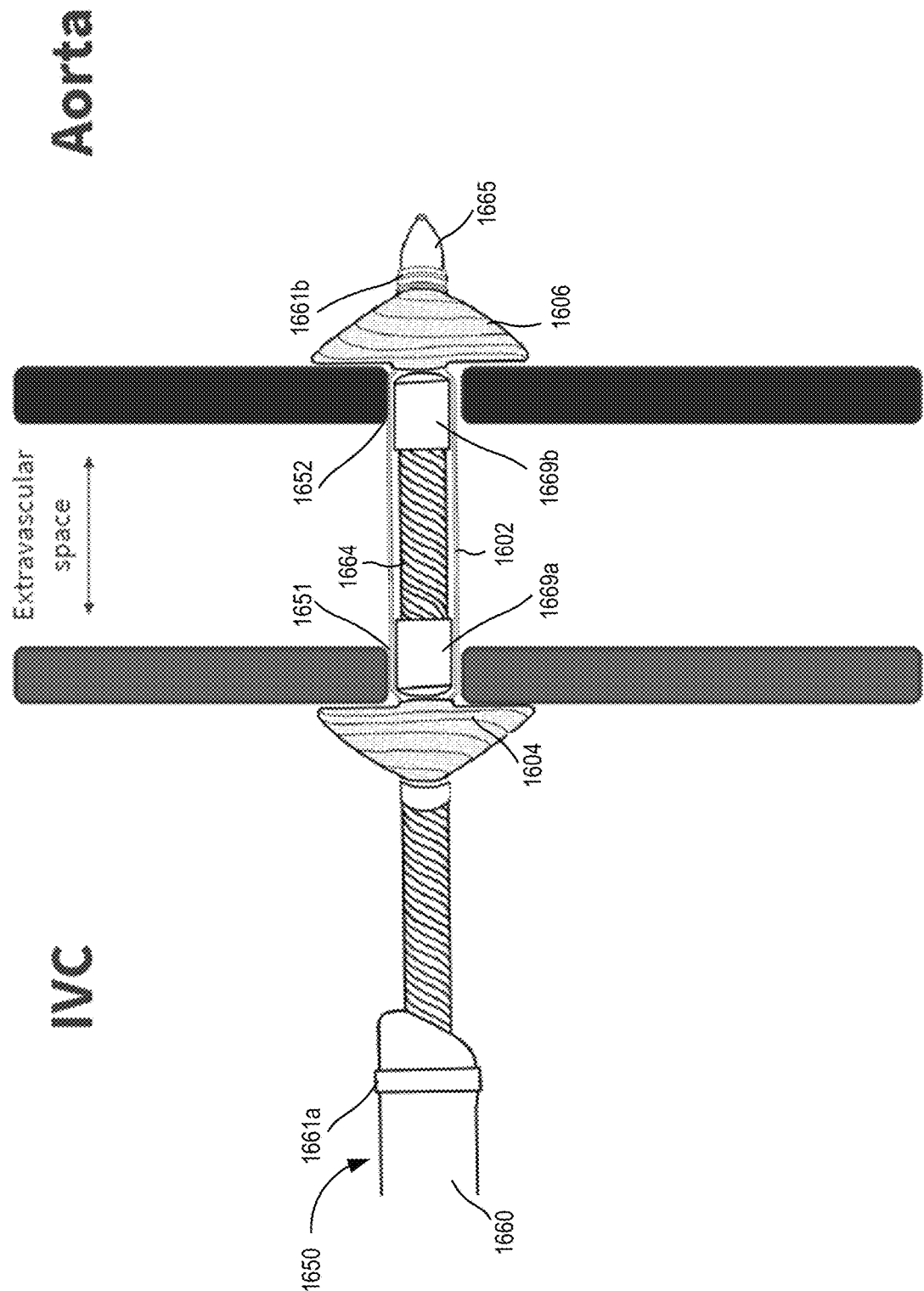
FIG. 21 is a diagram of the proximal end of the shunt being deployed to seal the venous puncture site, according to an embodiment.
Figure 22:
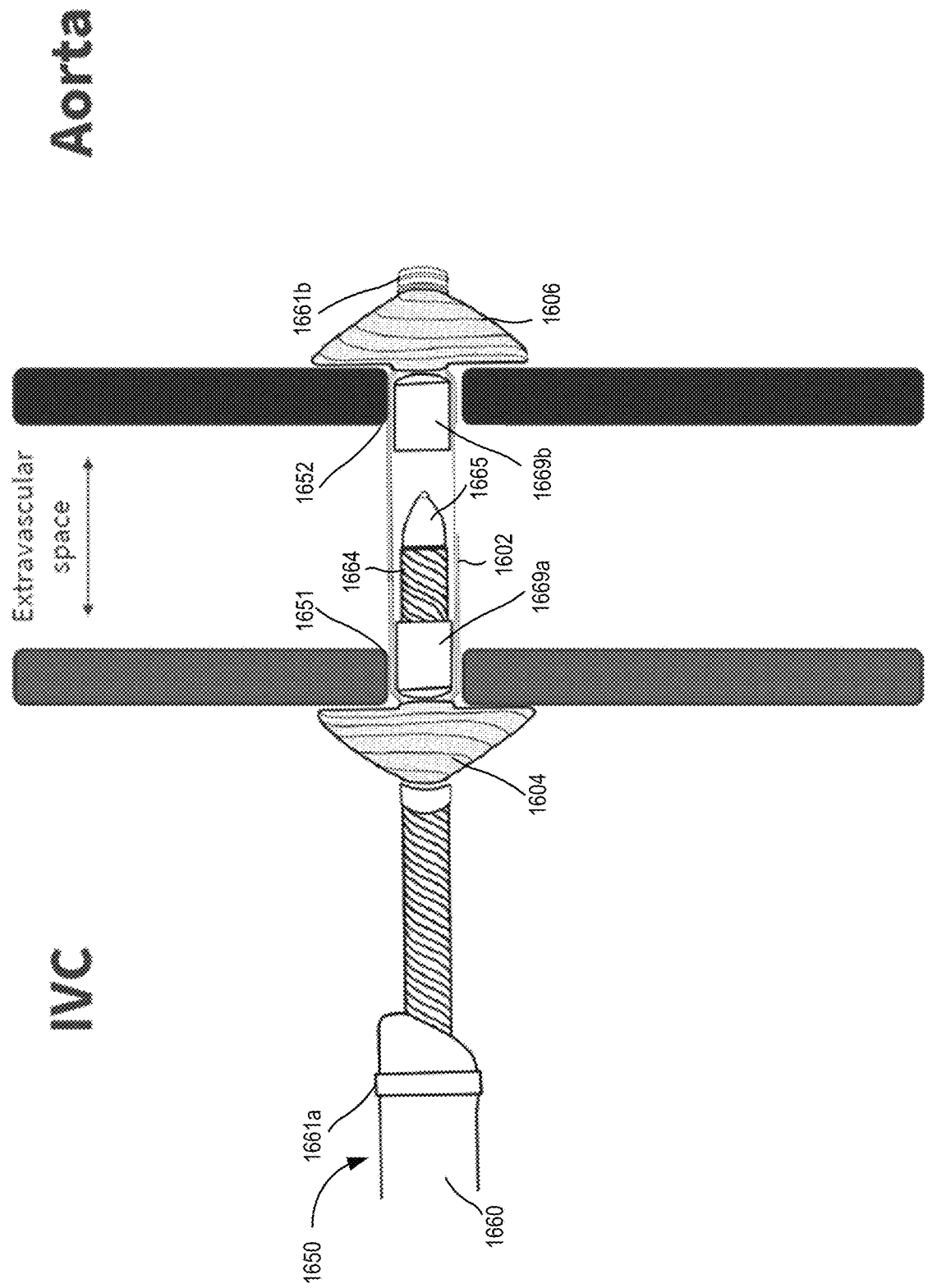
FIGS. 22-24 are diagrams of the dilator body being retracted such that the shunt is disposed between the aorta and the vena cava in the deployed configuration, according to an embodiment.
Figure 23:
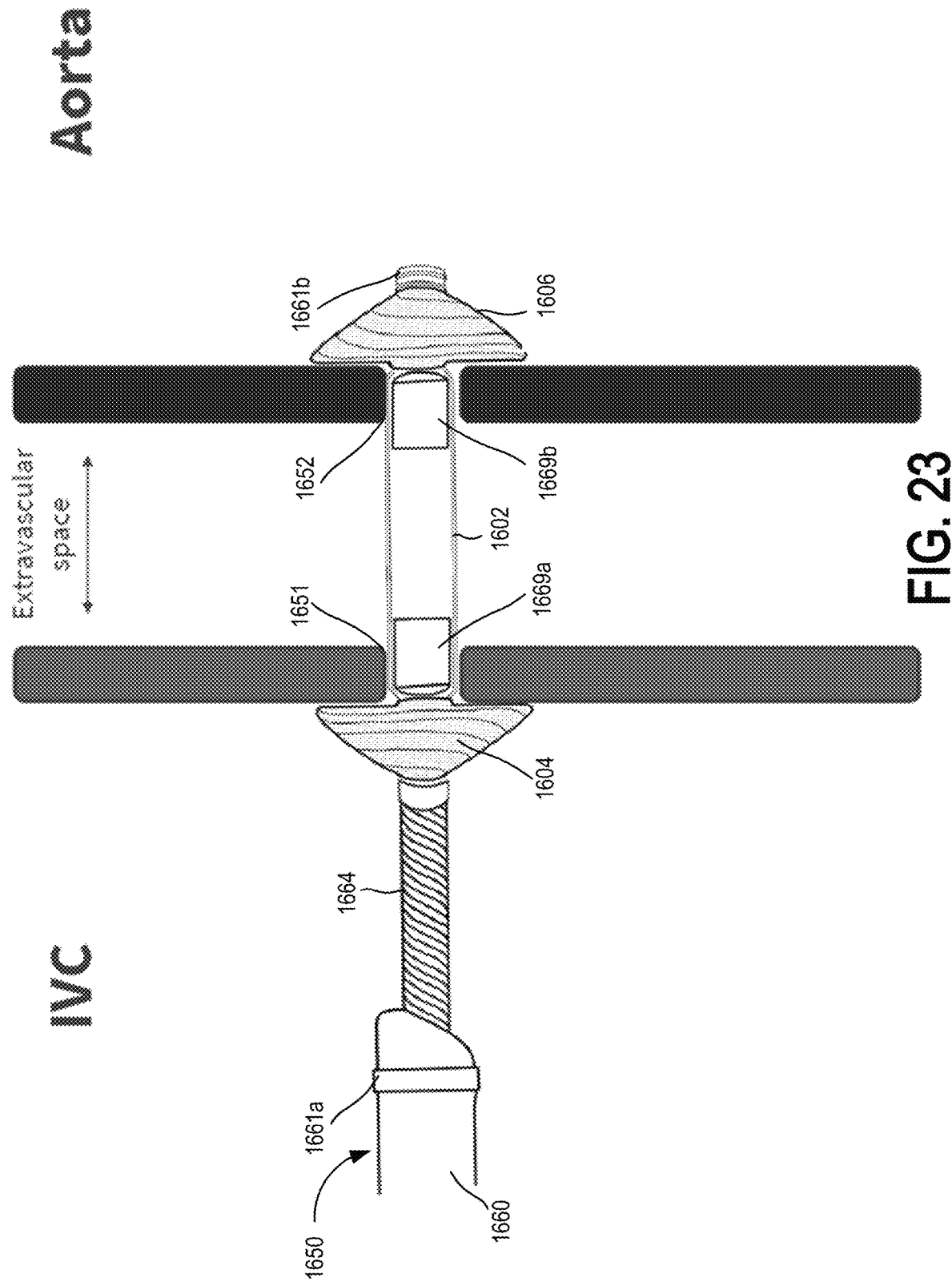
Figure 24:
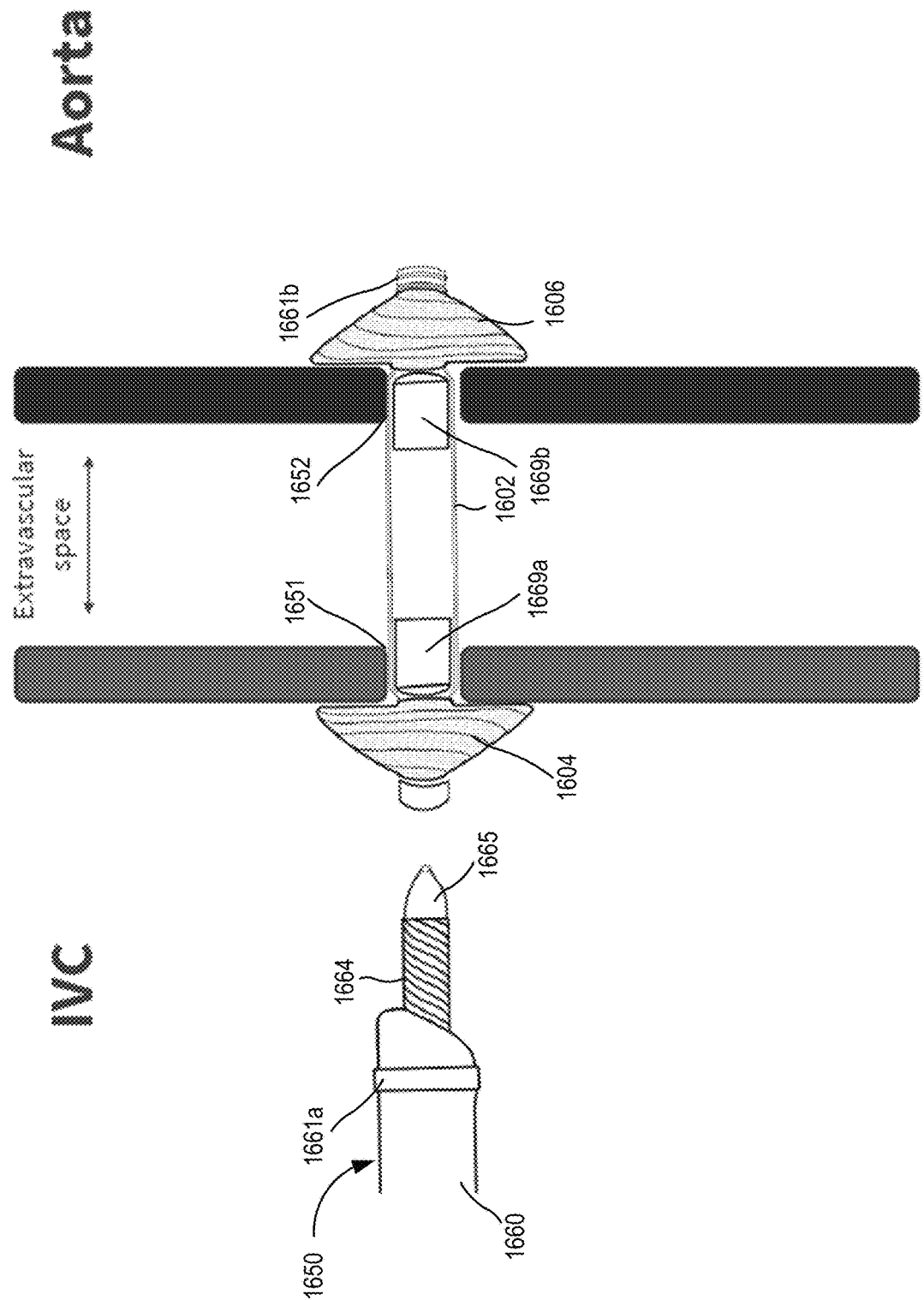
Figure 25:
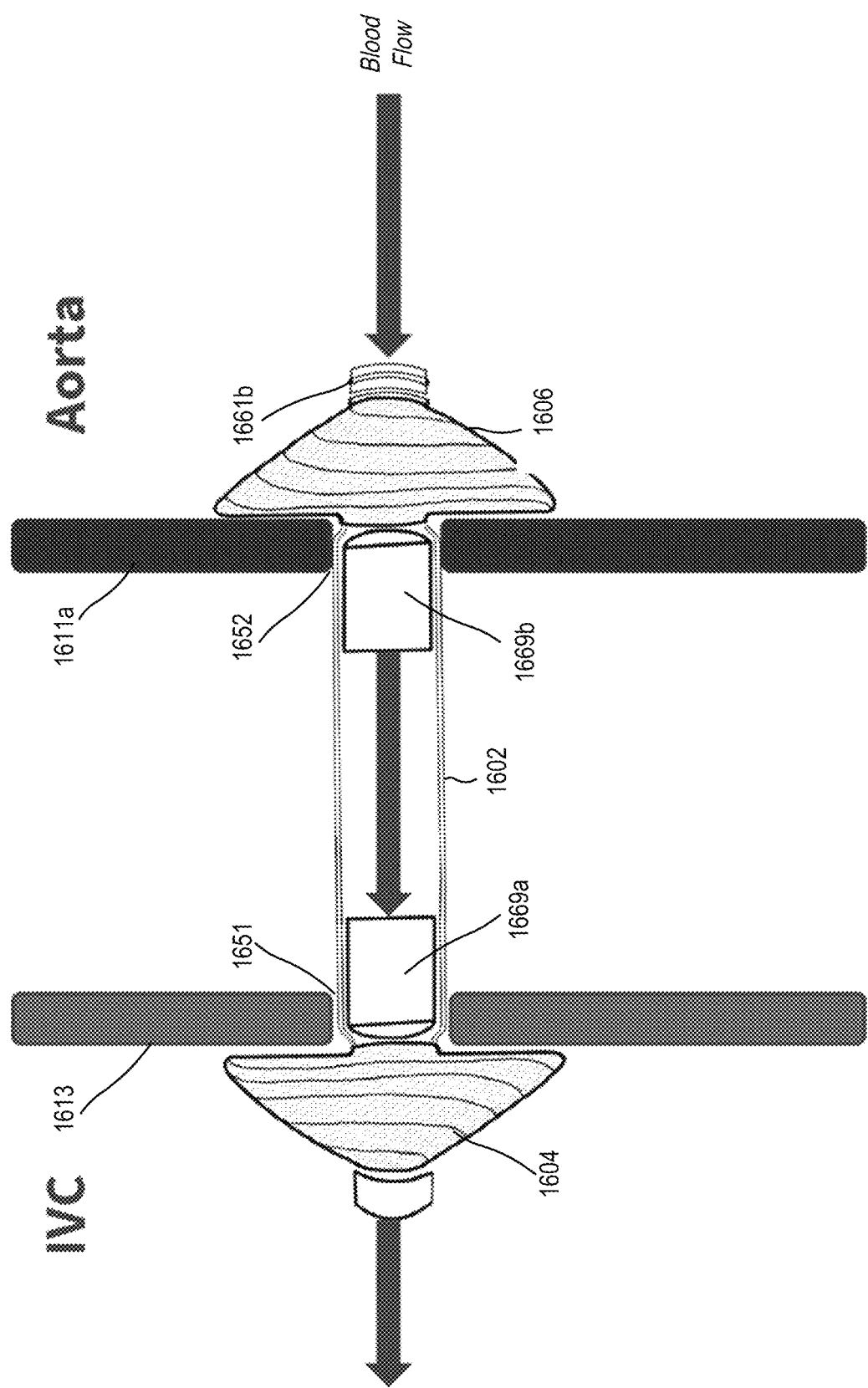
FIG. 25 is a diagram illustrating blood flow through the shunt deployed between the aorta and the vena cava, according to an embodiment.

As shown in FIGS. 20-21, once the shunt is in position, the dilator 1664 may be retracted (e.g., moved in a proximal direction) such that the arterial sealing structure 1606 transitions from the delivery configuration to the deployed configuration and then subsequently the venous sealing structure 1604 transitions to the deployed configuration. After the shunt is deployed, the dilator 1664 may be further retracted proximally through the central portion 1602 of the shunt, as shown in FIGS. 22-24. FIG. 25 illustrates blood flow through the shunt deployed between the aorta and the vena cava.

Figure 26:
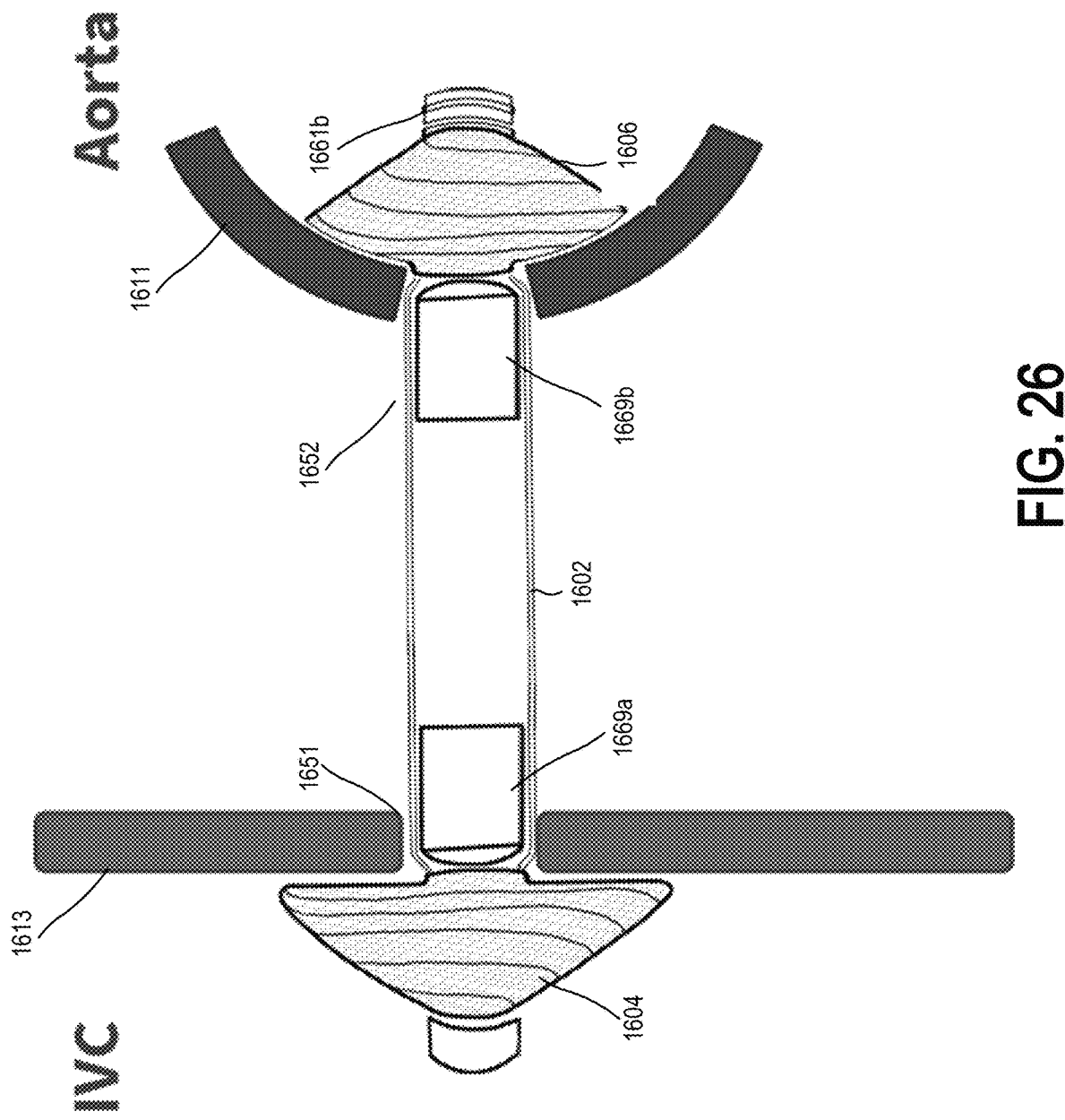
FIG. 26 is a diagram illustrating the arterial sealing structure of the deployed shunt conforming to a curvature of the aorta, according to an embodiment.
Figure 27:
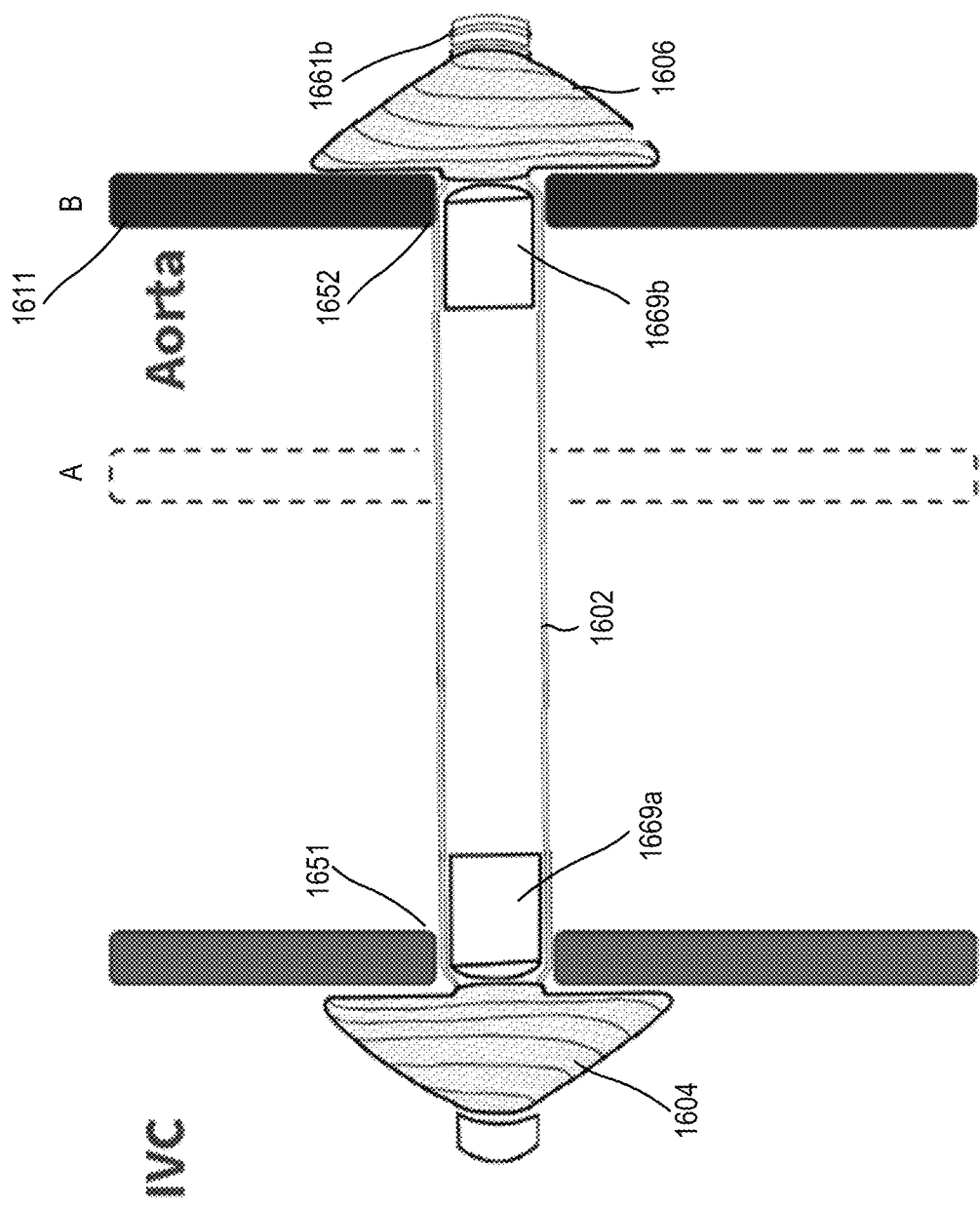
FIG. 27 is a diagram illustrating flexibility of the body of the shunt such that a fluid tight seal around the arterial puncture site is maintained, according to an embodiment.
Figure 28:
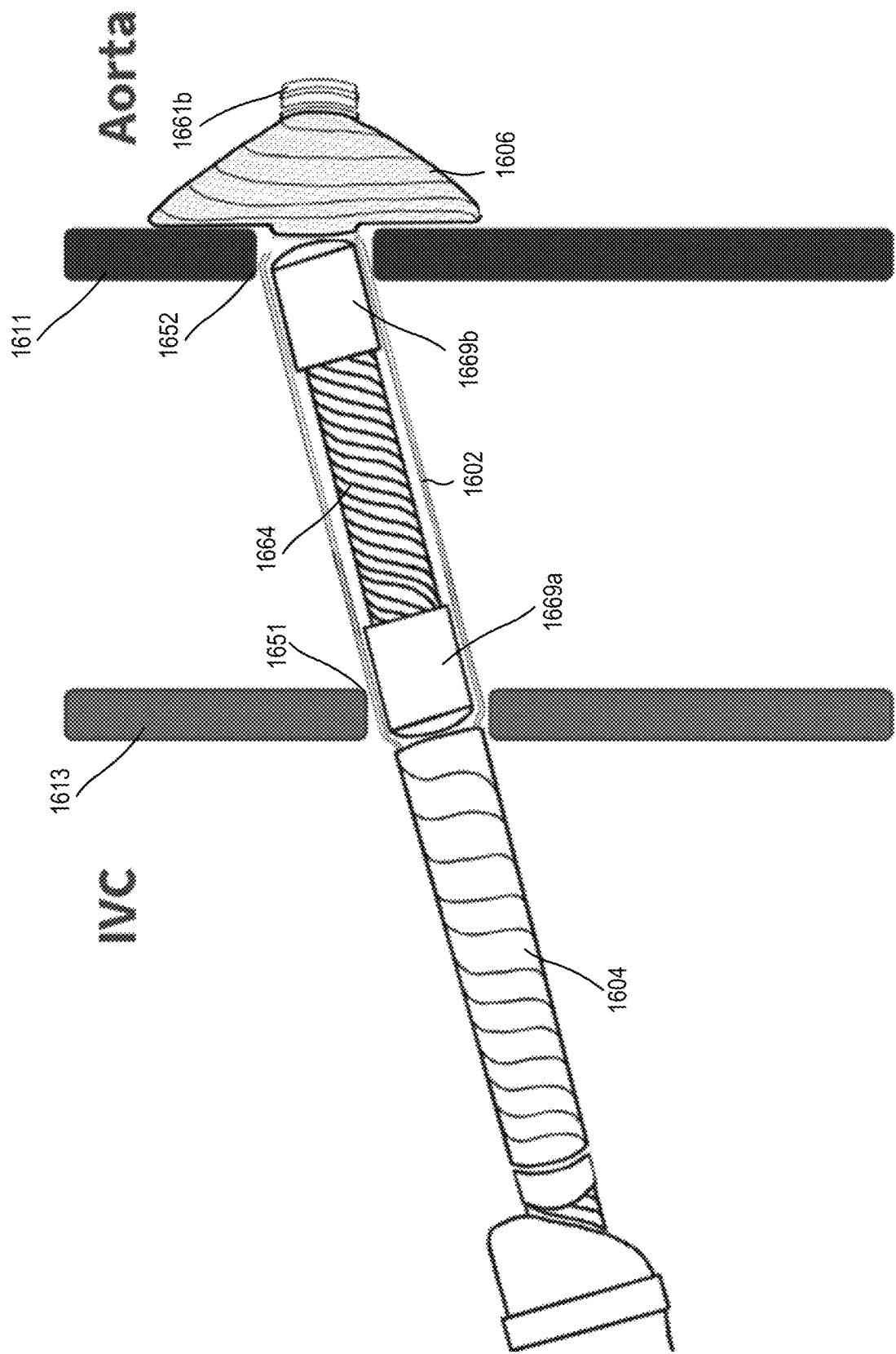
FIG. 28 is a diagram illustrating the venous sealing structure and the arterial sealing structure of the shunt pivoting relative to a central portion of the shunt to maintain the fluid tight seal, according to an embodiment.

FIG. 26 is a diagram illustrating the arterial sealing structure of the deployed shunt conforming to a curvature of the aorta. FIG. 27 is a diagram illustrating flexibility of the central portion 1602 of the shunt (e.g., to expand, extend, lengthen) such that a fluid tight seal around the arterial puncture site 1652 is maintained as the aortic aneurysm shrinks, and the aortic wall moves from position A to position B. FIG. 28 is a diagram illustrating the arterial sealing structure 1606 of the shunt pivoting relative to the central portion 1602 of the shunt to maintain the fluid tight seal at the arterial puncture site 1652.

Figure 29:
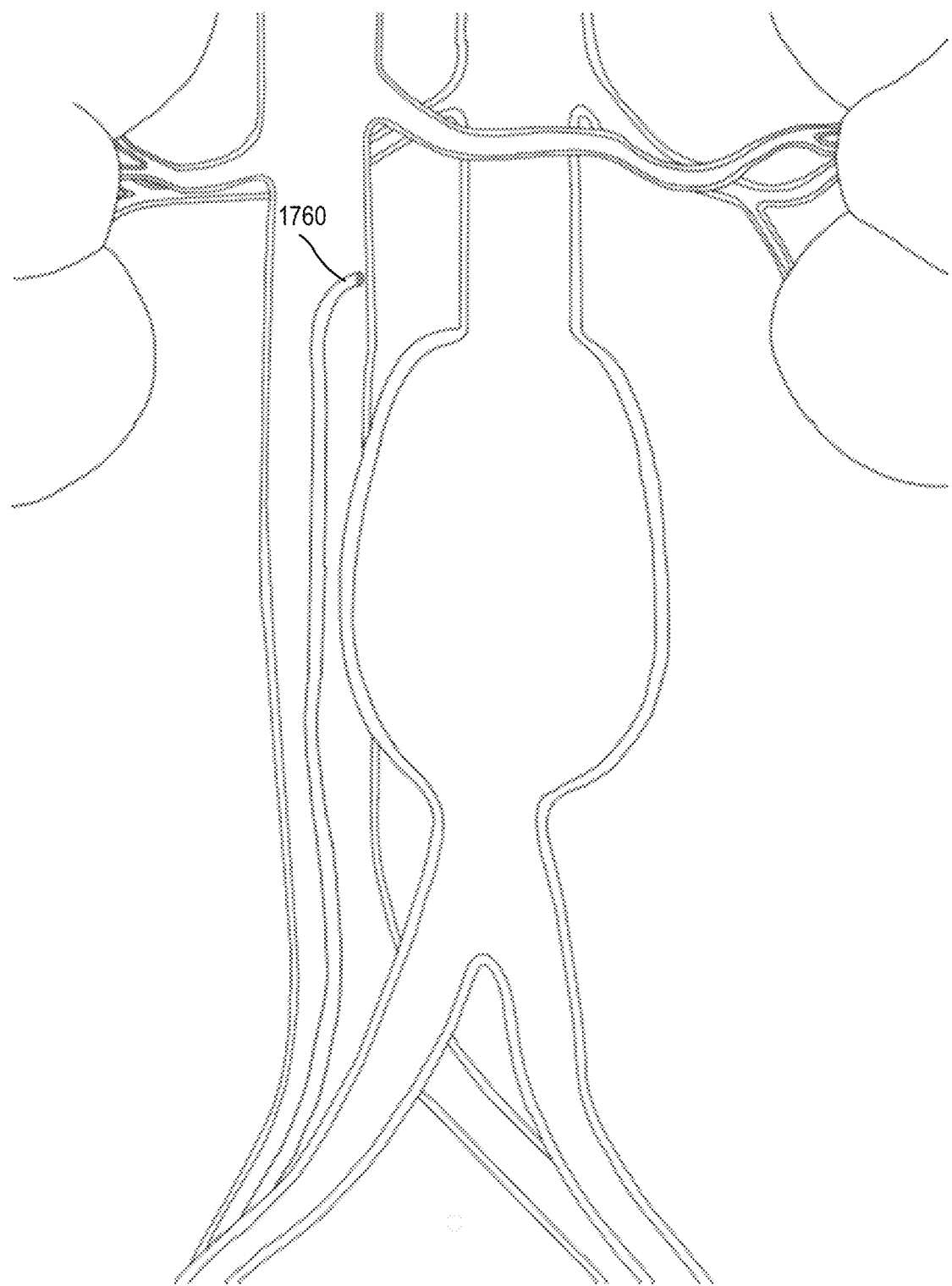
FIGS. 29-38 are diagrams illustrating implantation of a shunt using a snare wire, according to an embodiment.
Figure 30:
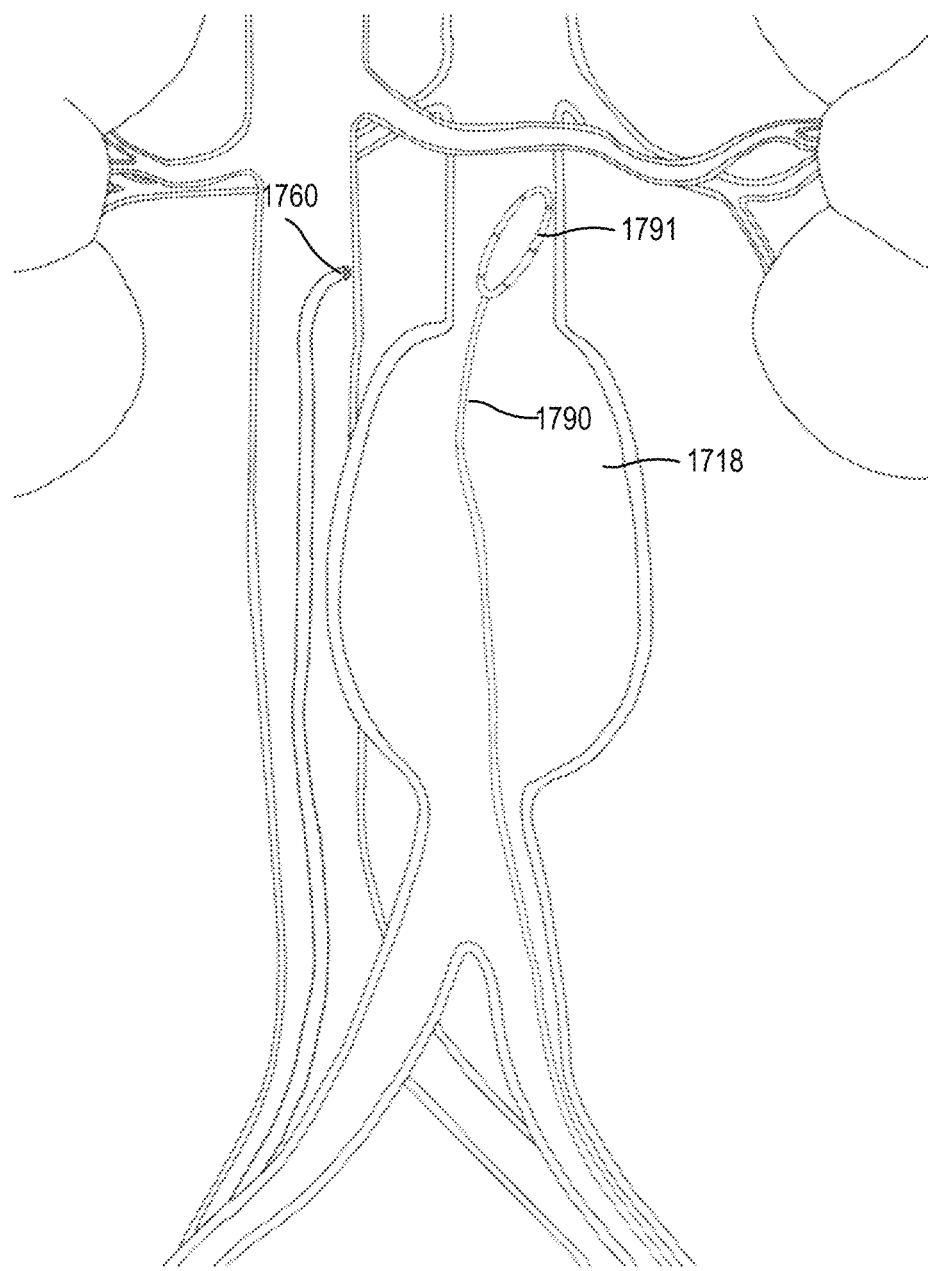

FIGS. 29-38 are diagrams illustrating implantation of a shunt using by puncturing the vena cava and the aorta using a guidewire of the delivery system and a snare wire, according to an embodiment. In some embodiments, a steerable catheter 1760 is inserted through the vena cava, as shown in FIG. 29. In some cases, the catheter 1760 is advanced to a puncture site at the vena cava using a similar method as described herein with reference to FIGS. 15-28. In some embodiments, a snare wire 1790 may be advanced through the artery, through the aneurysm sac 1718, and to a location proximate to a targeted puncture site of the aorta, as shown in FIG. 30. In some embodiments, the targeted puncture site of the artery is disposed upstream (e.g., with respect to blood flow) of the aneurysmal sac 1718.

In some embodiments, the snare wire 2602 includes a proximal end and a distal end. In some embodiments, the snare wire has a length of from about 10 cm to about 100 cm, inclusive of all ranges and subranges therebetween. In some embodiments, the snare wire has a thickness of from about 0.1 mm to about 3 mm, inclusive of all ranges and subranges therebetween. In some embodiments, the snare wire 1790 includes a snare wire loop 1791 disposed at the distal end of the snare wire. In some embodiments, the snare wire loop 1791 is configured to be tightened and/or loosened. In some embodiments, tightening the snare wire loop 1791 decreases a diameter of the snare wire loop 1791.

Figure 31:
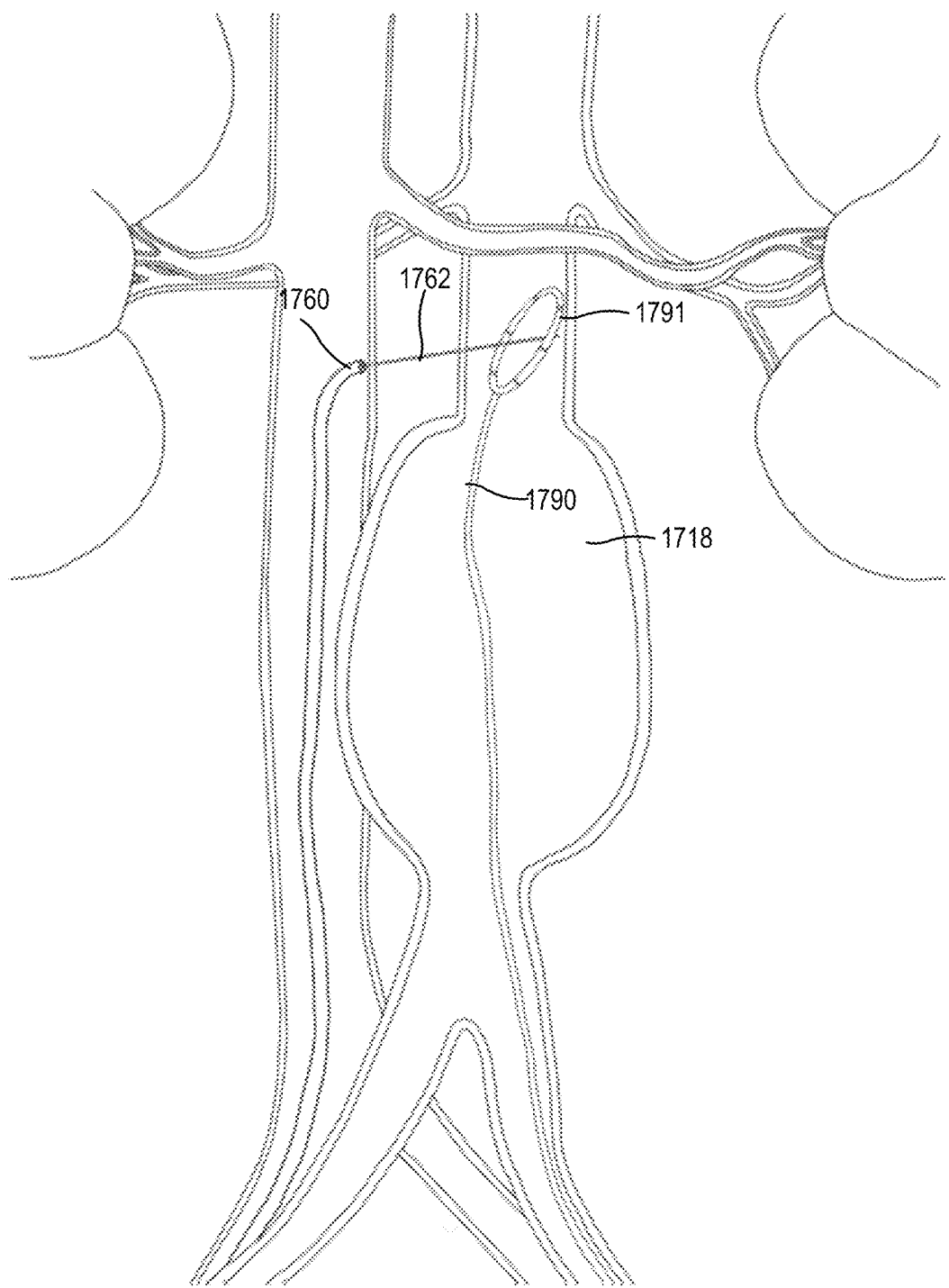
Figure 32:
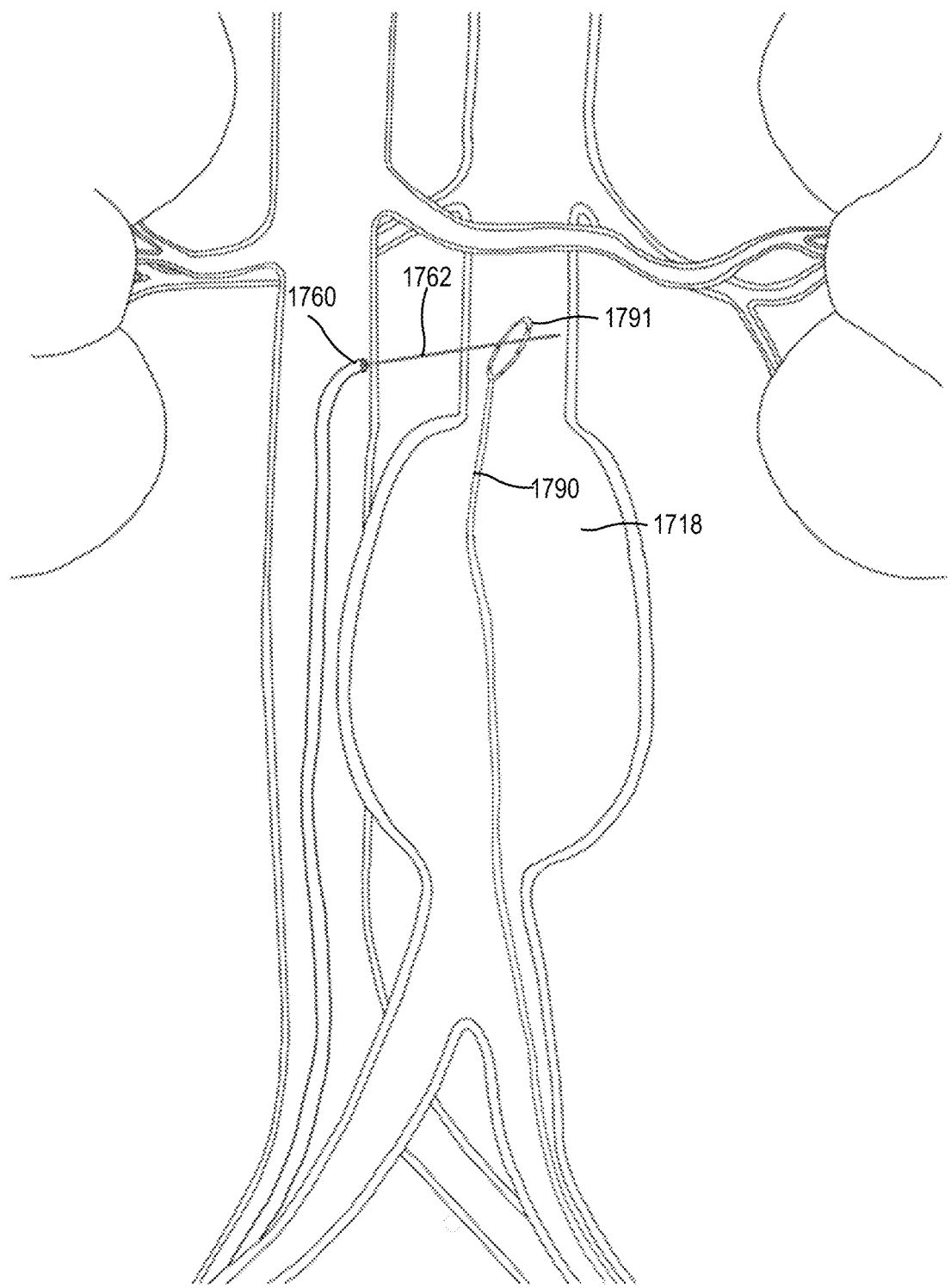
Figure 33:
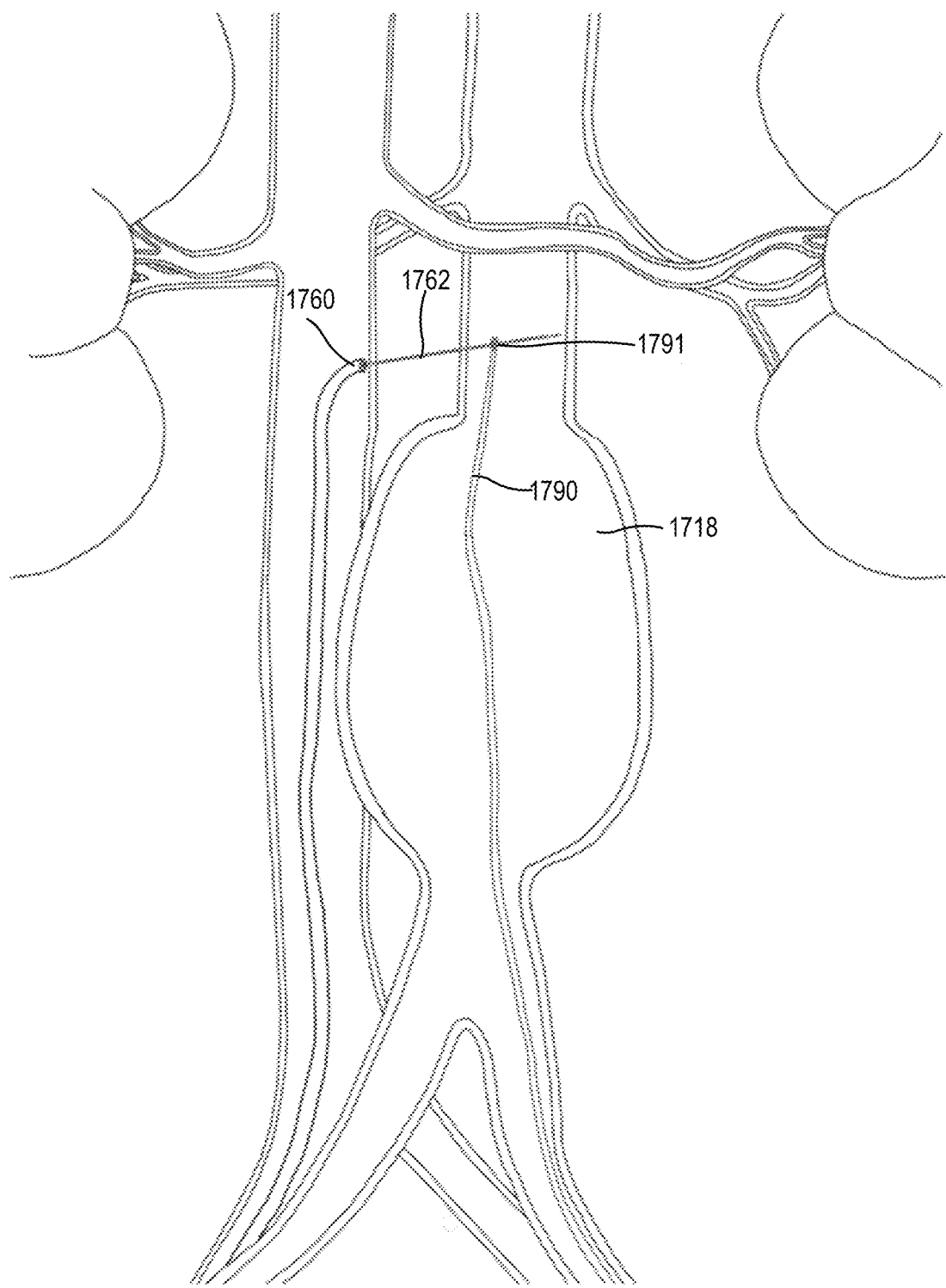
Figure 34:
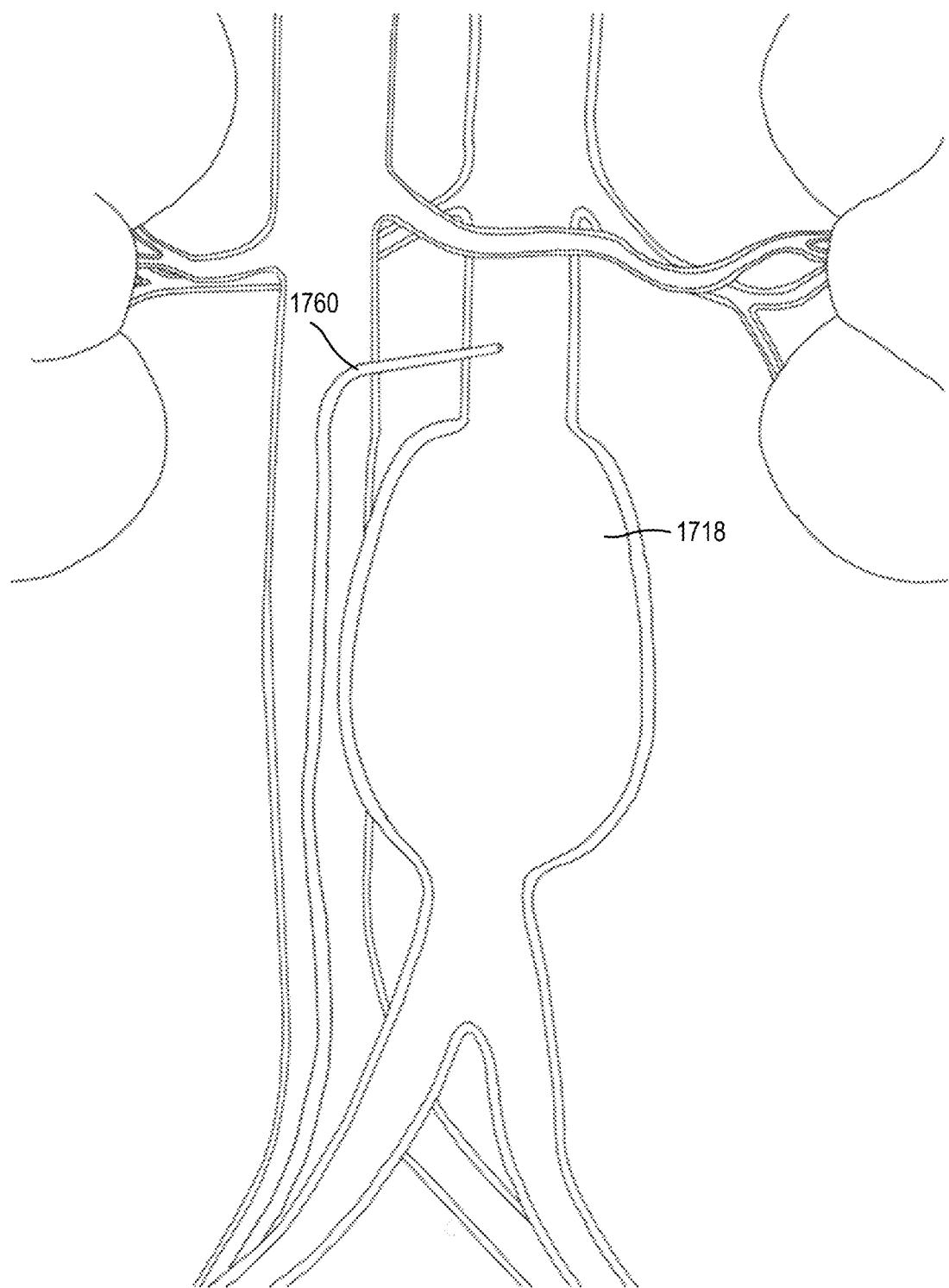
Figure 35:
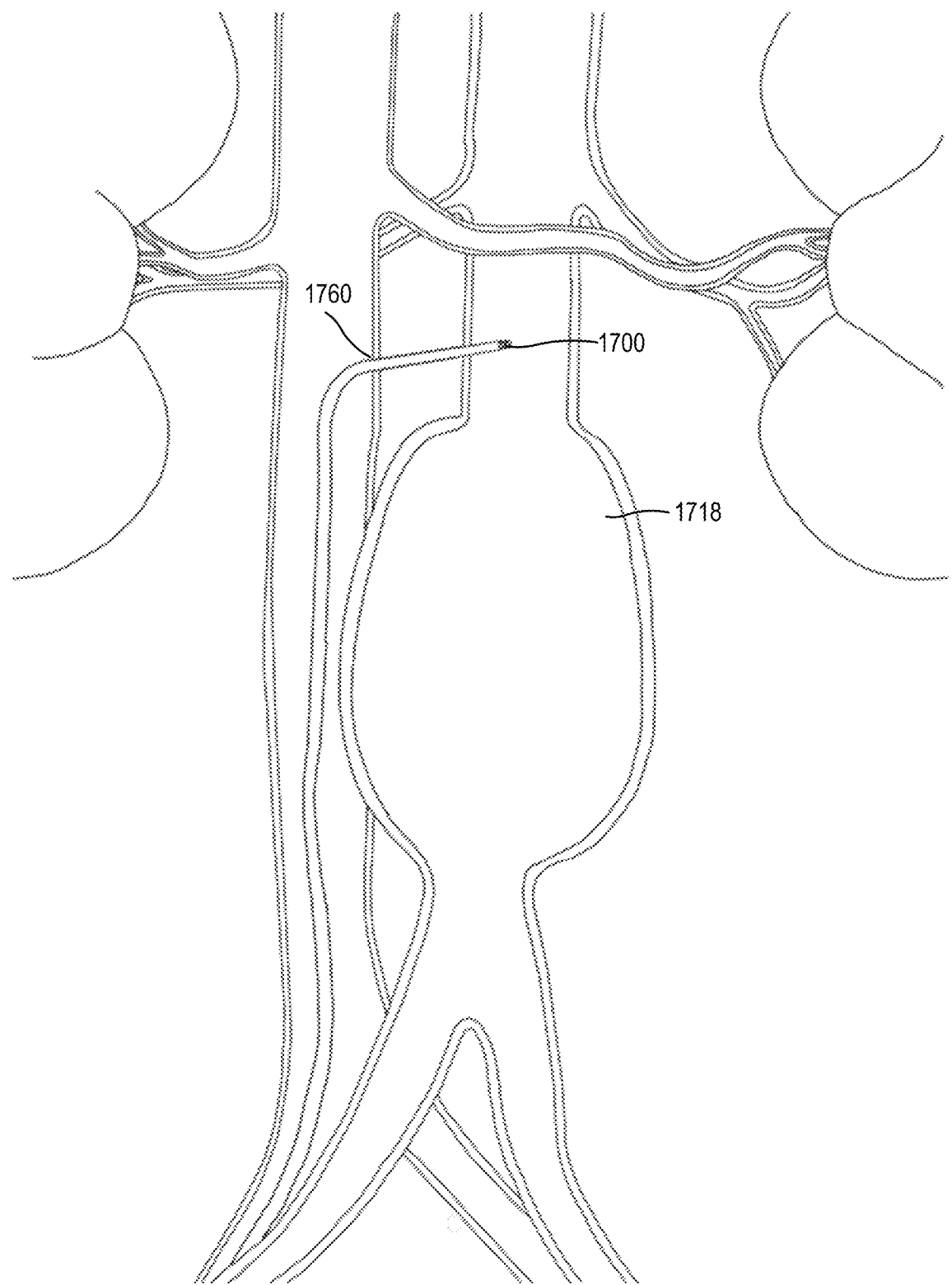
Figure 36:
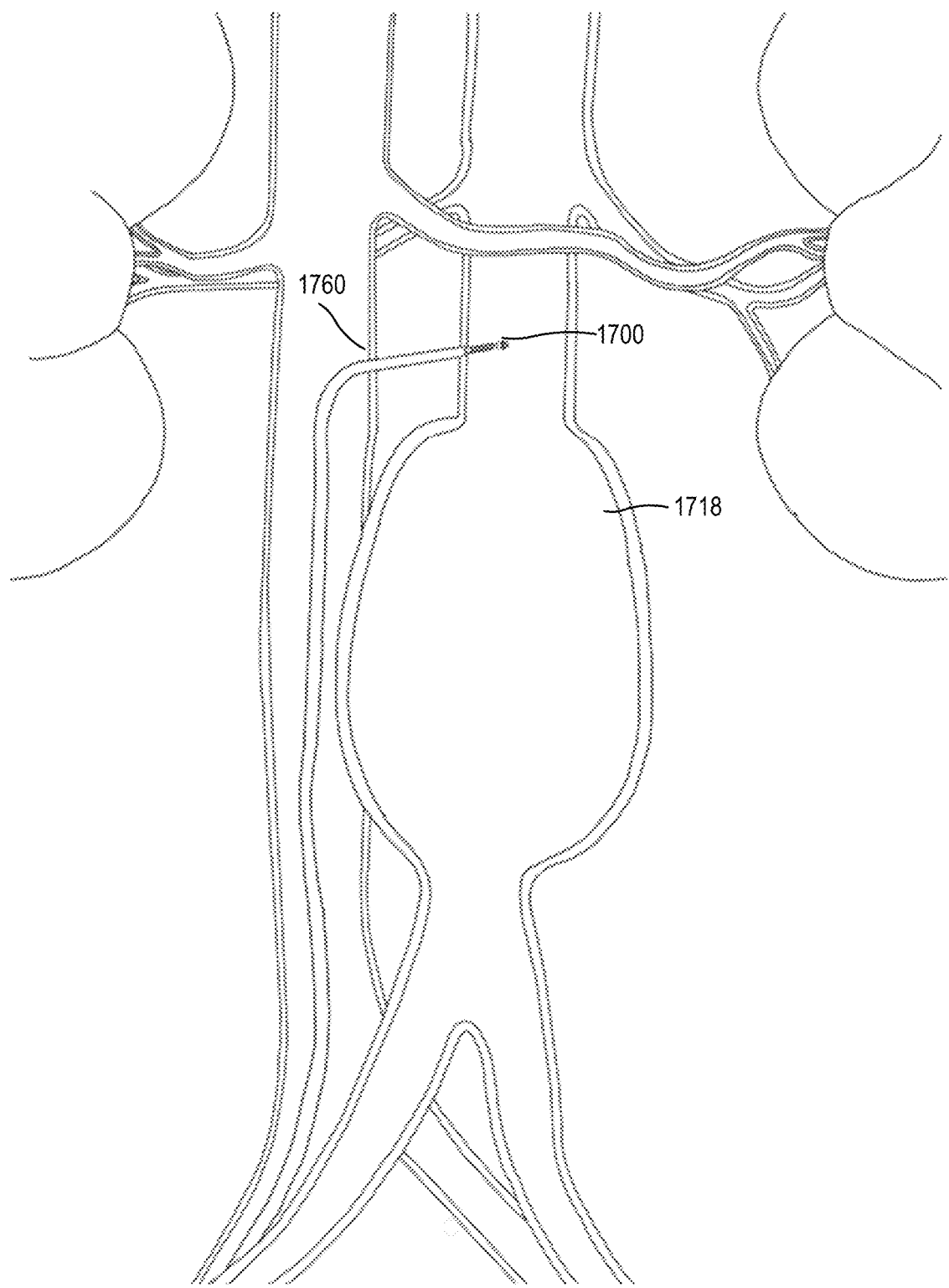
Figure 37:
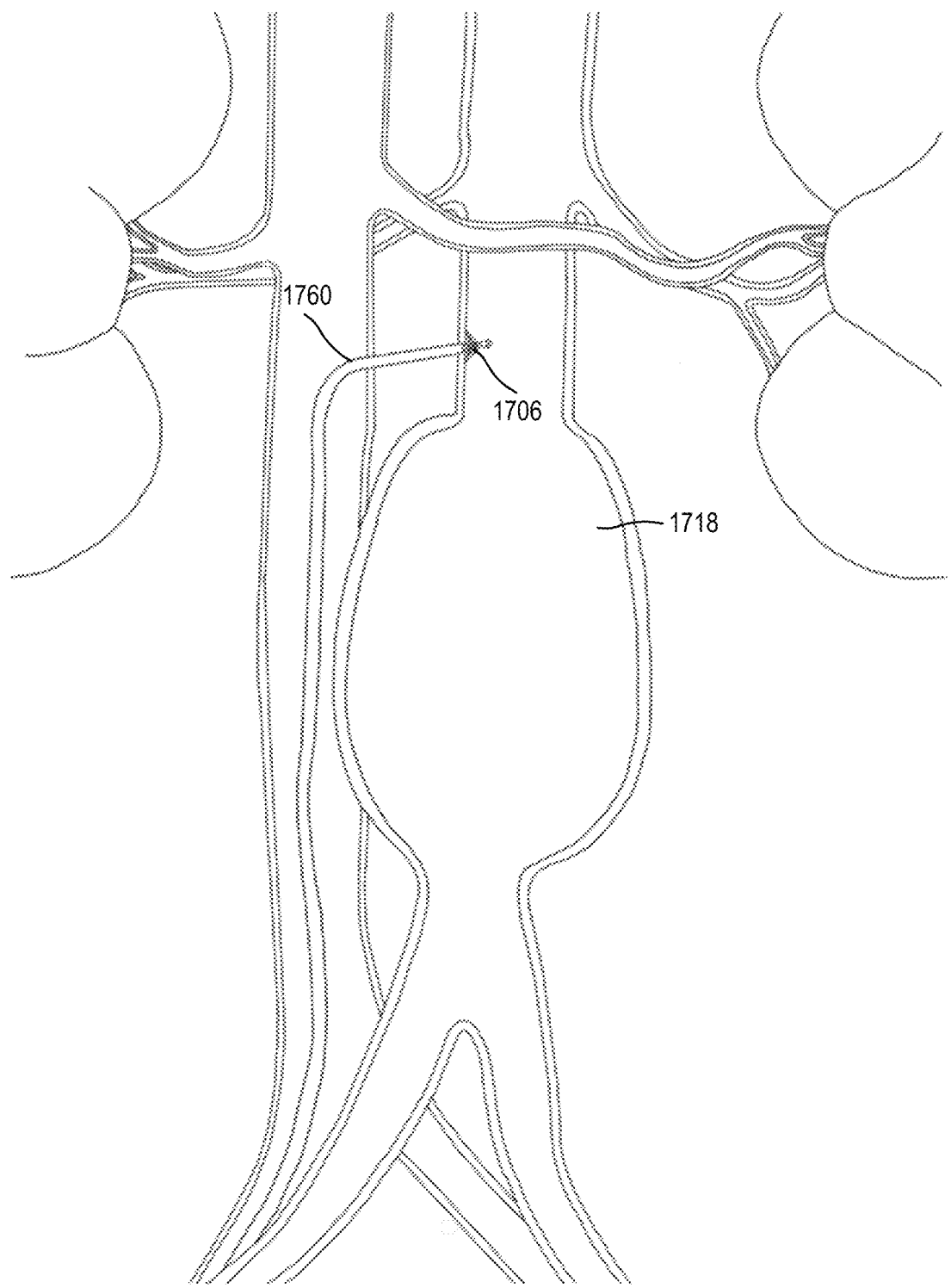
Figure 38:
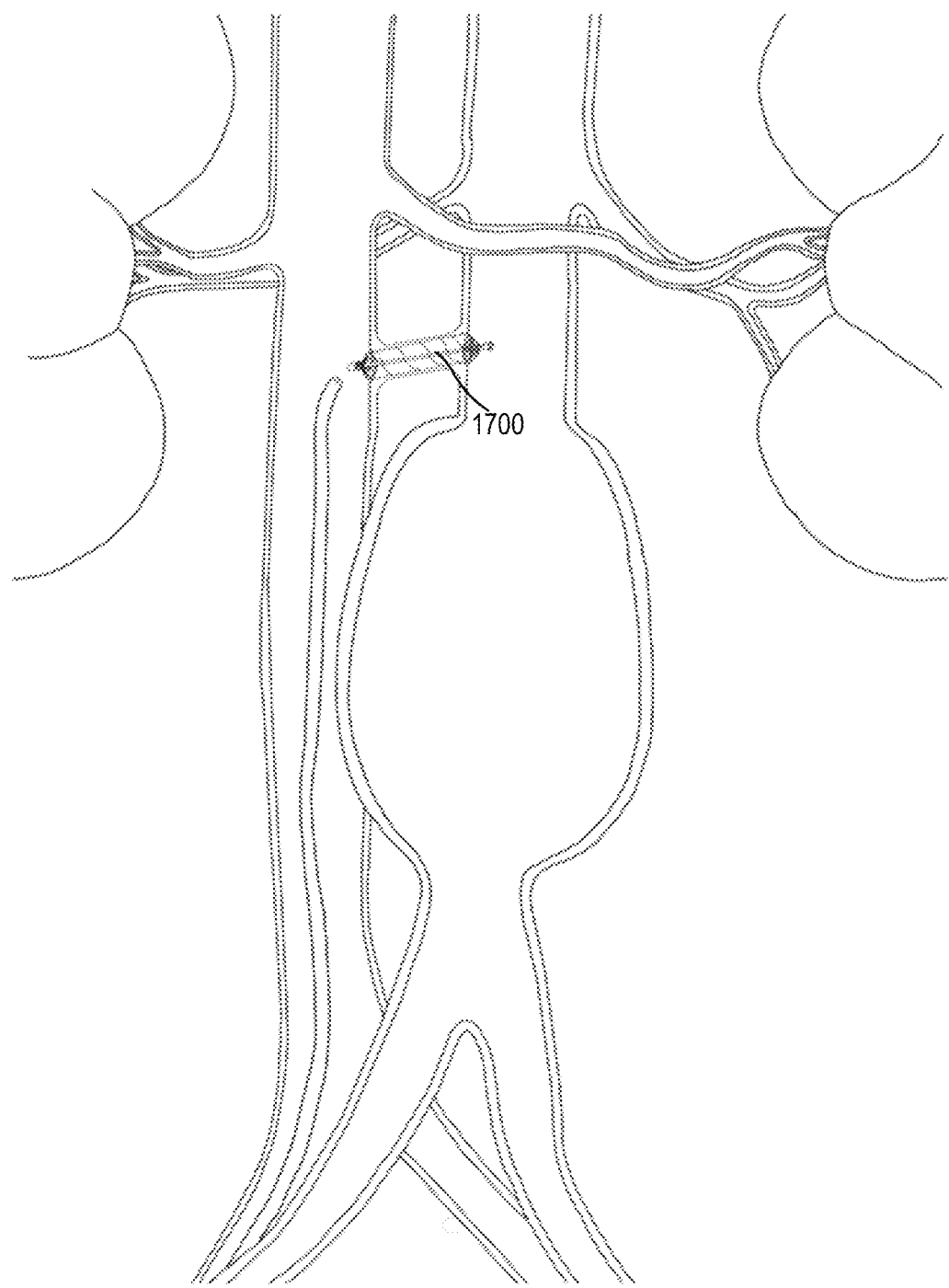
Figure 39:
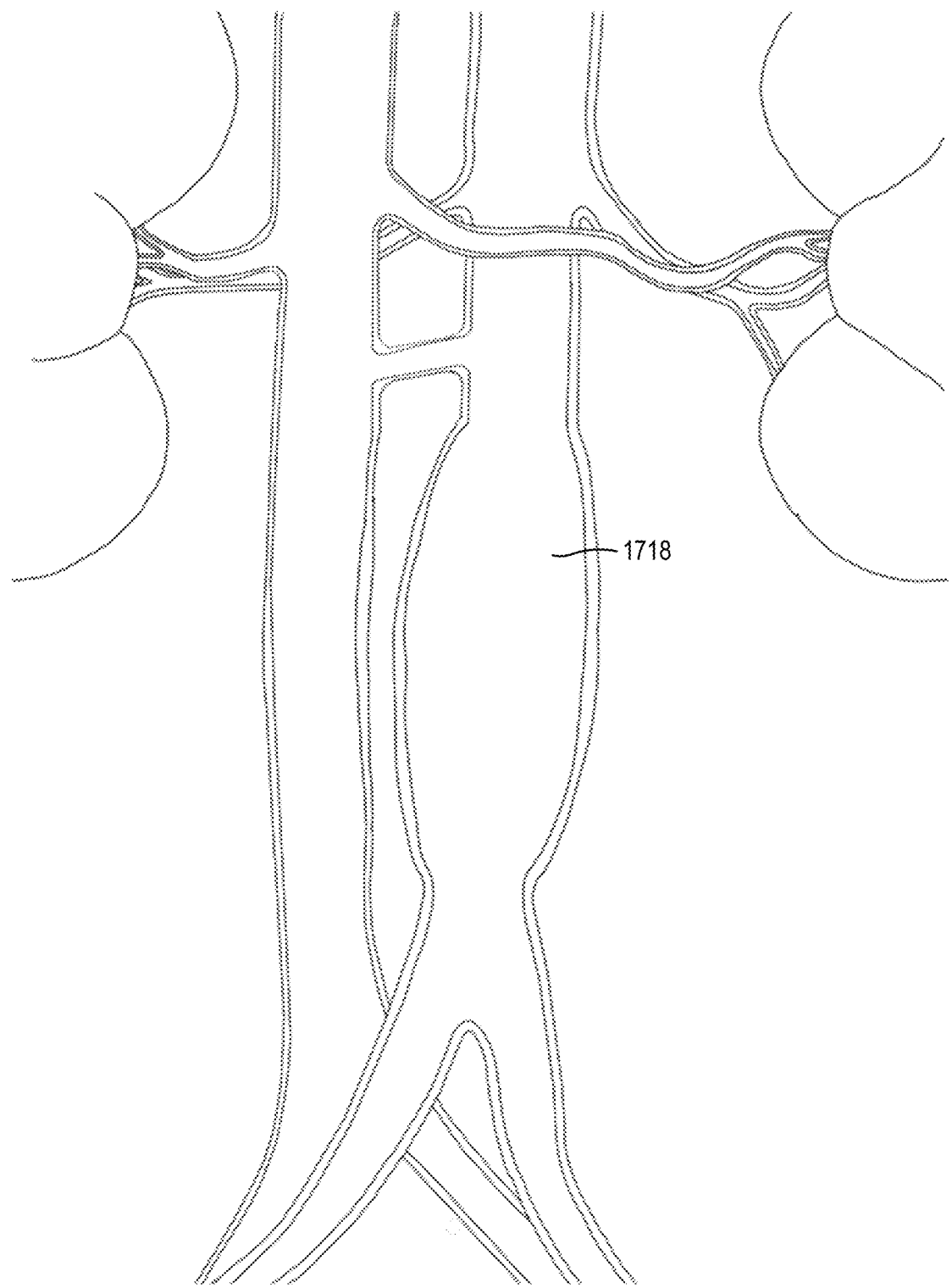
FIG. 39 is a diagram showing a decrease in size of the aneurysm sac and tissue ingrowth into the shunt after implantation of the shunt.

In some embodiments, a guidewire 1762 is then advanced from the catheter 1760 to puncture through the vena cava and access the aorta via the puncture site at the aorta, as shown in FIG. 31. In some embodiments, the guidewire 1762 may be advanced until it is located within the snare wire loop 1791. In some embodiments, radiopaque markers on the guidewire 1762 and/or the snare wire 1790 (e.g., snare wire loop 1791) may be used to determine the location of the guidewire relative to the snare wire loop. In some embodiments, the snare wire 1790 is tightened, so as to shorten the snare wire loop 1791, as shown in FIG. 32, and to secure the snare wire loop 1791 about the guidewire 1762, thereby securing the snare wire to the guidewire, as shown in FIG. 33. In some embodiments, the snare wire is then pulled, so as to advance the catheter 1750 through the aorta puncture site, as shown in FIG. 34. In some embodiments, the guidewire 1762 is then cut and removed. In some embodiments, a shunt 1700 is then advanced through the catheter 1750 to the aorta, as shown in FIGS. 35-36. In some embodiments, a distal sealing structure 1706 is then deployed, as shown in FIG. 37, so as to seal the arterial puncture site. In some embodiments, the distal sealing structure is deployed similar to as described herein for the distal sealing structure 1706, using a sliding sheath. Accordingly, withdrawing the catheter and a corresponding sliding sheath enables a proximal sliding structure for the shunt 1700 to be deployed, thereby providing a sealed fluid (e.g., blow) flow path between the aorta and vena cava, as shown in FIG. 38. FIG. 39 illustrates tissue ingrowth into the shunt to form a permanent (or semi-permanent) flow path between the aorta and the vena cava. Additionally, FIG. 39 depicts a reduction in the size of the aneurysm sac due to implantation of the shunt to alleviate pressure in the aneurysm sac.

As described herein, in some aspects, systems and methods disclose treating an aortic aneurysm by implanting a bypass graft so as to divert some or all of the fluid (e.g., blood) flow around an aneurysmal sac, thereby alleviating the pressure against the aneurysmal sac, and reducing the risk of an aneurysm rupture. FIGS. 40A-40E are diagrams of implantation of a bypass graft 1880 connecting a portion of the aorta 1811*a* above the aneurysm sac 1818 to a portion of the aorta 1811*b* below the aneurysm sac 1818 to treat the aneurysm, according to an embodiment. In some embodiments, the bypass graft 1880 accesses the aorta 1811 through an arterial puncture site. In some embodiments, the bypass graft 1880 passes within a vena cava 1813, and then rejoins the aorta 1811 downstream of an aneurysm sac 1818. In some embodiments, the system includes one or more (e.g., 1, 2, 3, 4, 5, 6, 7, 8, 9, or 10) bypass grafts 1880. In some embodiments, the bypass graft 1880 includes a proximal end, a distal end, and a bypass graft lumen traversing the length of the bypass graft 1880 from the proximal end to the distal end. In some embodiments, the bypass graft 1880 has a length of from about 20 mm to about 20 cm, inclusive of all ranges and subranges therebetween. In some embodiments, the bypass graft 1880 has a bypass graft wall forming an inner diameter of the bypass graft and an outer diameter of the bypass graft. In some embodiments, the inner diameter of the bypass graft 1880 is in a range of about 5 mm to about 30 mm, inclusive of all ranges and subranges therebetween. In some embodiments, the outer diameter of the bypass graft 1880 is in a range of about 5 mm to about 30 mm, inclusive of all ranges and subranges therebetween.

The bypass graft 1880 may be manufactured from any biologically acceptable material that possesses the ability to be shaped into a tubular structure having the required compliance. In some embodiments, the bypass graft 1880 may include a material including expanded polytetrafluoroethylene (e-PTFE); woven, knitted, or velour design polyethylene terephthalate (PET); or Dacron. In some embodiments, the bypass graft 1880 may include polymeric fibers such as, for example, polyurethanes, polyethylene terephthalate, polypropylene, and polytetrafluoroethylene. In some embodiments, the polymeric fibers may include elastomeric polymers, e.g. polyurethane elastomers or composite fibers that act in an elastic fashion. In some embodiments, polymeric fibers may be "shrinking" polymers (e.g., pressure-sensitive polymers) where the shrinkage may be controlled. In some embodiments, the bypass graft 1880 may include wires of one or more metals such as, for example, stainless steel and cobalt-chromium alloys. In some embodiments, the bypass graft 1880 may include wires made of shape memory alloys such as Nitinol. In some embodiments, the bypass graft 1880 may be at least partially coated with a polymer for improved biocompatibility. In some embodiments, the coating may be the same or similar to the cover/coating used on the shunt 100, as described with respect to FIG. 1.

Figure 40A:
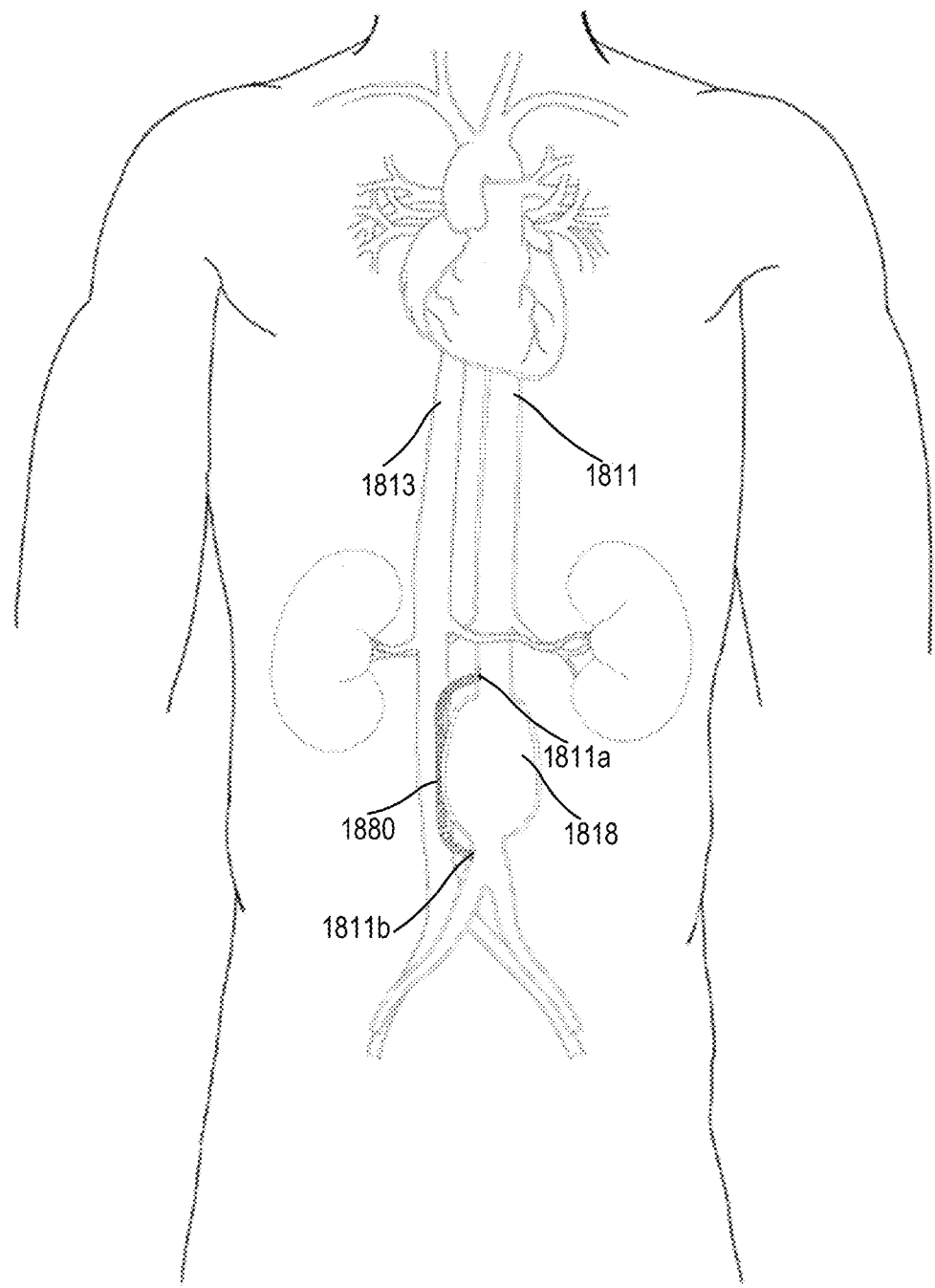
FIGS. 40A-40E are diagrams of implantation of a bypass graft connecting a portion of the aorta above the aneurysm sac to a portion of the aorta below the aneurysm sac to treat or alleviate the aneurysm, according to an embodiment.
Figure 40B:
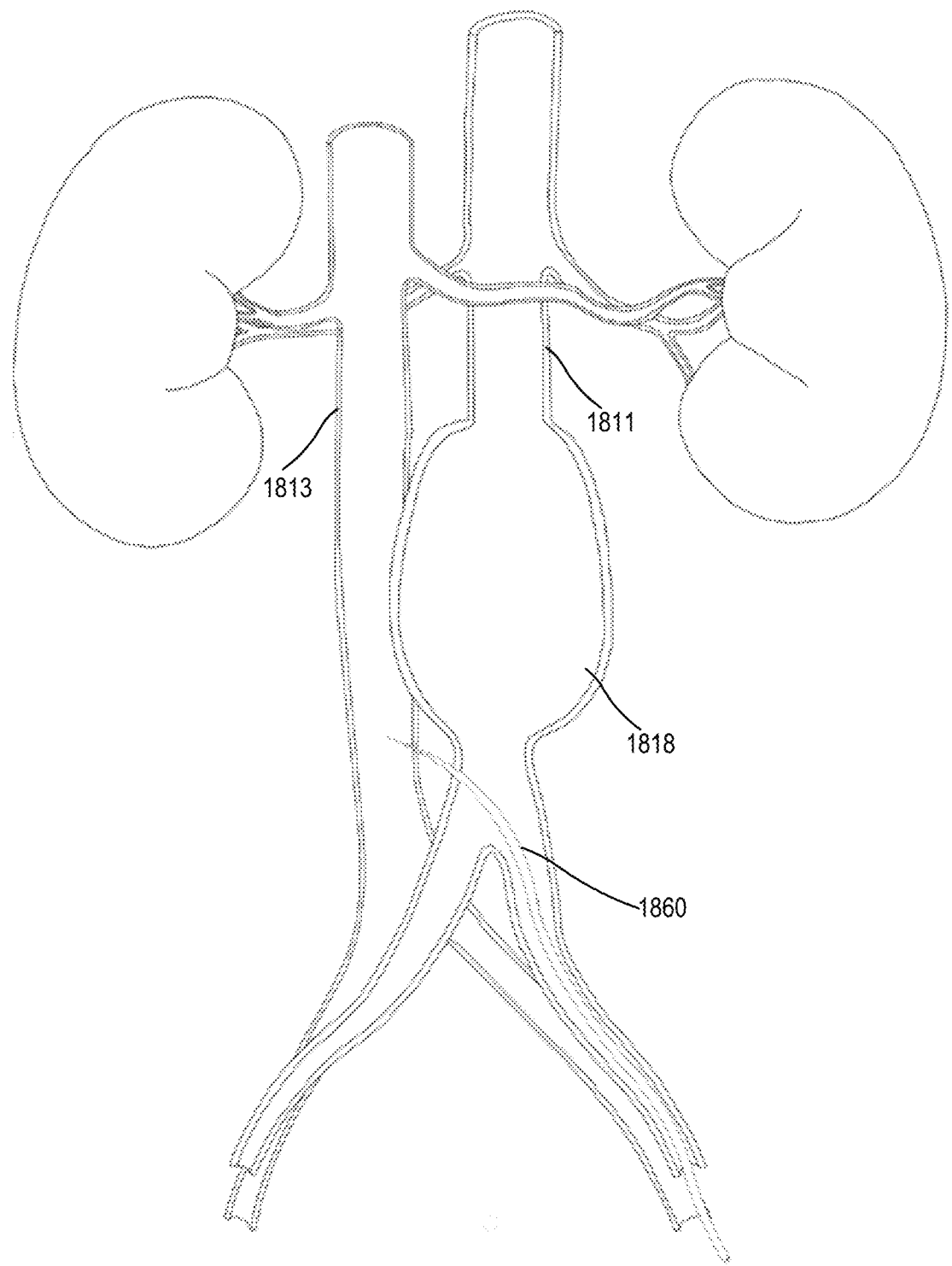
Figure 40C:
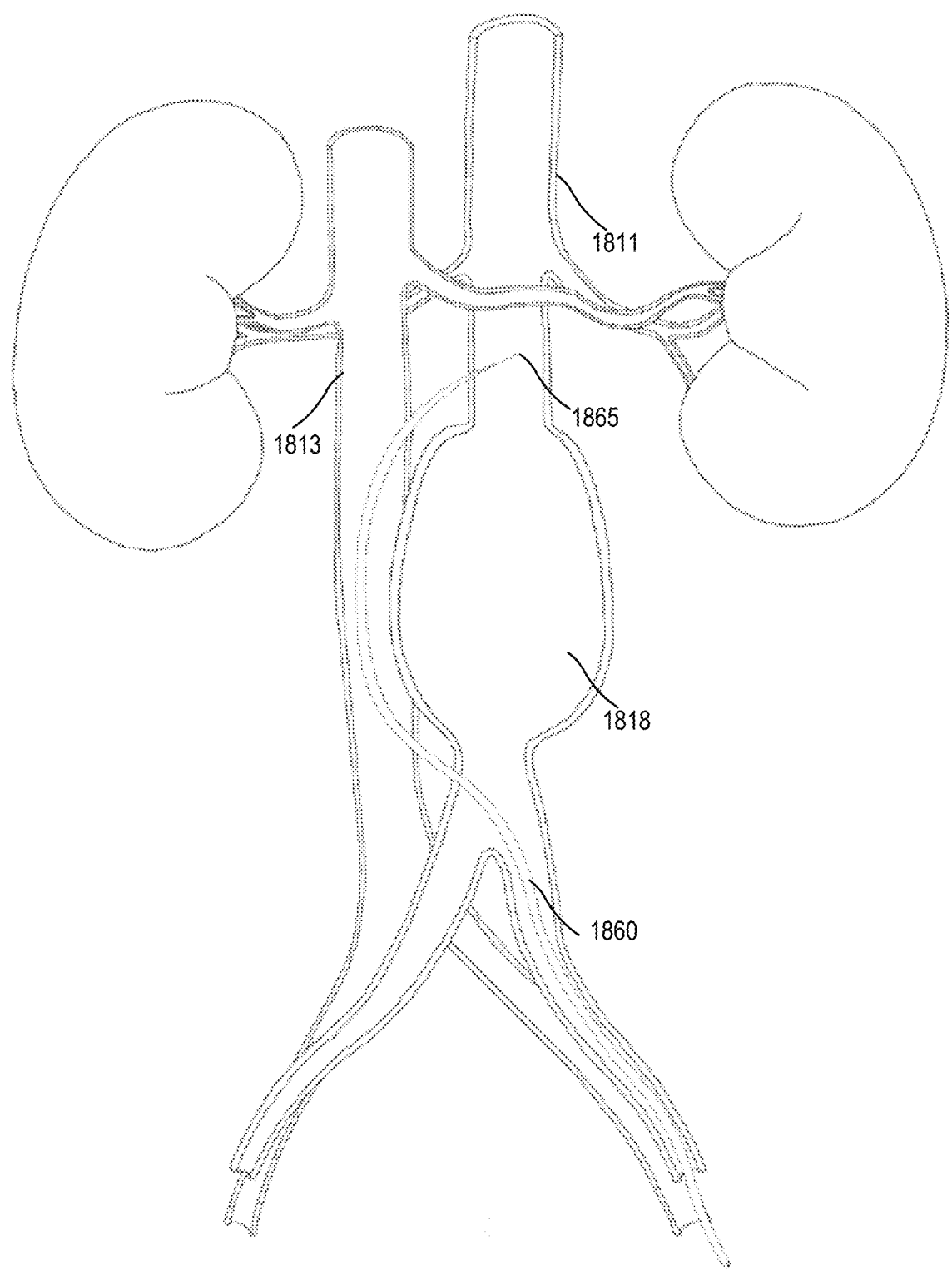
Figure 40D:
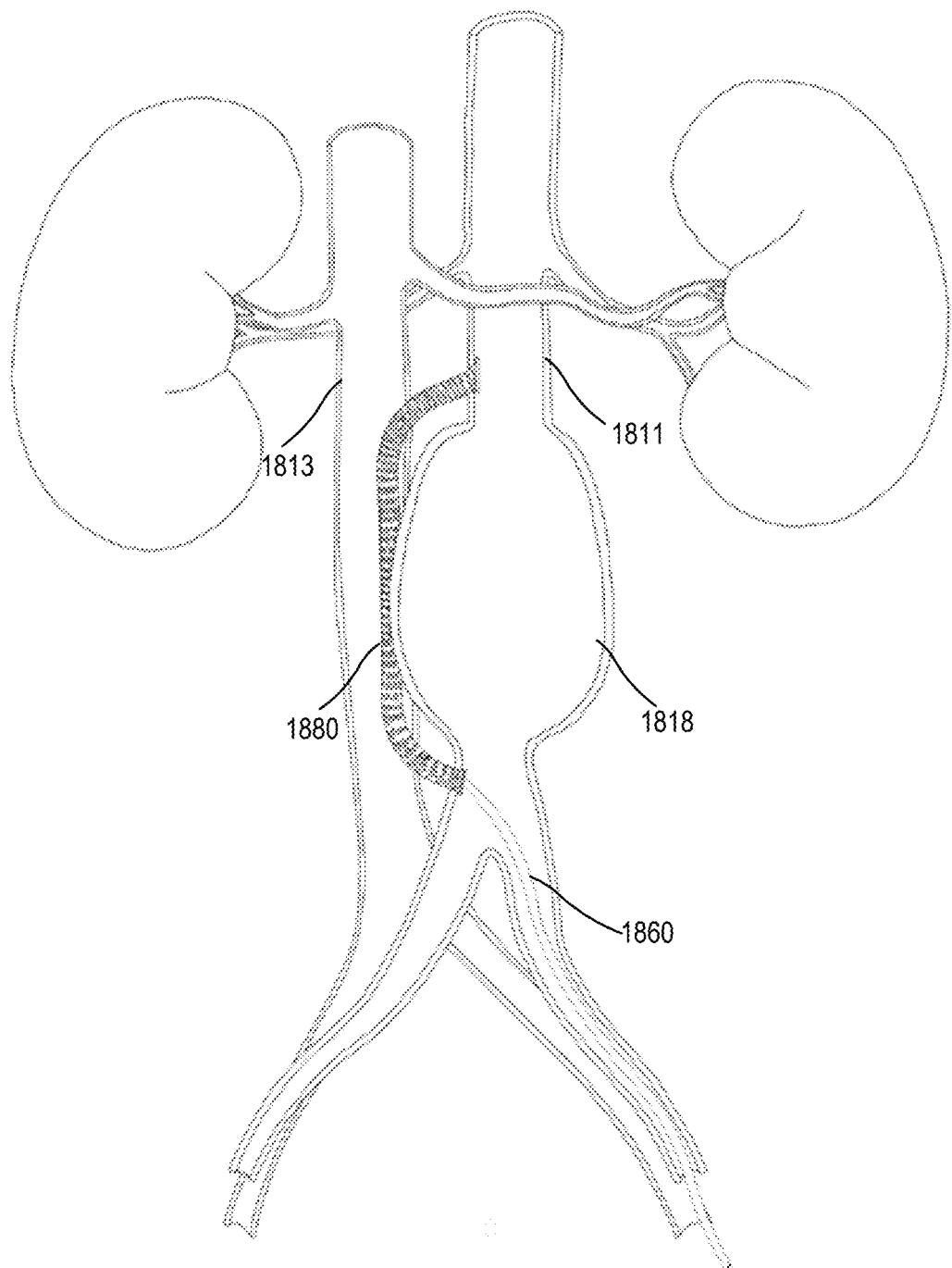
Figure 40E:
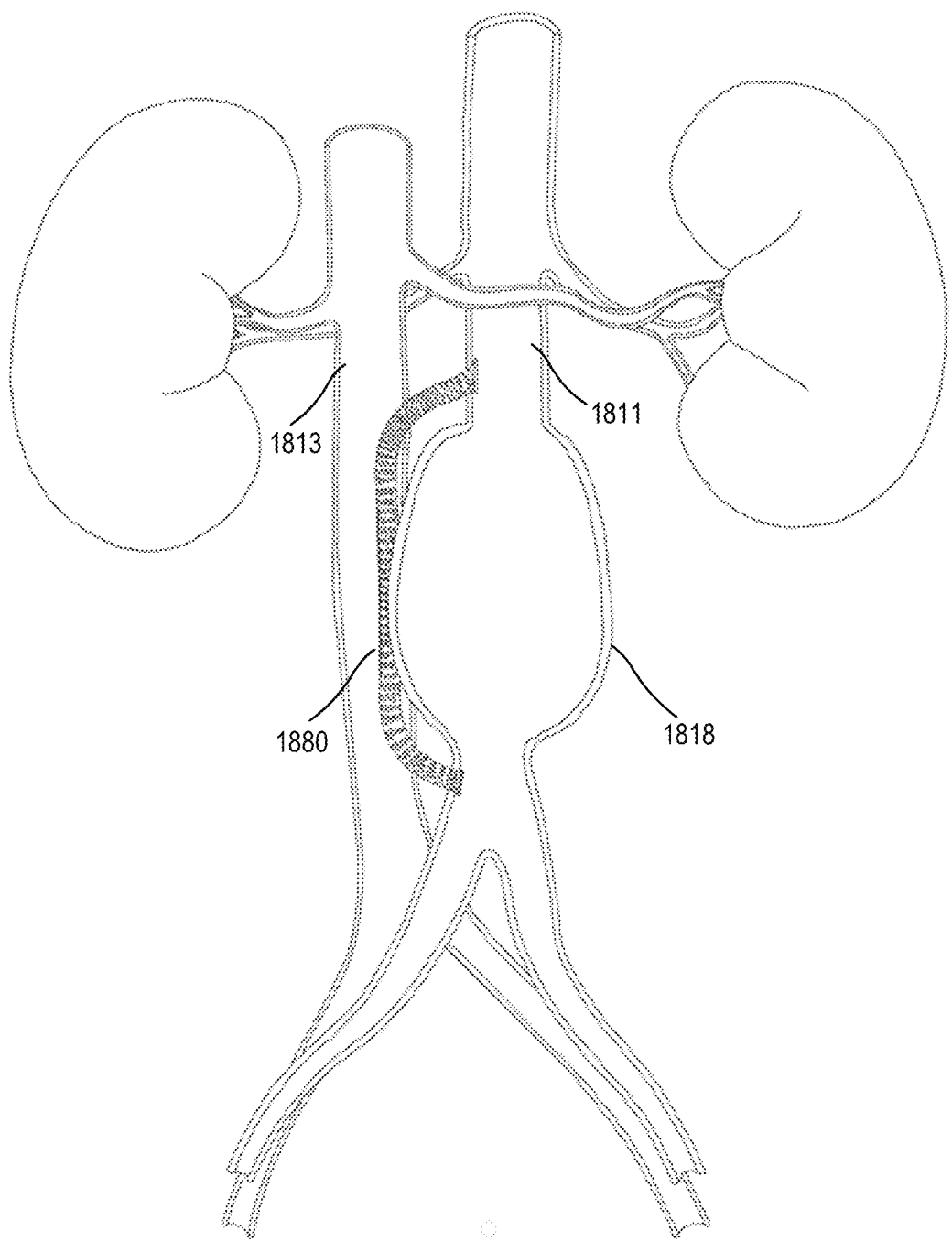

In some embodiments, implanting a bypass graft includes introducing a catheter 1860, as herein described, into an artery (e.g., femoral artery) of a subject. In some embodiments, after introducing the catheter 1860 into the artery, the method includes navigating the catheter 1860 within the artery to a first arterial puncture site 3704 disposed substantially near a first venous puncture site (FIG. 40B). In some embodiments, the catheter 1860 is then advanced through the first arterial puncture site and through the first venous puncture site and into the femoral vein (e.g., vena cava). In some embodiments, the catheter 1860 is then advanced to a second venous puncture site and through a second arterial puncture site (FIG. 40C). In some embodiments, the aneurysm sac 1818 is located between the first and second arterial puncture sites. In some embodiments, the first and second venous and arterial puncture sites are penetrated by a guidewire 1865 before the catheter 1860 is driven through each puncture site. In some embodiments, a graft is then advanced via the catheter through the first arterial puncture site, the first and second venous puncture sites and the second arterial puncture site. In some embodiments, a sealing structure is deployed at the first and second arterial puncture sites, thereby sealing fluid (e.g., blood) to flow through the graft and not pass into the vena cava. In some embodiments, the sealing structures are similar to the distal sealing structure and proximal sealing structure described herein. Accordingly, in some embodiments, fluid is able to flow through both the bypass graft 1880 and the aneurysm sac, whereas such reduction in pressure and/or flow through the aneurysm sac will alleviate the tension imposed thereto.

Figure 41A:
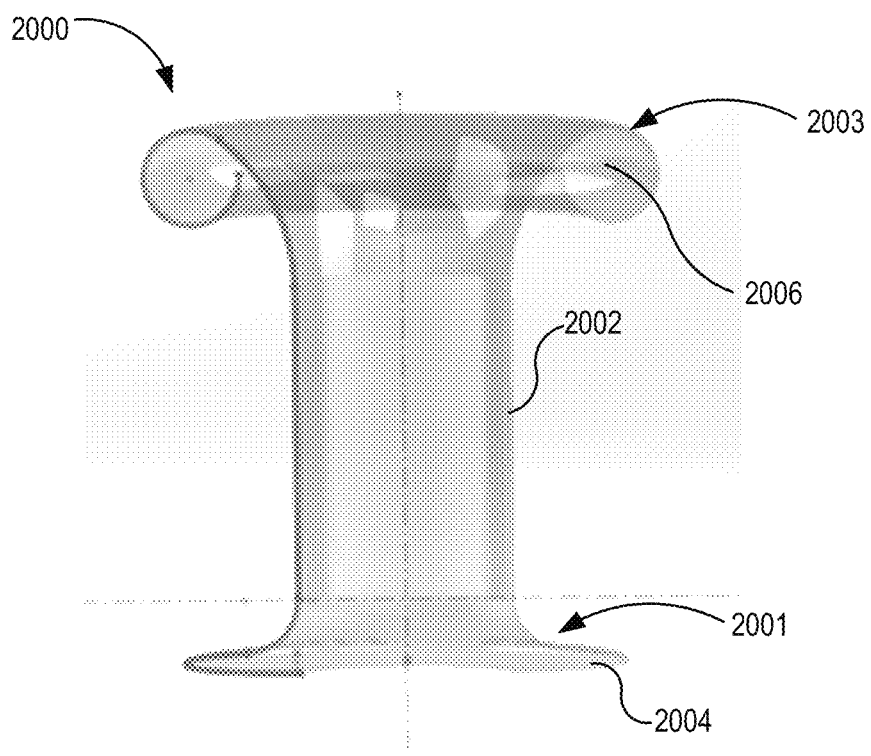
FIG. 41A shows a shunt including a self-rolling mechanism, according to embodiments.
Figure 41B:
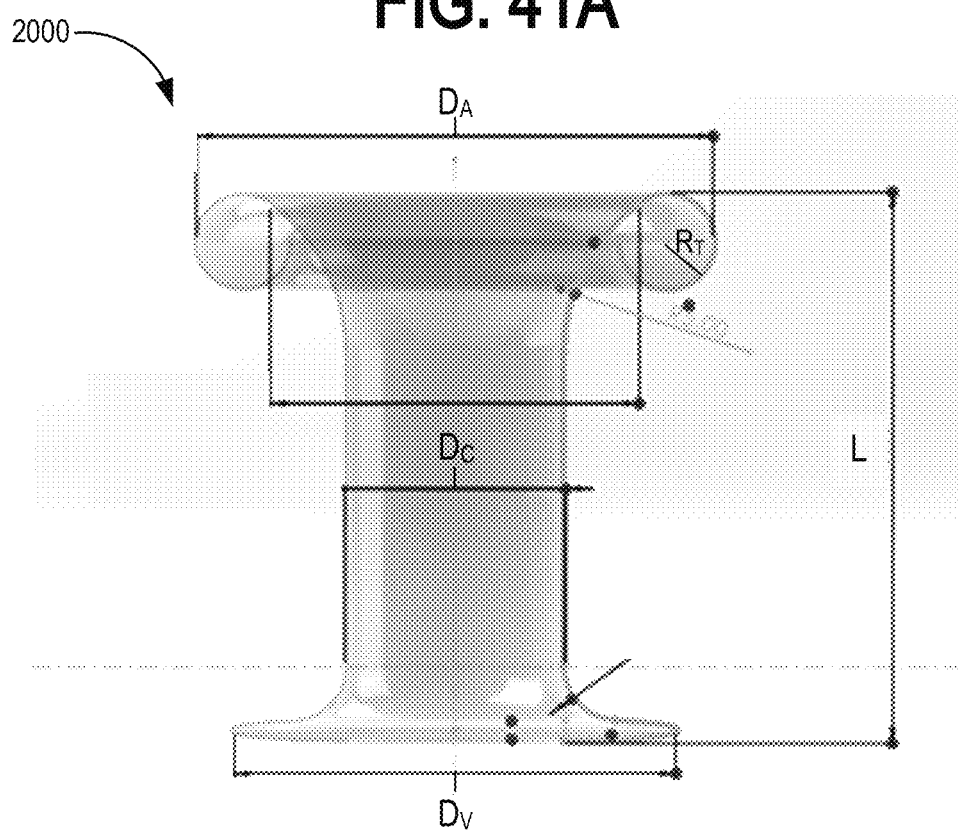
FIG. 41B shows dimensions of the shunt, according to embodiments.

FIGS. 41A-41B show a shunt 2000 including a self-rolling mechanism 2006 (e.g., a self-deployment, a self-adjusting, a self-sizing, an adjustable sizing mechanism), according to embodiments. The self-rolling mechanism 2006 of shunt 2000 may enhance performance, stability, and adaptability during and after deployment of the shunt 2000. The shunt 2000 may include a proximal end 2001 and a distal end 2003 and a central portion 2002 therebetween. The central portion 2002 may define a central lumen that serves as the conduit for blood flow, maintaining the patency of the vessel. The shunt 2000 may form a cylindrical shape in a delivery configuration and transition to an expanded, asymmetrical shape in the deployed configuration. The proximal end 2001 may include a venous sealing structure 2004 that forms a disc-like shape in the deployed configuration. For example, the proximal end 2001 may flare outward to help seal the proximal end 2001 of the shunt 2000 against the vessel wall. The proximal end 2001 of the shunt 2000 may create a broad surface area that forms a backstop against the vessel wall. This feature ensures a secure seal and prevents migration.

The distal end 2003 of the shunt 2000 may be configured to roll proximally such that the distal end 2003 forms a toroidal structure 2006 (e.g., torus, ring-like structure, etc.) as the shunt 2000 transitions from the delivery to the deployed configuration. In some embodiments, the distal end 2003 may curl outward and roll proximally such that the toroidal structure 2006 is positioned about an outer surface of the distal end 2003 of the shunt 2000. After the shunt 2000 is deployed, the distal end 2003 of the shunt 2000 may be configured to roll proximally and/or unroll distally to accommodate changing anatomy of the vessels and/or other anatomical or related forces. The toroidal structure 2006, which forms during deployment, acts as an anchor, securing the shunt 2000 in place and preventing it from migrating within the vessel. In some embodiments, as the shunt 2000 is deployed from the catheter, the distal end 2003 may roll proximally until the distal end 2003 abuts an inner surface of an arterial wall. In some embodiments, the toroidal structure 2006 may be configured to engage a thrombus in the artery (e.g., the aorta).

The shunt 2000 may be structurally and/or functionally similar to the shunt 100 or any other shunts described herein, and therefore, certain details of the shunt 2000 are not described in FIGS. 41A-41B.

FIG. 41B shows dimensions of the self-rolling stent 2000 in the deployed configuration. As shown, the shunt 2000 in the deployed configuration has a total deployed length L, a deployed diameter (e.g., a maximum outer diameter in the deployed configuration) $D_A$ of the distal end 2003, a deployed diameter (e.g., a maximum outer diameter in the deployed configuration) $D_P$ of the proximal end 2001, and a radius RT of the toroidal structure 2006. In some embodiments, as the distal end 2003 of the shunt 2000 rolls proximally, the total length of the shunt 2000 may decrease. In some embodiments, a delivery length (or a starting length) of the shunt 2000 (e.g., a total length of the shunt 2000 before rolling) may be in a range of about 10 mm to about 100 mm, inclusive of all ranges and subranges therebetween. In some embodiments, the total deployed length L of the shunt 2000 after rolling may decrease by up to 5%, up to 10%, up to 20%, up to 30%, up to 40%, up to 50%, up to 60%, up to 70%, or up to 80% after maximum rolling. For example, the shunt 2000 may have a delivery length of about 30 mm and a fully deployed length L (e.g., after maximum rolling) of about 5 mm. In some embodiments, the total deployed length L of the stent 2000 after deployment may be adjustable (e.g., may vary over time) between 5% of the total delivery length to 100% of the total delivery length. The diameter of the distal end 2003 may increase in a range of about 1% to about 500% from the delivery configuration to the deployed configuration, inclusive of all ranges and subranges therebetween. In some embodiments, when the distal end 2003 rolls proximally and/or unrolls distally, a diameter $D_B$ of the central portion 2002 may be equivalent or substantially equivalent before deployment and after deployment is completed. In some embodiments, the diameter $D_B$ of the central portion 2002 may be at least 1 mm, at least 2 mm, at least 3 mm, at least 4 mm, at least 5 mm, in the deployed configuration. In some embodiments, the diameter $D_B$ of the central portion 2002 may decrease as the distal end 2003 rolls and/or unrolls and then increase to the starting diameter of the central portion 2002 once the shunt 2000 is deployed. In some embodiments, the deployed diameter $D_V$ of the proximal end 2001 may be in a range of about 3 mm to about 20 mm, inclusive of all ranges and subranges therebetween. In some embodiments, the deployed diameter $D_A$ of the distal end 2003 is in a range of about 3 mm to about 25 mm, inclusive of all ranges and subranges therebetween. In some embodiments, the radius RT of the toroidal structure may be in a range of about 0.25 mm to about 10 mm, inclusive of all ranges and subranges therebetween. In some embodiments, the radius RT may be large enough to engage thrombus as the distal end 2001 rolls proximally.

The toroidal structure 2006 may provide the following benefits: adaptive self-sizing capability, enhanced anchoring and stability, proximal disc sealing, atraumatic ends, resheathablity and/or retrievability, better thrombus engagement than traditional stents, and/or insensitivity to delivery orientation. The self-rolling mechanism and toroidal structure 2006 can allow the shunt to 2000 (i) self-size (e.g., adjust a total length L of the shunt 2000, e.g., without user intervention) to different fluid pathway lengths between the arterial anchoring site and the venous anchoring site, and (ii) adapt to varying vessel geometries and anatomical changes over time. This mechanism is distinct from the expansion methods employed by some self-expanding shunts, for example, which typically expand radially without forming complex and functional shapes. An advantage of the toroidal structure 2006 in some use cases and implementations is its ability to accommodate a wide range of deployment configurations and/or geometry changes of the vessels. For example, the shunt 2000 can shorten (e.g., the distal end 2003 and proximal ends 2001 are close together), allowing the shunt 2000 to adapt to short vessel segments (e.g., less than 10 mm) or tight anatomical spaces. As another example, as the aneurysm sac or vessel diameter changes, the torus can continue to roll or unroll along the length of the shunt 2000, maintaining a secure and stable position. This adaptability is particularly beneficial in ensuring long-term stability and performance. This level of configurability is unparalleled in some traditional stent designs, which lack the ability to dynamically adjust their deployed length.

The deployed diameter $D_A$ (e.g., the maximum outer diameter) of the distal end 2003 (or the toroidal structure 2006), may be larger than the diameter $D_B$ of the central portion 2002, thereby creating a rivet-like anchoring effect. This feature, for example, may significantly reduce the risk of migration. The flared shape of the proximal end 2001 can provide a customized seal against the vessel wall, enhancing the shunt's 2000 sealing capabilities. The of the proximal end 2001 to deform and match the vessel's concavity ensures a secure and effective seal. The distal end 2003 and proximal end 2001 of the shunt 2000 are configured to maintain atraumatic surfaces within the lumen of the vessels they are anchored in. The toroidal mechanism 2006 in particular continues to provide an atraumatic surface as it adjusts during the life of the shunt 2000. This is advantageous in reducing risks of interference with other implants in the same vessel (e.g., an endograft).

In some embodiments, at least one of the distal end 2003 and proximal end 2001 of the shunt 2000 can be configured to be resheathed, allowing precise deployment at the time of implantation. For example, the shunt 2000 can be repositioned such that a tight seal is formed between the shunt 2000 and the vessels. By design, the toroidal shape 2006 may be resheathed without compromising the anchoring mechanism. Similarly, in the event that the implant needs to be removed, the toroidal design allows for a safe removal from the vessel as the distal end 2001 may "unroll" and be moved back into the catheter.

The deployment of the shunt 2000 in some implementations involves the use of a retractable outer catheter sheath. The shunt 2000 may be initially compressed within the sheath, allowing it to be navigated through the vascular system to the target site. Once the shunt 2000 is in position (e.g., across the puncture sites), the outer sheath can be gradually withdrawn proximally, allowing the shunt 2000 to deploy. In some embodiments, deployment of shunt 2000 may include the distal end 2003 rolling proximally as the outer sheath exposes the distal end 2003 and then the proximal end 2001 expanding radially to form the disc-like shape as the outer sheath exposes the proximal end 2001. The flared disc provides a backstop against the vessel wall, applying a sealing force that enhances the stability and sealing capabilities of the shunt 2000.

Figure 42A:
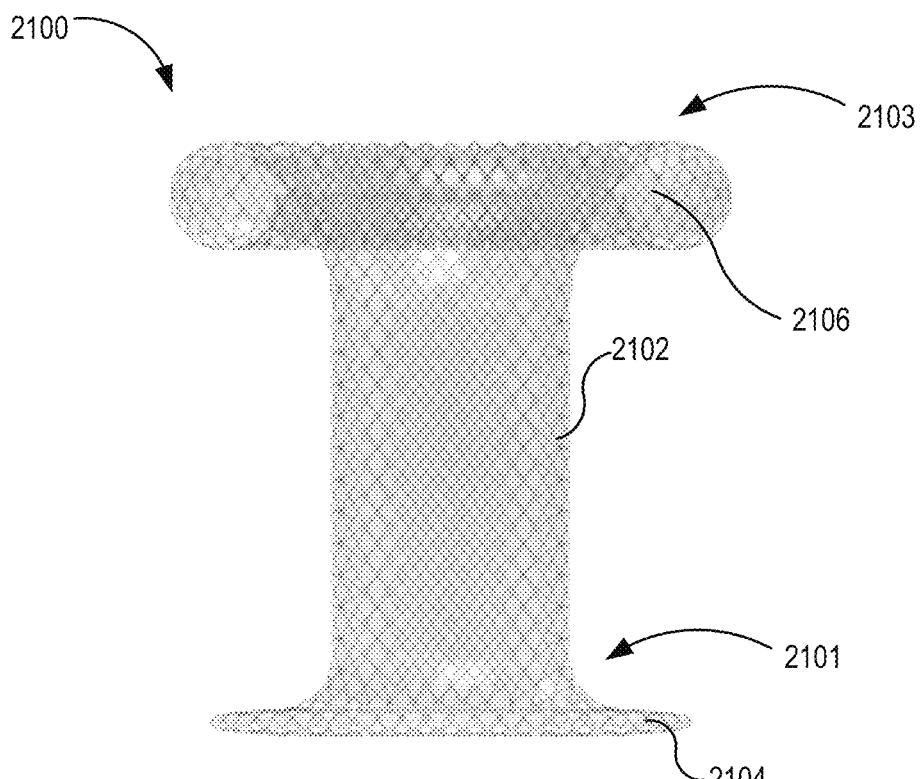
FIGS. 42A-42B show a self-rolling shunt including a braided metal alloy, according to embodiments.
Figure 42B:
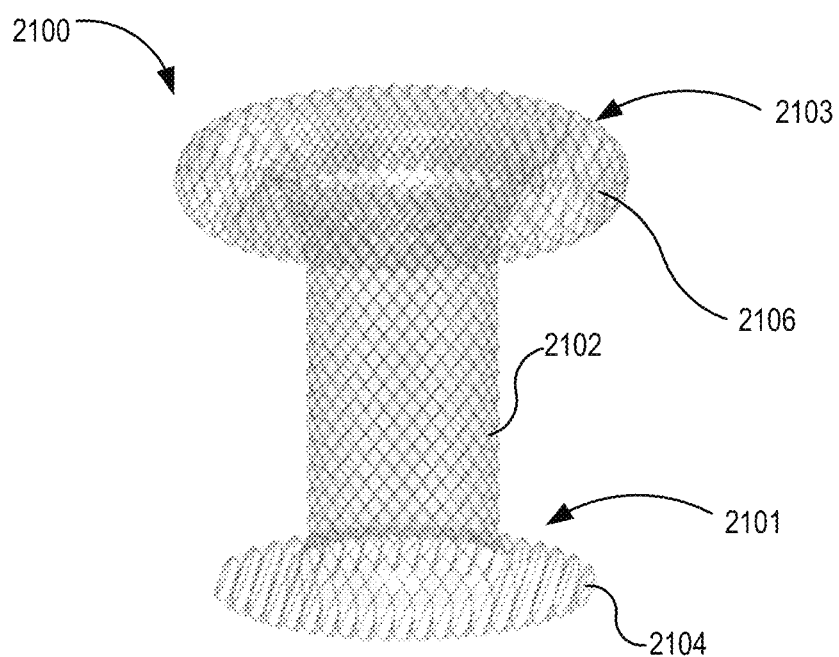

FIGS. 42A-42B show a self-rolling shunt 2100 including braided metal alloy, according to embodiments. As shown, the distal end 2103 of the shunt 2100 includes a toroidal structure 2106, a proximal end 2101 of the shunt 2000 forms a disc-like sealing structure 2104, and a central portion 2102 of the shunt 2000 defines a lumen between the distal end 2103 and the proximal end 2101. In some embodiments, the shunt 2200 may include braided nitinol, which enables the shunt 2200 to form the toroidal structure 2206 during deployment. In some implementations, a heat-setting process can be used in manufacturing the shunt 2200 to ensure that it retains flexibility and durability, allowing it to function effectively in clinical settings. The heat-setting process involves shaping the nitinol braid into the desired configuration (e.g., the toroidal structure 2206) and heating the shunt 2200 to a specific temperature to set the shape. The braided design of the nitinol also allows the stent to be highly flexible, enabling it to conform to the natural curves and variations in the vessel (or other) anatomy. The flexible braided nitinol allows the proximal end 2201 to deform and match the concavity of the vessel, providing a customized fit and enhancing the sealing effect. The shunt 2100 may be structurally and/or functionally similar to the shunts 100, 2000, or any other shunts described herein, and therefore, certain details of the shunt 2100 are not described in FIGS. 42A-42B.

FIGS. 43A-43G are images of a self-rolling shunt 2200 transitioning from a delivery configuration to a deployed configuration, according to embodiments. As shown in FIG. 43A, the distal end 2203 of the shunt 2200 begins to extend distally from a distal end of the catheter 2260. In FIGS. 43B-43D, the distal end 2203 of the shunt begins to roll proximally. In FIG. 43E, the central portion 2202 is deployed and a proximal end 2201 of the shunt 2200 begins to be deployed from the distal end of the catheter 2260. As shown, the proximal end 2201 begins to expand radially as it is deployed from the catheter 2260. FIGS. 43F-43G show the proximal end 2201 of the shunt 2200 forming the disc-like shape, and a diameter of the central portion 2202 widens. As shown in FIG. 43G, the shunt 2200 when deployed includes the toroidal structure at the distal end 2203, the central portion 2202, and the disc-like proximal end 2201. The shunt 2200 may be structurally and/or functionally similar to the shunt 100, 2000, 2100, or any other shunts described herein, and therefore, certain details of the shunt 2200 are not described in FIGS. 43A-43G.

In some embodiments, the shunts 2000, 2100, 2200 can be implanted in locations other than between vein and artery, and although referred to as the arterial sealing structure 2006, 2106, 2206 and the venous sealing structure 2004, 2104, 2204, it should be appreciated the arterial sealing structure 2006, 2106, 2206 and venous sealing structure 2004, 2104, 2204 can be configured for other parts of the anatomy (e.g., other than the aorta).

Applications of Self-Rolling Shunt:

1. Interatrial Shunting:

The self-rolling shunt (e.g., shunts 100, 2000, 2100, 2200) may be used as an interatrial shunt for management of various cardiac conditions, such as heart failure. In patients with heart failure, creating an interatrial shunt can help decompress the left atrium and reduce pulmonary congestion. These shunts create a controlled communication between the left and right atria, allowing for the regulation of pressure and blood flow between the heart chambers, thereby improving hemodynamics and reducing symptoms such as shortness of breath and fluid retention. Traditional methods for creating interatrial shunts include surgical procedures and transcatheter device placements, each with its own set of challenges. Shortcomings of existing solutions for interatrial shunts are that they are highly invasive, requiring open-heart surgery and cardiopulmonary bypass, which carries significant risks including infection, prolonged recovery times, and complications related to the surgery itself. Transcatheter device placements, while less invasive, often face challenges such as device migration, incomplete closure, and difficulties in achieving a precise fit within the interatrial septum.

The self-rolling shunt deployed via a transcatheter approach is significantly less invasive than surgical procedures. This reduces procedural risks and recovery times, making it a safer option for patients with heart failure. The self-rolling shunt can be used to create a precise and adaptable interatrial shunt. For example, the toroidal structure can provide a secure anchoring mechanism within the interatrial septum, thereby (1) creating stable and effective communication between the atria and/or (2) minimizing the risk of device migration or embolization. Furthermore, the self-sizing capability of the shunt allows it to adapt to variations in the thickness and/or shape of the interatrial septum. This adaptability promotes or ensures a precise and secure fit, which also can reduce the risk of migration and improve the overall efficacy of the shunt. This secure anchoring is a significant improvement over traditional transcatheter devices, which often face issues with stability. In implementations in which the shunt includes a braided nitinol construction, such construction of the shunt can be highly biocompatible, reducing the risk of infection and thrombus formation. The smooth and flexible design, in some implementations, promotes optimal blood flow, further minimizing the likelihood of complications. By creating a stable and effective interatrial shunt, the self-rolling shunt may help regulate pressure and/or blood flow between the atria, improving symptoms and outcomes for patients with heart failure. This leads to better long-term management of these conditions and enhanced quality of life for patients. The shunt can be used in various anatomical configurations, making it suitable for a wide range of interatrial shunt applications. This versatility increases the success rate of the procedure and expands its applicability to different patient populations.

2. Hemodialysis Access

The self-rolling shunt (e.g., shunts 100, 2000, 2100, 2200) may be used for hemodialysis access. Chronic kidney disease (CKD) affects millions worldwide, necessitating regular hemodialysis to filter waste and excess fluids from the blood. Effective hemodialysis requires reliable vascular access, which is typically achieved through arteriovenous (AV) fistulas or AV grafts. AV fistulas involve connecting an artery directly to a vein, usually in the arm, creating a robust access point that can withstand repeated needle insertions for dialysis sessions. AV grafts, on the other hand, use a synthetic tube to connect the artery and vein, providing an alternative when a fistula is not viable. Current AV fistulas and grafts have several limitations. For example, AV fistulas can take several weeks to months to mature before they are usable for dialysis, and the success of their creation is highly dependent on the patient's vascular anatomy. They also have a significant failure rate due to issues like thrombosis, stenosis, and infection. AV grafts, while usable sooner, have higher rates of complications, including infections and thrombosis, and typically have a shorter lifespan than fistulas.

The self-rolling shunt offers a solution for hemodialysis access by providing a secure anchoring mechanism within the vessel. The shunt's ability to roll and unroll allows it to adapt dynamically to varying vessel sizes and conditions. Advantages over traditional AV Fistulas and grafts include: (1) providing a secure anchoring effect and/or (2) preventing migration and/or minimizing the risk of thrombosis and/or stenosis. The self-rolling capability promotes or ensures the shunt fits effectively or snugly within the vessel, adapting to changes over time and reducing the likelihood of complications. The self-rolling shunt may also control infection, in some use cases. For example, the use of nitinol, known for its biocompatibility, reduces the risk of infection compared to synthetic grafts currently used. Additionally, the streamlined design of the shunt minimizes potential sites for bacterial colonization. The self-rolling feature allows the shunt to be used in a broader range of vascular anatomies, making it suitable for patients who may not be ideal candidates for traditional fistulas or grafts. This versatility increases the success rate of creating functional dialysis access. The nitinol material provides superior durability, ensuring the shunt remains functional for extended periods. This longevity reduces the need for repeated surgical interventions, improving patient quality of life and reducing healthcare costs.

3. Peripheral Vascular Disease

The self-rolling shunt (e.g., shunts 100, 2000, 2100, 2200) may be used for treating Peripheral Vascular Disease. Peripheral vascular disease (PVD) is characterized by the narrowing or blockage of arteries outside the heart, most commonly affecting the legs. PVD can lead to critical limb ischemia (CLI), where the reduced blood flow causes severe pain, ulcers, and potentially limb loss. Traditional treatments for PVD include angioplasty, stenting, and bypass surgery, each with its own set of challenges and limitations. Angioplasty and stenting, while less invasive, often fail to provide long-term relief due to restenosis, where the artery narrows again. Bypass surgery, although more durable, is highly invasive and not suitable for all patients, particularly those with significant comorbidities. These treatments also face issues like graft occlusion and infection, impacting their overall effectiveness and patient outcomes.

The self-rolling shunt can be used to bypass occluded or stenotic segments of peripheral arteries, restoring adequate blood flow to ischemic tissues. The toroidal structure ensures a secure fit within the vessel, preventing migration and reducing the risk of occlusion. The toroidal structure of the shunt also provides a stable anchor, minimizing the likelihood of restenosis. The deployment of the self-rolling shunt is less invasive than traditional bypass surgery, reducing recovery times and procedural risks. This is particularly beneficial for high-risk patients who may not tolerate extensive surgery. The self-rolling capability allows the shunt to adapt to changes in vessel diameter, maintaining patency and/or limiting or preventing re-narrowing. The durable braided nitinol construction, in some such implementations, ensures the shunt remains functional over extended periods, reducing the need for repeat interventions. This durability is a significant improvement over the shorter lifespan of angioplasty and stents. The smooth, flexible design of the shunt, in some such embodiments, promotes optimal blood flow, reducing turbulence and the associated risk of thrombus formation. This leads to better overall outcomes for patients with PVD. The self-rolling feature allows the shunt to be used in various anatomical configurations, making it suitable for a wide range of PVD cases. This adaptability ensures a higher success rate in restoring blood flow to ischemic limbs.

4. Congenital Heart Defects

Congenital heart defects (CHDs) such as hypoplastic left heart syndrome (HLHS) and atrial septal defects (ASDs) require complex surgical interventions to manage abnormal blood flow between the heart's chambers and the systemic and pulmonary circulations. Traditional treatments involve multiple surgeries, often with significant risks and complications. Current surgical approaches for CHDs, such as the Norwood procedure for HLHS, are highly invasive and carry substantial risks, including infection, heart failure, and arrhythmias. These procedures often require multiple stages, each with its own recovery period and potential for complications. Additionally, there are limited options for less invasive treatments that can effectively manage these complex conditions.

The self-rolling shunt (e.g., shunts 100, 2000, 2100, 2200), in some embodiments, can be used to create controlled communications between the atria or between the systemic and pulmonary circulations, helping to balance oxygenated and deoxygenated blood flow. This approach can be tailored to the specific anatomical and physiological needs of each patient and can provide a less invasive alternative to traditional surgeries. The deployment of the self-rolling shunt can be less invasive than traditional open-heart surgeries, thereby reducing procedural risks and recovery times. This can be beneficial for infants and young children with CHDs, who are more vulnerable to surgical complications. In some embodiments, the self-rolling capability of the shunt can allow the shunt to adapt to the unique anatomical structures of each patient, enabling a precise and effective fit. This customization improves the efficacy of the treatment and reduces the likelihood of complications. The toroidal structure of the shunt, in some embodiments, can provide a secure anchor, thereby minimizing the risk of dislodgement and migration. The shunt can include durable braided nitinol construction in some embodiments, which can reduce the risk of infection and enhances long-term performance. The shunt can be used as part of a staged surgical approach, providing immediate relief and stabilization while preparing for more complex interventions. This flexibility can enable the shunt to manage progressive conditions like HLHS. The shunt may improve patient outcomes by promoting optimal blood flow dynamics, thereby reducing the workload on the heart and improving overall cardiac function. This leads to better long-term outcomes and quality of life for patients with CHDs.

5. Portosystemic Shunts

Portal hypertension, commonly resulting from liver cirrhosis, leads to elevated pressure in the portal vein. This condition can cause severe complications, such as variceal bleeding, ascites, and hepatic encephalopathy. Traditional treatments include medication, endoscopic interventions, and surgical shunts, but these methods have limitations and risks. Medications often provide only symptomatic relief and do not address the underlying pressure. Endoscopic interventions, such as variceal banding, require repeated procedures and do not prevent future bleeding. Surgical shunts, including the Transjugular Intrahepatic Portosystemic Shunt (TIPS), while effective, carry risks of shunt dysfunction, hepatic encephalopathy, and infection.

In some embodiments, the self-rolling shunt (e.g., shunts 100, 2000, 2100, 2200) can be used to create a controlled portosystemic shunt, diverting blood from the high-pressure portal vein to a lower-pressure systemic vein. This approach can reduce portal pressure and mitigate the complications of portal hypertension. The deployment of the self-rolling shunt may be less invasive than traditional surgical shunts, reducing procedural risks and recovery times. Lower invasiveness can be advantageous for patients with advanced liver disease, who may not tolerate extensive surgery. In some embodiments, the self-rolling capability of the shunt enables the shunt to adapt to changes in portal pressure and vessel diameter, maintaining effective blood flow diversion over time. The adaptability of the shunt, in certain aspects, can provide advantages over fixed-diameter shunts, which may become less effective as conditions change. The toroidal structure of the shunt can provide a secure anchor, minimizing the risk of migration and dysfunction. In some embodiments, the shunt can include durable braided nitinol construction, which can reduce the risk of infection and enhances long-term patency. By reducing portal pressure, the self-rolling shunt can decrease the risk of variceal bleeding and other complications of portal hypertension, which can promote improved patient outcomes and quality of life. The shunt can be used in various anatomical configurations, making it suitable for a wide range of patients with portal hypertension. This versatility can increase the success rate of the procedure and expands its applicability.

6. Traumatic Injuries

Severe trauma, such as that resulting from accidents or combat injuries, can cause vascular damage that requires immediate intervention to preserve limb function. Rapid revascularization is critical to prevent tissue ischemia and necrosis. Traditional methods for managing vascular trauma include surgical repair and temporary vascular shunts. Surgical repair is time-consuming and may not be feasible in unstable patients. Temporary vascular shunts, while effective for immediate revascularization, are often bulky, difficult to secure, and prone to dislodgement.

The self-rolling shunt (e.g., shunts 100, 2000, 2100, 2200) can provide a rapid and reliable solution for revascularization in traumatic injuries. In some embodiments, the toroidal structure of the shunt can promote secure anchoring within the vessel, maintaining blood flow to injured limbs until definitive surgical repair can be performed. One advantage of traditional shunts is that the shunt may be rapidly deployed. For example, the self-rolling shunt can be quickly deployed in emergency settings, restoring blood flow within minutes. This speed can prevent tissue damage and promote improvement in outcomes in trauma patients. In some embodiments, the toroidal structure can provide a stable anchor, preventing dislodgement even in the dynamic environment of trauma care. The stability provides improvements over traditional temporary shunts, which are prone to movement and failure. The self-rolling capability may allow the shunt to adapt to various vessel sizes and configurations, promoting a precise fit in diverse anatomical situations. This adaptability can enhance the effectiveness of the shunt in maintaining blood flow. In some embodiments, the shunt can include a durable braided nitinol construction, which can minimize the risk of infection and thrombosis, which are common issues with traditional shunts. In some embodiments, the shunt may include a smooth, flexible design which can promote optimal blood flow, reducing the risk of further complications. By providing reliable and secure revascularization, the self-rolling shunt can improve likelihood of limb salvage and recovery. This can lead to better overall outcomes for trauma patients, reducing morbidity and mortality.

7. Cerebral Arteriovenous Malformations

Cerebral arteriovenous malformations (AVMs) are abnormal connections between arteries and veins in the brain, which can lead to serious complications such as hemorrhage, seizures, and neurological deficits. Traditional treatments include surgical resection, embolization, and stereotactic radiosurgery, each with varying degrees of invasiveness and risk. Surgical resection is highly invasive and carries risks of significant neurological damage. Embolization, while less invasive, often requires multiple procedures and carries a risk of incomplete treatment and recanalization. Stereotactic radiosurgery has delayed effects and may not fully resolve the AVM, leaving a residual risk of hemorrhage.

The self-rolling shunt (e.g., shunts 100, 2000, 2100, 2200) can be used as part of a treatment strategy for cerebral AVMs, helping to reroute blood flow and reduce pressure within the malformation. This approach can offer a less invasive alternative to traditional treatments. In some embodiments, the deployment of the self-rolling shunt can be less invasive than surgical resection, reducing procedural risks and recovery times. Reducing invasiveness and procedural risks can be beneficial for patients with AVMs located in critical or deep brain regions. The self-rolling capability, in some embodiments, can allow the shunt to adapt to changes in vessel diameter and blood flow dynamics, maintaining effective treatment over time. This adaptability provides an improvement over static embolization materials, which may not fully adapt to changing conditions. In some embodiments, the toroidal structure of the shunt can provide a secure anchor, minimizing the risk of dislodgement and migration. In some embodiments, the shunt can include a durable braided nitinol construction, which can reduce the risk of infection and enhance long-term performance. By rerouting blood flow and reducing pressure within the AVM, the self-rolling shunt can decrease the risk of hemorrhage and other complications, which can lead to improved patient outcomes and quality of life. The shunt can be used in various anatomical configurations, making it suitable for a wide range of AVMs. This versatility can increase the success rate of the procedure and expand its applicability.

8. Coronary Artery Disease

Coronary artery disease (CAD) is characterized by the narrowing or blockage of coronary arteries, leading to insufficient blood flow to the heart muscle. This condition can cause angina, heart attacks, and other serious cardiac events. Traditional treatments include medications, angioplasty with stenting, and coronary artery bypass grafting (CABG). Medications provide symptomatic relief but do not address the underlying arterial blockage. Angioplasty and stenting, while effective for opening blocked arteries, have limitations such as restenosis and stent thrombosis. CABG, though durable, is highly invasive and not suitable for all patients, especially those with comorbidities.

In some embodiments, the self-rolling shunt (e.g., shunts 100, 2000, 2100, 2200) can be used to create controlled communications between coronary arteries and veins, improving myocardial perfusion. This approach can provide a potential new treatment for severe cases of CAD. The deployment of the self-rolling shunt can be less invasive than CABG, which can reduce procedural risks and recovery times. The reduced invasiveness can be advantageous for high-risk patients who may not tolerate extensive surgery. In some embodiments, the self-rolling capability can allow the shunt to adapt to changes in coronary artery diameter and blood flow dynamics, maintaining effective perfusion over time. This adaptability can provide improvements over fixed stents, which may become less effective as conditions change. In some embodiments, the toroidal structure of the shunt can provide a secure anchor, minimizing the risk of dislodgement and thrombosis. In some embodiments, the shunt includes a durable braided nitinol construction, which can reduce the risk of restenosis and enhances long-term patency. By enhancing myocardial perfusion, the self-rolling shunt can reduce symptoms of angina and improve overall cardiac function, which can lead to better long-term outcomes and quality of life for patients with severe CAD. The shunt can be used in various anatomical configurations, making it suitable for a wide range of CAD cases.

9. Pulmonary Hypertension

Pulmonary hypertension (PH) is characterized by elevated pressure in the pulmonary arteries, leading to right heart failure and significant morbidity. Traditional treatments include medications, oxygen therapy, and lung transplantation, each with varying degrees of effectiveness and risk. Medications often provide symptomatic relief but do not address the underlying elevated pressure in the pulmonary arteries. Oxygen therapy is supportive but not curative, and lung transplantation, while potentially curative, carries significant risks and is limited by donor availability. These treatments do not offer a comprehensive solution for managing pulmonary hypertension.

The self-rolling shunt (e.g., shunts 100, 2000, 2100, 2200) can be used to create controlled shunts between systemic and pulmonary circulations, reducing pressure in the pulmonary arteries. This approach offers a new treatment option for managing pulmonary hypertension. The deployment of the self-rolling shunt can be less invasive than lung transplantation, reducing procedural risks and recovery times. The reduced invasiveness can be advantageous for patients with severe pulmonary hypertension who may not tolerate extensive surgery. The self-rolling capability may enable the shunt to adapt to changes in vessel diameter and pressure dynamics, maintaining effective pressure reduction over time. This adaptability can provide improvements over fixed treatments, which may become less effective as conditions change. In some embodiments, the toroidal structure of the shunt can provide a secure anchor, minimizing the risk of dislodgement and dysfunction. In some embodiments, the shunt may include a durable braided nitinol construction, which can reduce the risk of infection and enhances long-term performance. By reducing pressure in the pulmonary arteries, the self-rolling shunt can decrease the workload on the right heart and improves overall cardiac function, which can lead to better long-term outcomes and quality of life for patients with pulmonary hypertension. The shunt can be used in various anatomical configurations, making it suitable for a wide range of pulmonary hypertension cases.

10. Cancer Treatment

Delivering high doses of chemotherapy directly to tumors while minimizing systemic exposure is crucial for effective cancer treatment. Traditional systemic chemotherapy often results in significant side effects due to the widespread distribution of the drugs throughout the body. Systemic chemotherapy, while effective in targeting cancer cells, also affects healthy cells, leading to severe side effects such as nausea, hair loss, and immunosuppression. Localized delivery methods, such as intra-arterial chemotherapy, can be more effective but are technically challenging and have limited applicability.

In some embodiments, the self-rolling shunt (e.g., shunts 100, 2000, 2100, 2200) can be used to deliver chemotherapy directly to the tumor site, enhancing drug concentration at the target while reducing systemic side effects. This approach can offer a new method for localized cancer treatment. In some embodiments, the self-rolling shunt can enable precise delivery of chemotherapy directly to the tumor, increasing drug concentration at the target site and improving treatment efficacy. This localization can reduce the impact on healthy tissues and minimizes systemic side effects. The self-rolling capability can allow the shunt to adapt to changes in vessel diameter and tumor growth, maintaining effective drug delivery over time. This adaptability can provide improvements over fixed delivery methods, which may become less effective as conditions change. In some embodiments, the toroidal structure of the shunt can provide a secure anchor, minimizing the risk of dislodgement and dysfunction. In some embodiments, the shunt can include a durable braided nitinol construction, which can reduce the risk of infection and enhances long-term performance, in some use cases. By enhancing the concentration of chemotherapy at the tumor site, the self-rolling shunt can improve treatment efficacy and reduces the likelihood of tumor recurrence, which can lead to better long-term outcomes and quality of life for cancer patients. The shunt can be used in various anatomical configurations, making it suitable for a wide range of tumor locations.

11. Venous Insufficiency

Chronic venous insufficiency (CVI) is characterized by poor blood flow in the veins, leading to symptoms such as swelling, pain, and ulceration. Traditional treatments include compression therapy, sclerotherapy, and surgical interventions. Compression therapy provides symptomatic relief but does not address the underlying venous insufficiency. Sclerotherapy and surgical interventions, while effective, carry risks of complications and may require repeated treatments. These methods do not offer a comprehensive solution for managing CVI.

In some embodiments, the self-rolling shunt (e.g., shunts 100, 2000, 2100, 2200) can be used to improve blood flow in the affected veins, alleviating symptoms and promoting healing. This approach can offer a new treatment option for managing chronic venous insufficiency. The deployment of the self-rolling shunt can be less invasive than surgical interventions, reducing procedural risks and recovery times. This can be advantageous for patients with severe venous insufficiency who may not tolerate extensive surgery. In some embodiments, the self-rolling capability allows the shunt to adapt to changes in vessel diameter and blood flow dynamics, maintaining effective treatment over time. This adaptability can provide improvements over static treatments, which may become less effective as conditions change. The toroidal structure of the shunt can provide a secure anchor, minimizing the risk of dislodgement and dysfunction. In some embodiments, the shunt may include a durable braided nitinol construction, which can reduce the risk of infection and enhance long-term performance. By improving blood flow in the affected veins, the self-rolling shunt can alleviate symptoms and promotes healing. This can lead to better long-term outcomes and quality of life for patients with chronic venous insufficiency. The shunt can be used in various anatomical configurations, making it suitable for a wide range of venous insufficiency cases.

12. Transcaval Shunt for Abdominal Aortic Aneurysm

Abdominal aortic aneurysms (AAAs) are a life-threatening condition characterized by the abnormal dilation of the abdominal aorta, which can lead to rupture and severe internal bleeding. Traditional treatments include open surgical repair and endovascular aneurysm repair (EVAR). Open surgical repair, while effective, is highly invasive and carries significant risks, including prolonged recovery times and complications such as infection and cardiovascular events. EVAR, although less invasive, is associated with issues such as endoleaks, stent migration, and the need for long-term surveillance and potential reinterventions.

The shunts described herein, for example, the self-rolling shunt (e.g., shunts 100, 2000, 2100, 2200), can be used to create a transcaval shunt, providing a controlled communication between the aorta and the inferior vena cava. This approach can reduce pressure within the aneurysm sac, preventing rupture and offering a new method for managing AAAs. The deployment of the self-rolling shunt can be less invasive than open surgical repair, reducing procedural risks and recovery times. This can be advantageous for high-risk patients who may not tolerate extensive surgery. The self-rolling capability can allow the shunt to adapt to changes in vessel diameter and aneurysm dynamics, maintaining effective pressure reduction over time. This adaptability can provide improvements over fixed stents, which may become less effective as conditions change. In some embodiments, the toroidal structure of the shunt can provide a secure anchor, minimizing the risk of migration and endoleaks. In some embodiments, the shunt may include a durable braided nitinol construction, which can reduce the risk of infection and enhance long-term performance. By reducing pressure within the aneurysm sac, the self-rolling shunt can decrease the risk of rupture and improves overall patient outcomes. This can lead to better long-term outcomes and quality of life for patients with AAAs. The shunt can be used in various anatomical configurations, making it suitable for a wide range of AAA cases.

13. Research and Experimental Therapies

Understanding blood flow dynamics, vascular biology, and the development of new therapeutic techniques are critical areas of medical research. Experimental models are essential for studying the physiological responses to different interventions and for developing innovative treatments. Traditional research models, including animal studies and in vitro simulations, have limitations in replicating human vascular conditions accurately. These models often lack the dynamic adaptability and physiological complexity needed to fully understand the effects of new treatments.

In some embodiments, the self-rolling shunt (e.g., shunts 100, 2000, 2100, 2200) can be used in research settings to study the effects of altered blood flow on vascular health, wound healing, and the development of new vascular devices and treatments. The shunt may include properties (e.g., adaptability, flexibility, self-rolling mechanism, biocompatibility, etc.) make it an ideal tool for experimental therapies. The self-rolling shunt can provide advantages over existing research tools such as realistic physiological modeling. For example, the self-rolling shunt can provide a more accurate replication of human vascular conditions, enhancing the validity of research findings. This realism can be useful for understanding the physiological responses to new treatments. The self-rolling capability can allow the shunt to adapt to changes in vessel diameter and blood flow dynamics, providing a flexible model for studying various conditions. This adaptability can provide improvements over static models, which cannot replicate dynamic physiological changes. In some embodiments, shunt can be used in a wide range of research applications, from studying blood flow dynamics to testing new vascular devices. This versatility can increase the scope and applicability of research findings. By providing a more accurate and adaptable model, the self-rolling shunt enhances the quality of research data. This leads to better understanding and development of new therapies, ultimately improving patient outcomes. Ethical Advantages: The use of the self-rolling shunt in research can reduce the reliance on animal models, addressing ethical concerns and improving the acceptance of research findings.

Figure 44C:
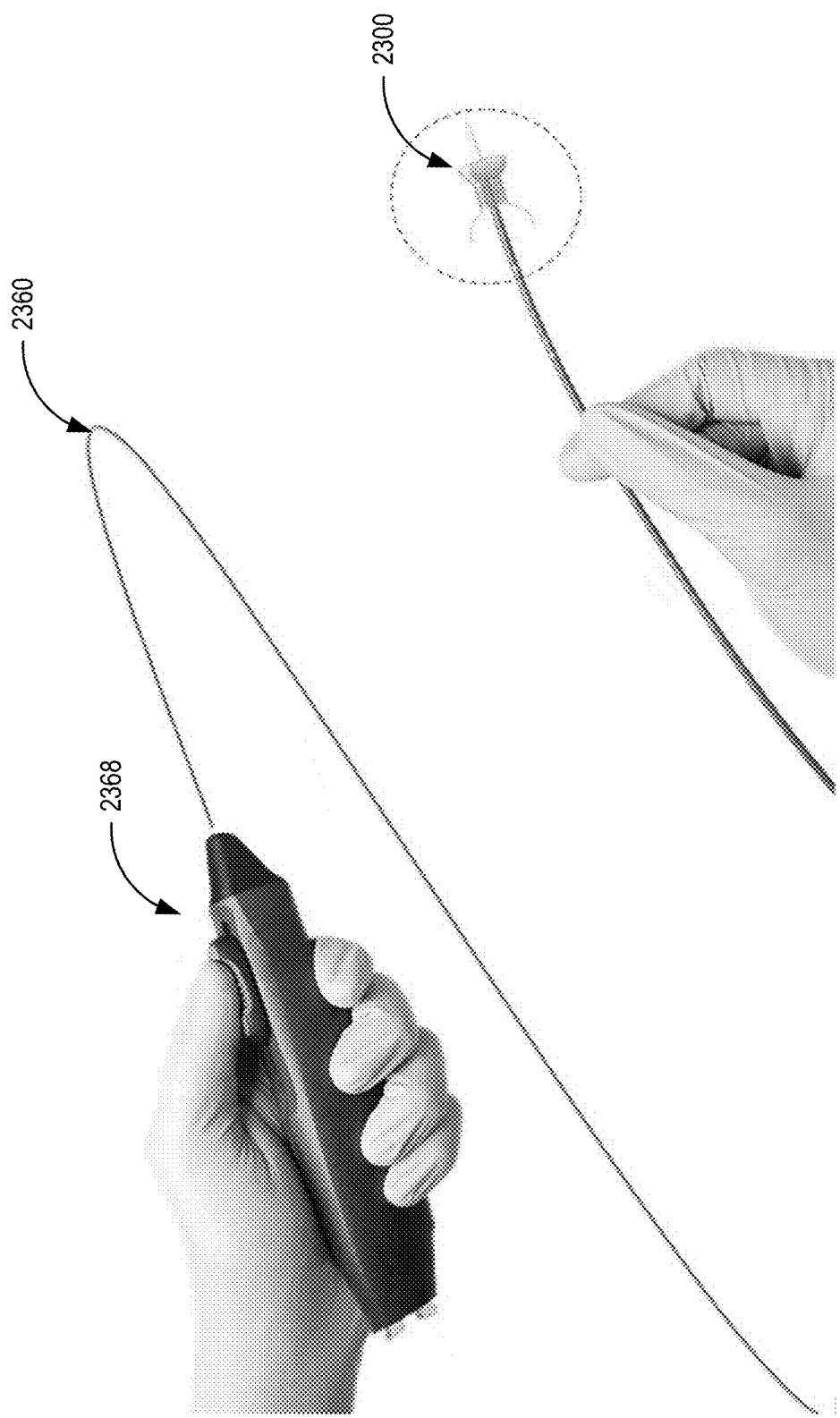

FIGS. 44A-44C show a handle 2368 for a shunt delivery system. As shown, the handle 2368 may be coupled to a catheter 2360 through which the shunt 2300 may be deployed. The handle 2368 includes an actuator for 2374. The catheter 2360 may include a guidewire lumen that runs longitudinally through the handle and catheter shaft. The guidewire lumen allows for the passage of a guidewire. The guidewire can be used to navigate the catheter to the target site within the vascular system. In some embodiments, the guidewire lumen may include a smooth inner surface to minimize friction and facilitate easy movement of the guidewire. The lumen can be sized to accommodate standard guidewires used in interventional procedures, promoting compatibility and ease of use. The material of the lumen may be selected for its low friction coefficient. In some embodiments, the material of the lumen may include, for example, fluoropolymers such as polytetrafluoroethylene (PTFE) to further reduce resistance and enhance guidewire maneuverability. The smooth inner surface may minimize the risk of guidewire kinking or snagging, promoting smooth and precise navigation.

In some embodiments, a flush port (not shown) may be included in the catheter handle 2368 to allow for the flushing of the catheter system 2360. The flush port may be useful for maintaining the patency of the catheter 2360 and preventing the buildup of blood clots or other debris within the lumen of the catheter 2360. The handle 2360 and/or the flush port may include a connector 2369, enabling secure attachment to a syringe or infusion line. In some embodiments, the syringe can be coupled to the connector 2369 to deliver image contrast, saline, or any other fluid through the guide wire lumen. The connector (e.g., a Luer Lock connector, a Y connector, etc.) may further allow flushing to be performed efficiently and effectively, maintaining the integrity of the catheter system throughout the procedure. The connector 2369 may be configured to provide a leak-proof connection such that the flushing fluid is directed through the catheter system and minimizing leakage. In some embodiments, the connector 2369 can provide an opening into the guidewire lumen through which the guidewire can be introduced. In some embodiments, the flush port can be coupled to the handle 2368 in a location provides easy access during the procedure, allowing for quick and convenient flushing as needed.

In some embodiments, the handle 2368 may include a first actuator 2374, such as, for example, a rotating element, a rotation knob, a wheel, etc. As shown, the first actuator 2374 is a rotating conical structure coupled to the catheter 2360. The first actuator 2374 may provide control over the rotation of the catheter shaft 2360. For example, a degree of rotation of the first actuator 2374 may control a degree of rotation of the catheter shaft 2360. The first actuator 2374 may be ergonomically designed to be easily manipulated with one hand of the operator, allowing the operator to rotate the catheter 2360 smoothly and accurately. By actuating the first actuator 2374, the operator can navigate the catheter through the vascular system and position the shunt (e.g., shunt 100, 2000, etc.) or any other interventional device at the target site. The first actuator 2374 may include a locking mechanism (e.g., grooves or detents to block rotation) to maintain the desired rotational position once it has been set. The locking mechanism is designed to provide secure and reliable engagement, preventing unintended rotation during critical phases of the procedure. The first actuator may include one or more features to provide tactile feedback to the operator such that the operator can feel the degree of rotation and make precise adjustments accordingly.

In some embodiments, the handle 2368 may include a second actuator 2372 (e.g., a linear slider, a rack and pinion system, etc.) configured to facilitate deployment of the shunt. As shown, the second actuator 2372 includes a linear slider including an engagement surface configured to be pushed proximally and/or distally. The second actuator 2372 may be connected to the catheter shaft 2360 and allow the operator to advance or retract the shunt delivery system. The second actuator 2372 may include a tactile feedback mechanism (e.g., one or more indents, detents, grooves, ridges, raised portions, etc. configured to temporarily engage a portion of the second actuator 2372 as it is actuated) to provide the operator with sensory feedback during deployment to help the operator accurately deployment of the shunt. The second actuator 2372 may also include a locking mechanism to secure the shunt in place (e.g., prevent movement of the shunt relative to the catheter 2360) until the shunt is ready to be deployed, thereby preventing accidental deployment during navigation. The tactile feedback mechanism may be configured to provide incremental feedback corresponding to the advancement or retraction of the shunt. In some embodiments, the tactile feedback mechanism may be configured such that the second actuator 2372 is encouraged or urged towards predefined positions along the length of the sliding path. For example, the tactile feedback mechanism may include a track including features (e.g., divets, cut outs, indentations, and/or ridges) to urge the second actuator 2372 to move into a predefined position. In some embodiments, the tactile feedback mechanism may be configured to provide tactile feedback (e.g., the user may feel a "click" or a vibration) when the second actuator 2372 moves or slides into each predefined position. The tactile feedback mechanism allows for secure shunt positioning and reliable deployment.

In some embodiments, the handle 2368 may be ergonomic such that the operator can comfortably hold and manipulate the handle 2368 for extended periods. For example, the handle 2368 may include a contoured grip that conforms to the natural shape of the hand, reducing operator fatigue and enhancing control. In some embodiments, 2368 a shape of the handle 2368 may correspond to a shape of an inner surface of the hand of the user. In some embodiments, the guidewire lumen, flush port, first actuator, and second actuator 2372 are positioned on the handle 2368 for ease of access and operation such that the handle 2368 can be used efficiently during complex interventional procedures. In some embodiments, the handle 2368 can include materials with varying textures to enhance grip and comfort (e.g., a material or surface features to increase friction between the handle 2368 and the hand of the operator), reducing the likelihood of slippage even in a wet operating environment. A total weight of the handle 2368 and a weight distribution of the handle 2368 may be configured to minimize hand strain, allowing for precise and steady manipulation during prolonged procedures.

In some embodiments, the handle 2368 may include a biocompatible material such as, for example, medical-grade plastics, stainless steel, or a suitable combination thereof. These materials may provide durability, resistance to corrosion, and compatibility with sterilization processes. The handle 2368 may be configured to withstand the rigors of repeated use in a clinical setting while maintaining its functionality and safety. In some embodiments, medical-grade plastics, such as polycarbonate or polyether ether ketone (PEEK), can be included in a main body of the handle 2368 due to their strength and lightweight properties. In some embodiments, stainless steel components can be included in the handle 2368 for parts requiring high strength and precision, such as the first actuator and/or second actuators 2372. The material of the handle 2368 may be configured such that the handle can be sterilized using standard methods, such as autoclaving or ethylene oxide gas, without degrading its performance or structural integrity. The handle 2368 may be structurally and/or functionally similar to the handle 1168, and therefore, further details around the handle 2368 are not described herein with respect to FIGS. 44A-44C.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. An apparatus, comprising:
a shunt including a first end and a second end,
the shunt configured to transition between a delivery configuration in which the shunt is cylindrical and a deployed configuration in which the second end of the shunt has rolled to form a ring-like structure and to decrease a total length of the shunt,
wherein when the shunt is at least partially disposed in an anatomical structure, the shunt is configured to dynamically adjust the total length of the shunt by further rolling or unrolling the ring-like structure based on changes in the anatomical structure or pressure conditions in an environment around the shunt.

2. The apparatus of claim 1, wherein the first second end of the shunt forms the ring-like structure when the first second end rolls toward the first end central portion, the ring-like structure is configured to anchor the shunt relative to a vessel.

3. The apparatus of claim 2, wherein the second first end expands radially to form a disc shape when the shunt transitions from the delivery configuration to the deployed configuration.

4. The apparatus of claim 1, further comprising:
a delivery catheter configured to constrain the shunt in the delivery configuration and to release the shunt to allow the shunt to transition to the deployed configuration.

5. The apparatus of claim 1, wherein the shunt includes at least one radiopaque marker.

6. The apparatus of claim 1, wherein the shunt is configured to, upon transition from the delivery configuration to the deployed configuration, invert at least a portion the second end outwardly so that at least a portion of the second end is directed towards the first end.

7. The apparatus of claim 1, wherein the second end of the shunt is configured to invert towards the first end upon transition from the delivery configuration to the deployed configuration, such that an inner surface of at least a portion of the second end faces outwardly to create an anchoring structure.

8. The apparatus of claim 1, wherein at least a portion of the second end of the shunt is configured to invert outwardly towards the first end upon transition from the delivery configuration to the deployed configuration, resulting in an outwardly facing inner surface.

9. The apparatus of claim 1, wherein at least a portion of the shunt is formed of bioabsorbable material.

10. The apparatus of claim 1, further comprising a cover coupled to at least a portion of the shunt.

11. The apparatus of claim 10, wherein the cover includes polylactic acid (PLA) or polyglycolic acid (PGA) to support tissue ingrowth.

12. The apparatus of claim 10, wherein a central portion is configured to span a space between a first vessel and a second vessel.

13. The apparatus of claim 1, further comprising a central portion between the first end and the second end, the first end of the shunt is configured to be disposed in a first vessel, the second end of the shunt is configured to be disposed in a second vessel, and the central portion is configured to convey fluid therebetween.

14. The apparatus of claim 13, wherein the second end of the shunt is configured to unroll to transition the shunt from the deployed configuration back to the delivery configuration.

15. The apparatus of claim 13, wherein the ring-like structure is configured to unroll to increase the total length of the shunt as a length of a space between the first vessel and the second vessel increases.

16. The apparatus of claim 1, wherein the ring-like structure is a toroidal structure.

17. The apparatus of claim 1, wherein the shunt is configured to treat an aortic aneurysm.

18. The apparatus of claim 1, further comprising a central portion defining a lumen between the first end and the second end.

19. The apparatus of claim 1, wherein the shunt has a delivery length in the delivery configuration, when the shunt is at least partially disposed in the anatomical structure, the shunt is configured to dynamically adjust the total length of the shunt between 20% of a delivery length and about 95% of the delivery length.

20. The apparatus of claim 1, wherein the shunt is at least partially formed of braided filaments defining a plurality of cells, a size of the cells varying between the first end and the second end of the shunt.

21. The apparatus of claim 1, wherein when the shunt is in the deployed configuration, the first end of the shunt expands into a shape different than the ring-like structure.

22. The apparatus of claim 21, wherein the shape of the first end is configured to secure the shunt relative to a first anatomical structure, the second end is configured to roll and unroll relative to the first end.

23. An apparatus, comprising:
a shunt including a first end, a second end, and a central portion therebetween,
the shunt configured to transition between a delivery configuration in which the shunt is cylindrical and a deployed configuration in which the first end expands radially to form a disc shape and at least a portion of the second end inverts into a ring-like structure such that a total length of the shunt decreases.

24. The apparatus of claim 23, wherein when the shunt is at least partially disposed in an anatomical structure, the shunt is configured to dynamically adjust the total length of the shunt by rolling or unrolling the ring-like structure based on changes in the anatomical structure or pressure conditions in an environment around the shunt.

25. The apparatus of claim 23, wherein the disc shape is configured to secure the shunt relative to a first anatomical structure to prevent movement of the shunt, and the second end is configured to roll and unroll relative to the disc shape.

26. The apparatus of claim 23, wherein the shunt is configured to, upon transition from the delivery configuration to the deployed configuration, invert at least a portion the second end outwardly so that at least a portion of the second end is directed towards the central portion.

27. The apparatus of claim 23, wherein the second end of the shunt is configured to invert towards the first end upon transition from the delivery configuration to the deployed configuration, such that an inner surface of the second end faces outwardly to create an anchoring structure.

28. The apparatus of claim 23, wherein the first end of the shunt is configured to be disposed in a first vessel, the second end of the shunt is configured to be disposed in a second vessel, and the central portion is configured to span a space between the first vessel and the second vessel and to convey fluid therebetween, the ring-like structure is configured to unroll to increase the total length of the shunt as a length of the space between the first vessel and the second vessel increases.

29. The apparatus of claim 23, wherein the ring-like structure is a toroidal structure.

30. The apparatus of claim 23, wherein when the shunt is in the deployed configuration, a lateral length of the disc shape is less than a lateral length of the ring-like structure.

31. The apparatus of claim 23, wherein the shunt is at least partially formed of braided filaments defining a plurality of cells, a size of the cells varying between the first end and the second end of the shunt.

32. An apparatus, comprising:
a shunt including a first end and a second end,
the shunt configured to transition between a delivery configuration in which the shunt is cylindrical and a deployed configuration in which the first end forms a first shape configured to fix the shunt relative to an anatomical structure to prevent movement of the shunt,
the second end, when the shunt is at least partially disposed in the anatomical structure, is configured to roll and unroll relative to the first end to dynamically adjust a total length of the shunt based on changes in conditions around the shunt.

33. The apparatus of claim 32, wherein the second end forms a toroidal structure, the second end of the shunt forms the toroidal structure when the second end rolls toward the first end.

34. The apparatus of claim 33, wherein when the shunt is in the deployed configuration, the first end of the shunt expands into the first shape, the first shape being different than the toroidal structure.

35. The apparatus of claim 33, wherein to form the first shape the first end expands radially to form a disc shape when the shunt transitions from the delivery configuration to the deployed configuration.

36. The apparatus of claim 33, wherein when the shunt is in the deployed configuration, a lateral length of the first shape is smaller than a lateral length of ring-like structure.

37. The apparatus of claim 32, wherein the shunt is configured to, upon transition from the delivery configuration to the deployed configuration, invert at least a portion the second end outwardly so that at least a portion of the second end is directed towards the first end.

38. The apparatus of claim 32, wherein the second end of the shunt is configured to invert towards the first end upon transition from the delivery configuration to the deployed configuration, such that an inner surface of the second end faces outwardly to create an anchoring structure.

39. The apparatus of claim 32, wherein the first end of the shunt is configured to be disposed in a first vessel, the second end of the shunt is configured to be disposed in a second vessel, and a central portion of the shunt is configured to span a space between the first vessel and the second vessel and to convey fluid therebetween, the second end is configured to unroll to increase the total length of the shunt as a length of the space between the first vessel and the second vessel increases.

40. The apparatus of claim 32, wherein when the shunt is disposed in the anatomical structure, the shunt is configured to dynamically adjust the total length of the shunt by 20% of the delivery length of the shunt to about 95% of the delivery length of the shunt.

* * * * *